(12) United States Patent
Oldfield et al.

(10) Patent No.: US 8,012,949 B2
(45) Date of Patent: *Sep. 6, 2011

(54) BISPHOSPHONATE COMPOUNDS AND METHODS WITH ENHANCED POTENCY FOR MULTIPLE TARGETS INCLUDING FPPS, GGPPS, AND DPPS

(75) Inventors: Eric Oldfield, Champaign, IL (US); Yonghui Zhang, Urbana, IL (US); Fenglin Yin, Naperville, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 272 days.

This patent is subject to a terminal disclaimer.

(21) Appl. No.: 12/101,484

(22) Filed: Apr. 11, 2008

(65) Prior Publication Data

US 2008/0255070 A1 Oct. 16, 2008

Related U.S. Application Data

(63) Continuation-in-part of application No. 11/687,570, filed on Mar. 16, 2007, now Pat. No. 7,687,482, which is a continuation-in-part of application No. PCT/US2007/064239, filed on Mar. 16, 2007, which is a continuation-in-part of application No. 11/245,612, filed on Oct. 7, 2005, now Pat. No. 7,358,361, which is a continuation-in-part of application No. PCT/US2005/036425, filed on Oct. 7, 2005.

(60) Provisional application No. 60/911,426, filed on Apr. 12, 2007, provisional application No. 60/783,491, filed on Mar. 17, 2006, provisional application No. 60/783,491, filed on Mar. 17, 2006, provisional application No. 60/617,108, filed on Oct. 8, 2004, provisional application No. 60/617,108, filed on Oct. 8, 2004.

(51) Int. Cl.
*A61K 31/675* (2006.01)
*C07F 9/06* (2006.01)

(52) U.S. Cl. .............. 514/89; 514/82; 546/22; 546/23; 546/24

(58) Field of Classification Search .............. 546/22, 546/23, 24; 514/89, 82
See application file for complete search history.

(56) References Cited

U.S. PATENT DOCUMENTS

| | | |
|---|---|---|
| 4,608,368 A | 8/1986 | Blum et al. |
| 4,621,077 A | 11/1986 | Rosini et al. |
| 4,711,880 A | 12/1987 | Stahl et al. |
| 4,777,163 A | 10/1988 | Bosies et al. |
| 4,810,486 A | 3/1989 | Kelly et al. |
| 4,859,472 A | 8/1989 | Demmer et al. |
| 4,871,720 A | 10/1989 | Jaeggi |
| 4,927,814 A | 5/1990 | Gall et al. |
| 4,939,130 A | 7/1990 | Jaeggi et al. |
| 5,196,409 A | 3/1993 | Breuer et al. |
| 5,227,506 A | 7/1993 | Saari et al. |
| 5,294,608 A | 3/1994 | Lang et al. |
| 5,312,954 A | 5/1994 | Breuer et al. |
| 5,338,731 A | 8/1994 | Breuer et al. |
| 5,462,932 A | 10/1995 | Brenner et al. |
| 5,583,122 A | 12/1996 | Benedict et al. |
| 5,639,653 A | 6/1997 | Bloom et al. |
| 5,719,303 A | 2/1998 | Yoshida et al. |
| 5,756,423 A | 5/1998 | Cromartie et al. |
| 5,994,329 A | 11/1999 | Daifotis et al. |
| 6,015,801 A | 1/2000 | Daifotis et al. |
| 6,057,306 A | 5/2000 | Wilson et al. |
| 6,096,342 A | 8/2000 | Dansereau et al. |
| 6,143,326 A | 11/2000 | Mockel et al. |
| 6,165,513 A | 12/2000 | Dansereau et al. |
| 6,214,812 B1 | 4/2001 | Karpeisky et al. |
| 6,225,294 B1 | 5/2001 | Daifotis et al. |
| 6,294,196 B1 | 9/2001 | Gabel et al. |
| 6,372,728 B1 | 4/2002 | Ungell |
| 6,410,520 B2 | 6/2002 | Cazer et al. |
| 6,541,454 B1 | 4/2003 | Breuer et al. |

(Continued)

FOREIGN PATENT DOCUMENTS

DE 3719513 A1 12/1988

(Continued)

OTHER PUBLICATIONS

Mancini et al. (Sep. 2004) "Efficacy and Safety of Ibandrinate in the Treatment of Opiod-Resistant Bone Pain Associated With Metastic Bone Disease: A Pilot Study," Journal Chemcial Oncology V22(17) Sep. 1, 2004, pp. 3587-3592.

(Continued)

*Primary Examiner* — Rei-tsang Shiao
(74) *Attorney, Agent, or Firm* — Greenlee Sullivan P.C.

(57) ABSTRACT

The disclosure provides, inter alia, novel bisphosphonate compounds and methods of making and using such compounds. In certain embodiments, compounds of the invention include bisphosphonates that are capable of selectively inhibiting one or more of farnesyl diphosphate synthase (FPPS), geranylgeranyl diphosphate synthase (GGPPS), and decaprenyl pyrophosphate synthase (DPPS). In preferred embodiments, compounds of the invention are capable of selectively inhibiting two or more of FPPS, GGPPS, and DPPS. In embodiments, compounds and methods of the invention demonstrate superior activity levels, such as in the anti-cancer context, immunostimulation context, and other contexts, which in several cases exceed the activity levels of previous generation bisphosphonate drugs by orders of magnitude. In embodiments, the invention provides compounds and methods in connection with research and therapeutic applications, e.g., for tumor or cancer cell growth inhibition, activation of gammadelta T cells, inhibition of certain enzymes related to the mevalonate metabolic pathway, bone resorption diseases, cancer, immune disorders, immunotherapy, and infectious diseases.

44 Claims, 14 Drawing Sheets

U.S. PATENT DOCUMENTS

| | | | |
|---|---|---|---|
| 6,544,967 | B2 | 4/2003 | Daifotis et al. |
| 6,548,042 | B2 | 4/2003 | Arstad et al. |
| 6,562,974 | B2 | 5/2003 | Cazer et al. |
| 6,638,920 | B2 | 10/2003 | Thompson |
| 6,696,427 | B1 | 2/2004 | Jomaa |
| 6,753,324 | B2 | 6/2004 | Jomaa |
| 6,984,400 | B2 | 1/2006 | Golomb et al. |
| 7,008,645 | B2 | 3/2006 | Golomb et al. |
| 7,358,361 | B2 * | 4/2008 | Sanders et al. ......... 546/22 |
| 7,425,549 | B2 | 9/2008 | Little et al. |
| 7,560,490 | B2 | 7/2009 | Zanetti et al. |
| 7,687,482 | B2 | 3/2010 | Oldfield et al. |
| 7,687,570 | B2 | 3/2010 | Kurihara et al. |
| 7,745,422 | B2 | 6/2010 | Sanders et al. |
| 2002/0042539 | A1 | 4/2002 | Arstad et al. |
| 2004/0087554 | A1 | 5/2004 | Blum et al. |
| 2005/0113331 | A1 | 5/2005 | Prniak et al. |
| 2006/0079487 | A1 | 4/2006 | Sanders et al. |
| 2007/0275931 | A1 | 11/2007 | Oldfield et al. |
| 2008/0255070 | A1 | 10/2008 | Oldfield et al. |
| 2008/0318906 | A1 | 12/2008 | Sanders et al. |
| 2010/0316676 | A1 | 12/2010 | Sanders et al. |

FOREIGN PATENT DOCUMENTS

| | | |
|---|---|---|
| DE | 19738005 A1 | 3/1999 |
| DE | 19859668 | 12/1999 |
| JP | 55098193 | 7/1980 |
| PL | 172268 B1 | 8/1997 |
| SU | 1022970 A1 | 6/1983 |
| WO | WO9420508 A1 | 9/1994 |
| WO | WO 95/34207 | 12/1995 |
| WO | WO 97/08178 | 3/1997 |
| WO | WO9712619 A1 | 4/1997 |
| WO | WO 00/03677 | 1/2000 |
| WO | WO 02/11704 | 2/2002 |
| WO | WO 02/076515 | 10/2002 |
| WO | WO 03/021031 | 3/2003 |
| WO | WO 03/075741 | 9/2003 |
| WO | WO 03/097655 | 11/2003 |
| WO | WO 2004/024165 | 3/2004 |
| WO | WO 2004/050096 | 6/2004 |
| WO | WO 2004/060327 | 7/2004 |
| WO | WO 2005/023270 | 3/2005 |
| WO | WO 2005/027842 | 3/2005 |
| WO | WO 2006/039721 | 4/2006 |
| WO | WO 2007/109585 | 9/2007 |
| WO | WO 2008/128056 | 10/2008 |

OTHER PUBLICATIONS

Alfer'ev et al. (1983) "Reactions of Vinylidenediphosphonic Acid with Nucleophiles. 1. Addition of Alipathic Amines," *Bull. Acad. Sci. USSR Div. Chem. Sci.* 32:2515-2518.

Alfer'ev et al. (1984) "Addition of Nucleophilic Agents to Vinylidenediphosphonic Acid. Communication 2. Reactions of Vinylidenediphosphonic Acid with Primary Amines, Ammonia, and Hydrazine," *Bull. Acad. Sci. USSR Div. Chem. Sci.* 33:1031-1035.

Alfer'ev et al. (Aug. 1994) "Reactions of Vinylidenediphosphonic Acid with Nucleophiles. 5. Addition of Heterocyclic Amines and Trimethylamine to Vinylidenediphosphonic Acid," *Russian Chem. Bull.* 44(8):1528-1530.

Amin. et al. (Aug. 1996) "1-Hydroxy-3-(methylpentylamino)-propylidene-1, 1-bisphosphonic Acid as a Potent Inhibitor of Squalene Synthase," *Arzneimittelforschung* 46:759-762.

Amin et al. (1992) "Bisphosphonates Used for the Treatment of Bone Disorders Inhibit Squalene Synthase and Cholesterol Biosynthesis," *J. Lipid Res.* 33:1657-1663.

Bergstrom et al. (Jan. 1, 2000) Alendronate is a Specific, Nanomolar Inhibitor of Farnesyl diphosphate synthase, Arch. Biochem. Biophys. 373(1):231-241.

Blattman et al. (Jul. 2004) "Cancer Immunotherapy: A Treatment for the Masses," *Science* 305:200-205.

Body et al. (2004) "Oral Ibandrinate Improves Bone Pain and Preserves Quality of Life in Patients with Skeletal Metastases Due to Breast Cancer," *Pain* 111:306-312.

Bouzahzah et al. (Jun. 2005) "Risedronate in the Treatment of Murine Chagas' Disease," *Parasitol. Res.* 96:184-187.

Brunger et al. (1998) "Crystallography & NMR System A New Software Suite for Macromolecular Structure Determination," *Acta Crystallogr D Biol Crystallogr.* 54(5):905-921.

Bundgaard, H. (1985) "Design of Prodrugs," *Methods Enzymol.* 112:309-396.

Bundgaard, H. (1992) "Means to Enhance Penetration. (1) Prodrugs as a Means to Improve the Delivery of Peptide Drugs," *Adv. Drug. Deliv. Rev.* 8:1-38.

Bundgaard, H.(1991) "Design and Application of Prodrugs," In; *A Textbook of Drug Design and Development*, Krosgaard-Larsen et al. Eds., Ch. 5, pp. 113-191.

Burke et al. (Feb. 2004) "Heteromeric Geranyl Diphosphate Synthase from Mint: Construction of a Functional Fusion Protein and Inhibition by Bisphosphonate Substrate Analogs," *Arch. Biochem. Biophys.* 422 (1):52-60.

Buxton et al. (2004) "Bisphosphonate-ciprofloxin Bound to Skelite is a Prototype for Enhancing Experimental Local Antibiotic Delivery to Injured Bone," *Br. J. Surg.* 91:1192-1196.

Cao et al. (2006) "[2-(3-Fluoropyridinium-1-yl)-1-hydroxy-1-phosphonoethyl]phosphonate," *Acta Cryst.* E62:o1003-o1005.

Cao et al. (2006) "[1-Hydroxy-1-phosphono-2-(trimethylphosphonium-1-yl)ethyl]phosphonate Monohydrate," *Acta Cryst.* E62:o1055-o1057.

Caraglia et al. (2004) "The Farnesyl Transferase Inhibitor R115777 (Zarnestra) Synergistically Enhances Growth Inhibition and Apoptosis Induced on Epidermoid Cancer Cells by Zoledronic Acid (Zometa) and Pamidronate," *Oncogene* 23:6900-6913.

Chen et al. (Sep. 25, 2008) "Inhibition of Geranyl Diphosphate Synthase by Bisphosphonates: A Crystallographic and Computational Investigation," *J. Med. Chem.* 51(19):5594-5607.

Cohen et al. (1999) "Synthesis and Preclinical Pharmacology of 2-(20Aminopyrimidinio) Ethylidene-1, 1-Bisphosphonic Acid Betaine (ISA-13-1)—A Novel Bisphosphonate," *Pharmaceutical Res.* 16(9):1399-1406.

Cohen et al. (1998) "Bisphosphonates and Tetracycline: Experimental Modes for Their Evaluation in Calcium-Related Disorders," *Pharmaceutical Res.* 15(4):606-613.

Cromartie et al. (1999) "The Discovery of a Novel Site of Action for Herbicidal Bisphosphonates," *Pesticide Biochem. Phys.* 63:114-126.

Davisson et al. (1986) "Phosphorylation of Isoprenoid Alcohols," *J. Org. Chem.* 51:4768-4779.

Dawson, N.A. (2003) "Therapeutic Benefit of Bisphosphonates in the Management of Prostate Cancer-Related Bone Disease," *Exp. Opin. Pharmacother.* 4:705-716.

De Cock et al. (Aug. 2005) "Cost-Effectiveness or Oral Ibandronate Versus IV Zoledronic Acid or IV Pamidronate for Bone Metastases in Patients Receiving Oral Hormonal Therapy for Breast Cancer in the United Kingdom," *Clin. Ther.* 27(8):1295-1310.

Desouki et al. (Dec. 2005) "Cross Talk Between Mitochondria and Superoxide Generating NADPH Oxidase in Breast and Ovarian Tumors," *Cancer Biol. Ther.* 4(12):1367-1373.

Dickson et al. (Aug. 2006) "Efficacy of Zoledronate Against Neutoblastoma," *Surgery* 140:227-235.

Ding et al. (2006) "Preparation of Phosphonic Acid Derivatives for the Treatment of Osteoporosis," *CAS* 145:211178.

Dunford et al. (2001) "Structure-Activity Relationships for Inhibition of Farnesyl Diphosphate Synthase in Vitro and Inhibition of Bone Resorption in Vivo by Nitrogen-Containing Bisphosphonates," *J. Pharmacol. Exp. Ther.* 296(2):235-242.

Fisher et al. (Jan. 1999) "Alendronate Mechanism of Action: Geranylgeraniol, an Intermediate in the Mevalonate Pathway, Prevents Inhibition of Osteoclast Formation, Bone Resorption, and Kinase Activation in Vitro," *Proc. Nat. Acad. Sci.* 96:133-138.

Forsea et al. (2004) "Nitrogen-Containing Bisphosphonates Inhibit Cell Cycle Progression in Human Melanoma Cells," *Br. J. Cancer* 91:803-810.

Gabelli et al. (Jan. 2006) "Structure and Mechanism of the Farnesyl Diphosphate Synthase from *Trypanosoma cruzi*: Implications for Drug Design," *Proteins* 62:80-88.

Garzoni et al. (2004) "Antiparasitic Activity of risedronate in a Murine Model of Acute Chagas' Disease," *Int. J. Antimicrobial Agents* 23:286-290.

Garzoni et al. (Aug. 2004) "Selective In Vitro Effects of the Farnesyl Pyrophosphate Synthase Inhibitor Risedronate on *Trypanosoma cruzi*," *Int. J. Antimicrobial Agents* 23:273-285.

Gedeck et al. (2006) "QSAR-How Good is it in Practice? Comparison of Descriptor Sets on an Unbiased Cross Section of Corporate Data Sets," *J. Chem. Inf. Model.* 46(5):1924-1936.

Ghosh et al. ((2004) "Effects of Bisphosphonates on the Growth of *Entamoeba histolytica* and *Plamodium* Species in Vitro and in Vivo," *J. Med. Chem.* 47:175-187 (Including for CAS 140:138740).

Gober et al. (Jan. 2003) "Human T Cell Receptor γδ Cells Recognize Endogenous Mevalonate Metabolites in Tumor Cells," *J. Exp. Med.* 197:163-168.

Goffinet et al. (2006) "Zoledronic Acid Treatment Impairs Protein Gerabyl-Geranylation for Biological Effects in Prostatic Cells," *BMC Cancer* 6:60.

Goldstein et al. (1990) "Regulation of the Mevalonare Pathway," *Nature* 343:425-430.

Gordon, D.H. (2005) "Efficacy and Safety of Intravenous Bisphosphanates for Patients with Breast Cancer Metastic to Bone: A Review of Randomized, Double-Blind, Phase III Trials," *Clin. Breast Cancer* 6(2):125-131.

Green, J.R. (Apr. 2001) "Chemical and Biological Prerequisites for Novel Bisphosphonate Molecules: Results of Comparative Preclinical Studies," *Sem. Oncol.* 28(2 Supp. 6):4-10.

Green et al. (2005) "Skeletal Complications of Prostate Cancer: Pathophysiology and Therapeutic Potential of Bisphosphonates," *Acta Oncol.* 44:282-292.

Green, J.R. (2004) "Bisphosphonates: Preclinical Review," *The Oncologist* 9(supp 4):3-13.

Grove et al. (2000) "The Inracellular Target for the Antiresorptive Aminobisphosphonate Drugs in Dictyostelium discoideum is the Enzyme Farnesyl Diphosphate Synthase," *J. Bone Miner. Res.* 15(5):971-981.

Guo et al. (Jun. 12, 2007) "Bisphosphonates Target Multiple Sites in Both *cis*- and trans-prenyltransferases," *Proc. Nat. Acad. Sci. USA* 104(24):10022-10027.

Halgren et al. (1996) "The Merck Molecular Force Field. Bridging the Gap—From Small Organics to Proteins," *Abst. Papers Am. Chem. Soc.* 211:70.

Heidenreich et al. (2004) "Ibandronate in Metastic Bone Pain," *Sem. Oncol.* 31(5 supp 10):67-72.

Herczegh et al. (2002) "Osteoadsorptive Bisphosphonate Derivatives of Fluoroquinolone Antibacterials," *J. Med. Chem.* 45:2338-2341.

Hopkins et al. (Feb. 2006) "Can We Rationally Design Promiscuous Drugs," *Curr. Opin. Struct. Biol.* 16:127-136.

Hosfield et al. (Mar. 2004) "Structural Basis for Bisphosphonate-Mediated Inhibition of Isoprenoid Biosynthesis," *J. Biol. Chem.* 279:8526-8529.

Hudock et al. (2006) "1-Hydroxy-1-phosphono-2-(trimethylarsonium-1-yl_ethanephosphonate Monohydrate," *Acta Cryst.* E62:o843-o845.

Inoue et al. (2003) "New Synthesis of *gem*-Bis(phosphono)ethylenes and their Applications," *Synthesis* 13:1971-1976.

Inoue et al. (Sep. 15, 2005) "Effect of Combination Therapy with a Novel Bisphosphonate, Minodronate (YM529), and Docetaxel on a Model of Bone Metastasis by Human Transitional Cell Carcinoma," *Clin. Cancer Res.* 11(18):6669-6677.

International Search Report and Written Opinion, Corresponding to International Application No. PCT/US2008/060051, Mailed Sep. 25, 2008.

International Search Report and Written Opinion, Corresponding to International Application No. PCT/US05/36425, Mailed May 2, 2006.

International Search Report and Written Opinion, Corresponding to International Application No. PCT/US07/64239, Mailed Aug. 21, 2008.

Jagdev et al. (2001) "The Bisphosphonate, Zoledronic Acid, Induces Apoptosis of Breast Cancer Cells: Evidence for Synergy with Paclitaxel," *Br. J. Cancer* 84:1126-1134.

Jones et al. (1991) "Improved Methods for Building Protein Models in Electron Density Maps and the Location of Errors in these Models," *Acta Crystallographica Section A* 47:110-119.

Kato et al. (2001) "Targeting of Tumor Cells for Human Gammadelta T Cells by Nonpeptide Antigens," *J. Immunol.* 167:5092-5098.

Kavanagh et al. (May 16, 2006) "The Molecular Mechanism of Nitrogen-Containing Bisphosphonates as Antiosteoporosis Drugs," *Proc. Nat. Acad. Sci. USA* 103(20):7829-7834.

Kavanagh et al. (May 2006) "The Crystal Structure of Human Geranylgeranyl Pyrophosphate Synthase Reveals a Novel Hexameric Arrangement and Inhibitory Product Binding," *J. Biol. Chem.* 281:22004-22012.

Keller et al. (1999) "Mechanism of Aminobisphosphonate Action: Characterization of Alendronate Inhibition of the Isoprenoid Pathway," *Biochem. Biophys. Res. Commun.* 266:560-563.

Kieczykowski et al. (1995) "Preparation of (4-Amino-1-hydroxybutylidene)bisphosphonic and Sodium Salt, MK-217 (alendronate Sodium). An Improved Procedure for the Preparation of 1-hydroxy-1, 1-bisphosphonic Acids," *J. Org. Chem.* 60:8310-8312.

Klebe et al. (Nov. 25, 1994) "Molecular Similarity Indices in a Comparative Analysis (CoMSIA) of Drug Molecules to Correlate and Predict their Biological Activity," *J. Med. Chem.* 37(24):4130-4136.

Klein et al. (1998) "Structurally Different Bisphosphonates Exert Opposing Effects on Alkaline Phosphate and Mineralization in Marrow Osteoprogenitors," *J. Cell. Biochem.* 68:186-194.

Kotsikorou et al. (2003) "A Quantitative Structure-Activity Relationship and Pharmacophore Modeling Investigation of Aryl-X and Heterocyclic Bisphosphonates as Bone Resorption Agents," *J. Med. Chem.* 46(14):2932-2944 (Including for CAS 139:190645).

Kotsikorou et al. (2005) "Bisphosphonate Inhibition of the Exopolyphosphatase Activity of the *Trypanosoma brucei* Soluble Vacuolar Pyrophosphatase," *J. Med. Chem.* 48:6128-6139.

Krapcho et al. (1998) "Synthesis or Regioisomeric Difluoro- and 8-Chloro-9-fluorobenz[g]isoquinoline-5, 10-diones and SNAr Displacements Studies by Diamines: Bis(aminoalkyl)aminobenz[g]isoquinoline-5, 10-diones," *J. Fluorine Chem.* 90:139-147.

Kubo et al. (2007) "Efficacy of a Nitrogen-Containing Bisphosphonate, Minodronate, in Conjunction with a p38 Mitogen Activated Protein Kinase Inhibitor or Docorubicin Against Malignant Bone Tumor Cells," *Cancer. Chemother. Pharmacol.* 62(1):111-116.

Kubo et al. (Jun. 2006) "Inhibitory Effects of a New Bisphosphonate, Minodronate, on Proliferation and Invasion of a Variety of Malignant Bone Tumor Cells," *J. Orthop. Res.* 24:1138-1144.

Kunzmann et al. (Jul. 15, 2000) "Stimulation of γδ T Cells by Aminobisphosphonates and Induction of Antiplasma Cell Activity in Multiple Myeloma," *Blood* 96:384-392.

Lecouvey et al. (2001) "A Mild and Efficient One-Pot Synthesis of 1-Hydroxymethylene-1, 1-bisphosphonic Acids. Preparation of a New Tripod Ligands," *Tetrahedron Lett.* 42:8475-8478.

Lee et al. (2005) "Combinations of Chlorpromazine Compounds and Antiproliferative Drugs for the Treatment of Neoplasms," *CAS* 142:349042.

Leon et al. (Dec. 14, 2006) "Isoprenoid Biosynthesis as a Drug Target: Bisphosphonate Inhibition of *Escherichia coli* K12 Growth and Synergistic Effects of Fosmidomycin," *J. Med. Chem.* 49:7331-7341.

Liang, (2002) "Structure, Mechanism and Function or Prenyltransferases," *Eur. J. Biochem.* 269:3339-3354.

Ling et al. (2005) "Bisphosphonate Inhibitors of *Toxoplasma gondi* Growth: In Vitro, QSARm and in Vivo Investigations," *J. Med. Chem.* 48:3130-3140.

Luckman et al. (1998) "Nitrogen-Containing Bisphosphonates Inhibit the Mevalonate Pathway and Prevent Post Translational Prenylation of GTP-Binding Proteins, Including Ras," *J. Bone Miner. Res.* 13(4):581-589.

Mancini et al. (Sep. 2004) "Efficacy and Safety of Ibandrinate in the Treatment of Opiod-Resistant Bone Pain Associated With Metastic Bone Disease: A Pilot Study,".

Mao et al. (2004) "Crystallization and Preliminary X-Ray Diffraction Study of the Farnesyl Diphosphate Synthase from *Trpanosoma brucei*," *Acta Crystallogr. D Biol. Crystallogr*. 60(10):1863-1866.

Mao et al. (Nov. 15, 2006) "Solid-State NMR, Crystallofraphic, and Computational Investigation of Bisphosphonates and Farneyl Diphosphate Sythase-Bisphosphonate Complexes," *J. Am. Chem. Soc*. 128(45):14485-14497.

Martin et al. (Mar. 15, 2001) "Bisphosphonates Inhibit the Growth of *Trypanosoma brucei, Trypanosoma cruzi, Leishmania donocani, Toxoplams gondiim* and *Plasmodium falciparum*: A Potential Route to Chemotherapy," *J. Med. Chem*. 44:909-916 (Including for CAS 134:292629).

Martin et al. (2002) "Activity of Bisphosphonates Against *Trypanosoma brucei* rhodesiense," *J. Med. Chem*. 45:2904-2914 (Including for CAS 137:134485).

Martin et al. (1999) "Nitrogen-Containing Bisphosohonates as Varbocation Transition State Analogs for Isoprenoid Biosynthesis," *Biochem. Biophys. Res. Commun*. 263:754-758.

Medical New Today, Jul. 15, 2006) "Application Filed for the Osteoporosis Treatment ONO-5920/YM529 in Japan," http://www.medicalnewstoday.com/articies/47369.php.

Miwa et al. (Oct. 1, 2005) "The Bisphosphosphonate YM529 Inhibits Osteolytic and Osteoblastic Changes and CXCR-4-Induced Invasion in Prostate Cancer," *Cancer Res*. 65(19):8818-8825.

Miyaura et al. (1981) "The Palladium-Catalyzed Cross-Coupling Reaction of Phenylboronic Acid with Haloarenes in the Presence of Bases," *Synth. Commun* 11:513-519.

Mönkkonen et al. (Feb. 2006) "A New Endogenous ATP Analog (Apppl) Inhibits the Mitochondrial Adenine Nucleotide Translocase (ANT) and is Responsible for the Apoptosis Induced by Nitrogen-Containing Bisphosphonates," *Br. J. Pharmacol*. 147:437-445.

Montalvetti et al. (2001) Bisphosphonates are Potent Inhibitors of *Typanosome cruzi* farnesyl Pyrophosphate Synthase, *J. Biol. Chem*. 276:33930-33937.

Montalvetti et al. (May 2003) "Farnesyl Pyrophosphate Synthase Is and Essential Enzyme in *Tryanosoma brucei*," *J. Biol. Chem*. 278:17075-17083.

Moreno et al. (2001) "31P NMR of Apicomplexans and the Effects of Risedronate on *Cryptospoidium parvum* Growth," *Biochem. Biophys. Res. Commun*. 284:632-637.

Namaka et al. (2004) "A Treatment Algorithm for Neuropathic Pain," *Clin. Ther*. 26(7):951-979.

Navaza et al. (1994) "AMoRe: an Automated Package for Molecular Replacement," *Acta Crystallog. Sect. A* 50:157-163.

Nielsen et al. (Apr. 1988) "Glycolamide Esters as Biolable Prodrugs of Carboxylic Acid Agents: Synthesis, Stability, Bioconversion, and Physiocochemical Properties," *J. Pharm. Sci*. 77(4):285-298.

Norgrady (1985) "Pro-drugs and Soft Drugs," In; *Medicinal Chemistry A Biochemical Approach*, Oxford University Press, New York, pp. 388-392.

Ortmann et al. (2003) "Acyloxyalkyl Ester Prodrugs of FR900098 with Improved in Vivo Anti-Malarial Activity," *Bioorganic Med. Chem. Lett*. 13:2163-2166.

Press, W.H. (1988) "Variable Metric Methods in Multidimensions," In; *Numerical Recopies in C: The Art of Scientific Computing*, Cambridge University Press: New York, pp. 324-328.

Reinholz et al. (2002) "Distinct Mechanisms of Bisphosphonate Action Between Osteoblasts and Breast Cancer Cells: Identity of a Patent New Bisphosphonate Analogue," *Br. Cancer Res*. 71:257-268.

Roberts et al. (May 1998) "Characterization of the Antimonial Antileishmanial Agent Meglumine Antimonate (Glucantime)," *Antimicrobial Agents Chemother*. 42(5):1076-1082.

Rodriguez et al. (2002) "Radical Cure of Experimental Cutaneous Leishmaniasis by the Bisphosphonate Pamidronate," *J. Infect Dis*. 186:138-140.

Roelofs et al. (Oct. 2006) "Molecular Mechanisms of Action of Bisphosphonates: Current Status," *Clin. Cancer Res*. 12:6222s-6230s.

Rogers et al. (1994) "Inhibitory Effects of Bisphosphonates on Growth of Amoebae of the Cellular Clime Mold *Dictyostelium discoideum*," *J. Bone Moner. Res*. 9:1029-1039.

Rondeau et al. (Feb. 2006) "Structural Basis for the Exceptional in Vivo Efficacy of Bisphosphonate Drugs," *ChemMedChem*. 1:267-273.

Rosen et al. (2004) "Zoledronic Acid is Superior to Pamidronate for the Treatment of Bone Metastases in Breast Carcinoma Patients with at Least one Osteolytic Lesion," *Cancer* 100:36-43.

Russell et al. (Apr. 2006) "Bisphosphonates—From Bench to Bedside," *Ann. NY Acad. Sci* 1068:367-401.

Saiki et al. (Nov. 2005) "Characterization of Solanesyl and Decaprenyl Diphosphate Synthases in Mice and Humans," *FEBS J*. 272:5606-5622.

Salomo et al. (2003) "How Myeloma Cells Escape Bisphosphonate-Mediated Killing: Development of Specific Resistance with Preserved Sensitivity to Conventional Chemotherapeutics," *Br. J. Haematol*. 122:202-210.

Sambrook et al. (2004) "Alendronate Produces Greater Effects than Raloxifene on Bone Density and Bone Turnover in Postmenopausal Women with Low Bone Density: Results of EFFECT (Efficacy of FOSAMAX versus EVISTA Comparison Trial)," *Int. J. Intern. Med*. 255:503-511.

Sanders et al. (Nov. 20, 2003) "3-D QSAR Investigations of the Inhibition of Leishmania Major Farnesyl Pyrophosphate Synthase by Bisphosphonates," *J. Med. Chem*. 46:5171-5183 (Including for CAS 140:22647).

Sanders et al. (2004) "Quantitative Structure-Activity relationships for Gammadelta T Cell Activation by Bisphosphonates," *J. Med. Chem*. 47:375-384.

Sanders et al. (Apr. 21, 2005) "Pyridinium-1-yl Bisphosphonates are Potent Inhibitors of Farnesyl Diphosphate Synthase and Bone Resorption," *J. Med. Chem*. 48:2957-2963.

Santini et al. (Jun. 2006) "Mechanisms of Disease: Preclinical Reports of Antineoplastic Synergistic Action of Bisphosphonates," *Nat. Clin. Pract. Oncol*. 3:325-338.

Segawa et al. (Apr. 2005) "The Anti-Leukemic Efficacy of the Third Generation Bisphosphonate ONO5920/YM529," *Leuk. Res*. 29(4):451-457.

Sheldrake et al. (1997) "SHELXL: High Resolution Refinement," *Methods Enzymol*. 277:319-343.

Song et al. (2004) "Synthesis of Choral Phosphoantigens and Their Activity in γ δT Cell Stimulation," *Bioorg. Med. Chem. Lett*. 14(17):4471-4477.

Swanson et al. (Feb. 2006) "Anti-Cancer Therapy: Targeting the Mevalonate Pathway," *Curr. Cancer Drug Targets* 6(1):15-37.

Szabo et al. (May 23, 2002) "Inhibition of Geranylgeranyl Diphosphate Synthase by Bisphosphonates and Diphosphates: A Potential Route to New Bone Antiresorption and Antiparasitic Agents," *J. Med. Chem*. 45(11):2185-2196.

Tanaka et al. (May 1995) "Natural and Synthetic Non-Peptide Antigens Recognized by Human γ δ T Cells," *Nature* 375:155-158.

Thompson et al. (Feb. 2004) "Statins Prevent Bisphosphonate-Induces Gammadelta-T-Cell Proliferation and Activation in Vitro," *J. Bone Miner. Res*. 19:278-288.

Tripathy et al. (Dec. 2004) "Review of Ibandronate in the Treatment of Metastatic Bone Disease: Experience from Phase III Trials," *Clin. Ther*. 26(12):1947-1959.

van Beek et al. (1999) "Farnesyl Pyrophosphate Synthase is the Molecular Target of Nitrogen-Containing Bisphosphonates," *Biochem. Biophys. Res. Commun*. 264:108-111.

van Beek et al. (1999) "Nitrogen-Containing Bisphosphanates Inhibit Isopentenyl Pyrophosphate Isomerase/farnesyl Pyrophosphate Synthase Activity with Relative Potencies Corresponding to their Antiresorptive Potencies in Vitro and in Vivo," *Biochem. Biophys. Res. Commun*. 255:491-494.

van Beek et al. (2003) "Differentiating the Mechanisms of Antiresorptive Action of Nitrogen Containing Bisphosphonates," *Bone* 33:805-811.

van Beek (1999) "The Role of Geranylgeranylation in Bone Resorption and its Suppression by Bisphosphonates in Fetal Bone Explants in Vitro: A Clue to the Mechanism of Action of Nitrogen-Containing Bisphosphanates," *J. Bone Miner. Res*. 14:722-729.

Vasireddy et al. (2003) "Patterns of Pain in Paget's Disease of Bone and their Outcomes on Treatment with Pamidronate," *Clin. Rheumatol*. 22:376-380.

Vepsalainen, J.J. (1999) "Bisphosphonate Prodrugs: A New Synthetic Strategy to Tetraacyloxymethyl Esters of Methylenebisphosphonates," *Tetrahedron Lett.* 40:8491-8493.

Wakchoure et al. (May 1, 2006) "Bisphosphonates Inhibit the Growth of Mesothelioma Cells In Vitro and In Vivo," *Clin. Cancer Res.* 12:2862-2868.

Wang et al. (2001) "Antibacterial Effect of Human Vgamma2Vdelta2 T Cells in Vivo," *J. Clin. Invest.* 108:1349-1357.

Weizman et al. (1999) "Pharmacological Interaction of the Calcium Channel Blockers Verapamil and Flunarizine with the Opiod System," *Brain Res.* 818:187-195.

Widler et al. (Aug. 15, 2002) "Highly Potent Geminal Bisphosphonates. From Pamidronate Disodium (Aredia) to Zoledronic Acid (Zometa)," *J. Med. Chem.* 45(17):3721-3738.

Wiemer et al. (Feb. 23, 2007) "Digeranyl Bisphosphonate Inhibits Geranylgeranyl Pyrophosphate Synthase," *Biochem. Biophys. Res. Commun.* 353(4):921-925.

Wildman et al. (1999) "Prediction of Physicochemical Parameters by Aromic Contributions," *J. Chem. Info. Comp. Sci.* 39:868-873.

Wilhelm et al. (Jul. 1, 2003) "γδ T Cells for Immune Therapy of Patients with Lymphoid Malignancies," *Blood* 102:200-206.

Yamagishi et al. (Dec. 2004) "Minodronate, A Newly Developed Nitrogen-Containing Bisphosphonate, Suppresses Melanoma Growth and Improves Survival in Nude Mice by Blocking Vascular Endothelial Growth Factor Signaling," *Am. J. Pathol.* 165:1865-1874.

Yardley et al. (Mar. 2002) "In Vivo Activities of Farnesyl Pyrophosphate Synthase Inhibitors Against *Leishmania donovani* and *Toxoplasma gonsii*," *Antimicrob. Agents Chemother.* 46:929-931.

Yin et al. (Mar. 2006) "Enthalpy Versus Entropy-Driven Binding of Bisphosphonates to Farnesyl Diphosphate Synthase," *J. Am. Chem. Soc.* 128:3524-3525.

Zhang et al. (2006) "[2-(Dimethylsulfonio)-1-hydroxy-1-phosphonoethyl]Phosphonate Monohydrate," *Acta Cryst.* E62:o1006-o1008.

Zhang et al. (Nov. 29, 2007) "Activity of Sulfonium Bisphosphonates on Tumor Cell Lines," *J. Med. Chem.* 50(24):6067-6079.

Zhang et al. (Sep. 21, 2006) "Activity of Nitrogen-Containing and Non-Nitrogen-Containing Bisphosphonates on Tumor Cell Lines," *J. Med. Chem.* 49(19):5804-5814.

Zhang et al. (2000) "A Novel and Practical Synthesis of 3-unsubstituted Indolizines," *Synthesis* :1733-1737.

Zhu et al. (2001) "3-D QSAR Analyses of Novel Tyrosine Kinase Inhibitors Based on Phamacophore Alignment," *J. Chem. Inf. Comput. Sci.* 41(4):1032-1040.

Alfer'ev et al. (1987) "Reactions of Vinylidenediphosphonic Acid with Nucleophiles. 3. Addition of Thiols," *Russian Chem. Bull.* 36(4):786-790.

Alfer'ev et al. (1984) "New Bifunctional Reagents for the Study of Cytochrome P450 Active Center Localization in Microsomal Membrane," *Doklady Akademii Nauk SSSR* 277(2):371-374 Abstract Only.

Gossman et al. (2003) "Three Hydrates of the Bisphosphonate Risedronate, Consisting of One Molecular and Two Ionic Structures," *Acta Crystallographica Section C* (Crystal Structure Comm.) C59:m33-m36.

Gossman et al. (2002) "Monosodium [1-hydroxy-2-(1H-imidazol-3-ium-4-yl)ethane-1,1-diyl]-bis(phosphonate) tetrahydrate (monosodium isozoledronate)," *Acta Crystallographica Section C* (Crystal Structure Comm.) C58:m599-m600.

Hutchinson et al. (1988) "Michael Addition Reactions of ethylidenebisphosphonates," *J. Organometall. Chem.* 346(3):341-348.

Krainev et al. (1992) "Effect of Mutations at Lys250, Arg251, and Lys253 of Cytochrome P450 1A2 on the Catalytic Activities and the Bindings of Bifunctional Axial Ligands," *Arch. Biochem. Biophy.* 298(1):198-203.

Krainev et al. (1988) "Use of Bifunctional Compounds for Studying the Active Center Location of Cytochrome P450 in a Microsomal Membrane," *Biologicheskie Membrany* 5(8):795-806 Abstract Only.

Krainev et al. (1988) "Localization of the Active Center of Microsomal Cytochrome P-450," *Biochem Biophy. Research Comm.* 150(1):426-35.

Krainev et al. (1985) "Bifunctional Compound Study of the Active Center Location of Cytochrome P-450 in a Microsomal Membrane ('float' molecules method)," *Biochimica Biophysica Acta Biomembranes* 818(1):96-104.

Van Brussel et al. (2003) "Hydronium (cycloheptylammonio)-methylene-1, 1-bisphosphonate (hydronium incadronate)," *Acta Crystallographica Section C* (Crystal Structure Comm.) C59:o93-o94.

Zhang et al. (Mar. 2009) "Lipophilic Bisphosphonates as Dual Farnesyl/Geranylgeranyl Diphosphate Synthase Inhibitors: An X-ray and NMR Investigation," *J. Amer. Chem. Soc.* 131:5153-5162.

International Preliminary Report on Patentability, Corresponding to International Application No. PCT/US2008/060051, Mailed Oct. 22, 2009.

Clezardin P. et al. (Jun. 15, 2005) "Bisphosphonates and Cancer-Induced Bone Disease: Beyond their Antiresorptive Activity" Cancer Research 65:4971-4974.

Hirabayashi H. et al. (2001) "Relationship between Physiochemical and Osterotropic Properties of Bisphosphonic Derivatives: Rational Design for Osteotropic Drug Delivery System (ODDS)" Pharma Research 18(5) 646-651.

Mukkamala D. et al. (Nov. 2008) "Bisphosphonate Inhibition of a *Plasmodium* Farnesyl Diphosphate Synthase and a General Method for Predicting Cell-based Activity form Enzyme Data" J. Med. Chem. 51(24):7827-7833.

Senaratne S.G. et al. (2000) "Bisphosphonates induce apoptosis in human breast cancer cell lines" British J. Cancer 82(8):1459-1468.

Shipman C.M. et al. (1997) "Bisphosphonates Induce Apoptosis in Human Myeloma Cell Lines: A Novel Anti-tumor Activity" British J. Haematol. 98(3):665-672.

Sousa S.F. et al. (2008)"Farnesyltransferase inhibitors: a detailed chemical view on an elusive biological problem" Curr. Med. Chem. 15(15):1478-1492.

Benaim G. et al. (Web Release Jan. 5, 2006) "Amiodarone has Intrinsic Anti-*Trypanosoma cruzi* Activity and Acts Synergistically with Posaconazole." J. Med. Chem. 49:892-899.

Cheng F., Oldfield, E.. (Web Release Sep. 10, 2004) "Inhibition of Isoprene Biosynthesis Pathway Enzymes by Phosphonates, Bisphosphonates and Diphosphates." J. Med. Chem. 47:5149-5158.

Croft S. L. et al. (Web Release Sep. 8, 2005) "Chemotherapy of trypanosomiases and leishmaniasis." TRENDS in Parasitology 21(11):508-512.

Das H. et al. (Sep. 2001) "Vgamma2Vdelta2 T-cell receptor—mediated recognition of aminobisphosphonates." Blood 98(5):1616-1618.

Geddes A.D. et al. (1994) Bisphosphonates: structure-activity relationship and therapeutic implications. In *Bone and Mineral Research* vol. 8: 265-306, Elsevier Science Publications.

Gossman W, Oldfield E. (Web Release Sep. 19. 2002) "Quantitative Structure-Activity Relations for gamma-delta T Cell Activation by Phosphoantigens." J. Med. Chem 45:4868-4874.

Gottlin, E. et al. (2003) "High-Throughput Screen for Inhibitors of 1-Deoxy-D-Xylulose 5-Phosphate Reductoisomerase by Surrogate Ligand Competition." J. Biomolecular Oncol. 44(6):644-650.

Wigington D.P.et al. (2005) "Pamidronate and 1,24(S)-dihydroxyvitamin $D_2$ synergistically inhibit the growth of myeloma, breast and prostate cancer cells." Anticancer Research May-Jun.: 25(3B):1909-1917.

Wouters J. et al. (Web Release Dec. 23, 2004) "A Crystallographic Investigation of Phosphoantigen Binding to Isopentenyl Pyrophosphate/Dimethylallyl Pyrophosphate Isomerase." J. Amer. Chem. Soc. 127(2):536-537.

Yajima, S. et al. (Web Release Aug. 14, 2004) "Crystallographic Structures of Two Bisphosphonate:1-Deoxyxylulose-5-Phosphate Reductoisomerase Complexes " J. Amer. Chem. Soc. 126(35):10824-10825.

Zhang Y. et al. (2010) "Lipophilic Pyridinium Bisphosphonates: Potent γδT Cell Stimulators." Angew. Chem. Int. Ed. 49:1136-1138.

Zhang y. et al. (Sep. 2006) "Structural Studies of Vγ2Vδ2 T Cell Phosphoantigens." Chem. & Biol. Screening13:985-992. 8(3):332-339.

Hudock M.P. et al. (Web Release Dec. 10, 2005) "Inhibition of *Trypanosoma cruzi* Hexokinase by Bisphosphonates." *J. Med. Chem.* 49:215-223.

Kunzmann V., Bauer E. and Wilhelm M. (Mar. 4, 1999) "γ/δ T-cell stimulation by pamidronate." *N. Eng. J. Med.* 340:737-738.

Li, H et al. (2003) "The Effect of Triton Concentration on the Activity of Undecaprenyl Pyrophosphate Synthase Inhibitors." *J. Biomolecular Screening* 8(6):712-715.

Parniak M.A. et al. (2004) "Bisphosphonate Inhibitors of Nucleoside Reverse Transcriptase Inhibitor Excision." Abstract 26. In Antiviral Therapy 9:S32, presented at the XIII Int'l HIV Drug Resistance Workshop: Basic Principles & Clinical Implications (Jun. 8-12, 2004) (Tenerife, Canary Islands, Spain).

Parniak M.A. et al. (2003) "*Inhibitors of* NTRI *Excision*." Abstract 27, Program Abstr HIV DRP Symp. Antivir Drug Resist. Dec. 7-10, 2003; HIV DRP Symposium Antiviral Drug Resistance (Chantilly, VA).

Pink R. et al. (Sep. 2005) "Opportunities and challenges in antiparasitic drug discovery." *Nat. Rev. Drug Discovery* 4(9):727-740.

Segawa H. et al. (Aug. 2005) "Zoledronate synergies with imatinib mesylate to inhibit Ph+ primary leukaemic cell growth." *Br. J. Haemotol.* 130(4):558-560.

Song Y. et al. (2008) "Bisphosphonate inhibitors of ATP-mediated HIV-1 reverse transcriptase catalyzed excision of chain-terminating 30-azido, 30-deoxythymidine: A QSAR investigation." *Biorganic & Medicinal Chem.* 16:8959-8967.

Szabo C.M., Oldfield E. (2001) "An Investigation of Bisphosphonate Inhibition of a Vacuolar Proton-Pumping Pyrophosphatase." *Biochem. Biophys. Res. Comm.* 287(2):468-473.

Szajnman S.H. et al. (Web Release Sep. 6, 2005) "Synthesis and biological evaluation of 1-amino-1,1-bisphosphonates derived from fatty acids against *Trypanosoma cruzi* targeting farnesyl pyrophosphate synthase." *Bioorg. Med. Chem. Lett.* 15:4685-4690.

Thompson K. et al. (2002) "Identification of a Bisphosphonate That Inhibits Isopentenyl Diphosphate Isomerase and Farnesyl Diphosphate Synthase." *Biochem. Biophys. Res. Comm.* 290(2):869-873.

Thompson K., Rogers, M.J. "Statins Prevent Bisphosphonate-Induced gamma,delta-T-Cell Proliferation and Activation In Vitro." *J. Bone and Mineral Research* 19(2):278-288, 2004.

Thompson K., Gordon S.A., Rogers M.J.(2002) "N-Bisphosphonates Stimulate Proliferation of γ/δ-T Cells in Human PBMC Cultures by Inhibiting the Mevalonate Pathway: Clarification of the Acute Phase Response." *J. Bone Mineral Res.* 17:F29, Abstract.

Ullen A. et al. (2005) "Additive/synergistic antitumoral effects on prostate cancer cells in vitro following treatment with a combination of docetaxel and zoledronic acid."*Acta.*

\* cited by examiner

BISPHOSPHONATE COMPOUNDS AND METHODS WITH ENHANCED POTENCY FOR MULTIPLE TARGETS INCLUDING FPPS, GGPPS, AND DPPS

CROSS-REFERENCES TO RELATED APPLICATIONS

This application is a nonprovisional application of U.S. provisional application Ser. No. 60/911,426 filed Apr. 12, 2007; and a continuation-in-part of U.S. application Ser. No. 11/687,570 filed Mar. 16, 2007 and international application number PCT/US07/64239 filed Mar. 16, 2007, each of which are nonprovisional applications of U.S. provisional application Ser. No. 60/783,491 filed Mar. 17, 2006; and a continuation-in-part of U.S. application Ser. No. 11/245,612 filed Oct. 7, 2005 and international application number PCT/US05/36425 filed Oct. 7, 2005, each of which are nonprovisional applications of U.S. provisional application Ser. No. 60/617,108 filed Oct. 8, 2004; all of which are hereby incorporated by reference to the extent not inconsistent with the disclosure herewith. This application hereby claims benefit of priority to the above-referenced applications.

STATEMENT REGARDING FEDERALLY SPONSORED RESEARCH OR DEVELOPMENT

This invention was made with government support under NIH Grant Nos. NIH GM50694, GM65307, GM73216, and AI-060452 awarded by the National Institutes of Health. The government has certain rights in the invention.

BACKGROUND OF THE INVENTION

Earlier generation compounds of nitrogen-containing bisphosphonates such as pamidronate (Aredia®), alendronate (Fosamax®), risedronate (Actonel®), zoledronate (Zometa®), and ibandronate (Boniva) represent drugs currently used to treat conditions such as osteoporosis, Paget's disease and hypercalcemia due to malignancy. These compounds function primarily by inhibiting the enzyme farnesyl diphosphate synthase (FPPS), resulting in decreased levels of protein prenylation in osteoclasts. Certain bisphosphonates have also been found to have anti-parasitic activity and to stimulate human γδ T cells, and with these earlier generation compounds there has been interest in cancer-related applications. There is a continued need, however, for the further development of alternative compounds and methods of use including therapeutic applications. There remains a need for alternative compounds and methods, including in particular compounds having improved properties such as greater activity and/or other advantageous functionality.

The mevalonate pathway, also referred to as the HMG-CoA reductase pathway, or mevalonate-dependent (MAD) route, is an important cellular metabolic pathway present in higher eukaryotes and many bacteria. This pathway contributes to the production of dimethylallyl pyrophosphate (DMAPP) and isopentenyl pyrophosphate (IPP) that serve as the basis for the biosynthesis of molecules used in processes as diverse as protein prenylation, cell membrane maintenance, hormones, protein anchoring and N-glycosylation. The ability to inhibit a single molecule in such a pathway can provide an option for the modification of function and one or more outputs of the pathway. The ability to interact with multiple molecular targets of such a fundamentally important pathway, however, can provide opportunities for greater levels of modification. For example, the ability to simultaneously knock out a pipeline at several points can dramatically diminish the impact of the pipeline's flow and/or yield of products.

In embodiments of the invention herein, we disclose important discoveries regarding compounds and methods in connection with the inhibition of molecular targets including FPPS, geranylgeranyl pyrophosphate synthase (GGPPS), and decaprenyl pyrophosphate synthase (DPPS).

In certain embodiments, compounds of the invention include bisphosphonates that are capable of selectively inhibiting one or more of FPPS, GGPPS, and DPPS. In preferred embodiments, compounds of the invention are capable of selectively inhibiting two or more of FPPS, GGPPS, and DPPS. In embodiments, compounds and methods of the invention demonstrate superior activity levels, such as in the anti-cancer context, which in several cases exceed the activity levels of previous generation bisphosphonate drugs by orders of magnitude. The invention disclosed herein thus represents a major advance in the development of useful agents which in certain embodiments are compounds capable of demonstrating high potency levels.

SUMMARY OF THE INVENTION

The invention provides, inter alia, novel bisphosphonate compounds and methods of making and using the compounds. In embodiments, the invention provides compounds and methods in connection with research and therapeutic applications, e.g., for tumor cell growth inhibition, activation of gammadelta T cells, inhibition of farnesyldiphosphate (FPPS), GGPPS, and/or DPPS enzymes, and for treatment of bone resorption diseases, cancer, immune disorders, immunotherapy, and infectious diseases. In regard to certain embodiments, it has been recognized that certain structural features significantly enhance the activity of the compounds. Certain compounds are disclosed with structural features that correlate with useful and in certain embodiments high activity levels in functionally relevant contexts. For example, in specific embodiments the presence of particular alkoxy substituents on a ring component in an organic bisphosphonate compound contribute to desirable functional activity. Further variations are also provided.

Structural features of compounds have been identified which correlate with functional properties and activities. In embodiments, compounds of the invention are capable of demonstrating profound activity levels, for example in inhibiting tumor cell growth inhibition and immunostimulation. Compounds having such features have been synthesized and tested. This testing has allowed the further identification and development, for example, of a first class of compounds with significant anti-cancer and immunostimulatory ability and a second class of compounds with anti-cancer ability, but without substantial immunostimulatory capability.

In an embodiment, compounds of the invention can provide advantages such as desirable activity, improved activity and/or therapeutic effect, reduced toxic effect, and/or such therapeutic and/or toxic effect with a more advantageous administration profile. In an embodiment, the more advantageous administration profile can involve one or more of lowered individual and/or total dosage amount; less frequent dosing regime; etc. In an embodiment, one or more of such advantages or qualities is capable of being determine in relation to another bisphosphonate compound, for example by comparison with a previous generation compound such as an approved drug.

In embodiments, bisphosphonate compounds of the invention can demonstrate activity in one or more contexts, including a farnesyl diphosphate synthase (FPPS) assay, a GGPPS assay, a DPPS assay, a *D. discoideum* growth inhibition assay, a T cell activation assay, a bone resorption assay, the treatment of infectious disease, the treatment of a bone resorption clinical disorder, an immunotherapeutic treatment, the treatment of cancer, the treatment of bone pain, stimulation of an immune cell and/or system, and inhibition of growth of a cancer cell or tumor.

The invention broadly provides bisphosphonate compounds and related methods of making and using. In embodiments, the invention specifically provides organic bisphosphonate compounds and/or pharmaceutically acceptable salts or esters thereof. In further embodiments, the invention specifically provides other variations of bisphosphonate compounds. In embodiments, functionally and/or therapeutically active bisphosphonates of this invention have general and specific structures as described herein.

In embodiments, the present invention provides compounds of bisphosphonates and pharmaceutical compositions comprising one or more bisphosphonates. In preferred embodiments, the bisphosphonates are high potency bisphosphonates in one or more functional contexts.

In embodiments, the invention provides compounds of formula XA1:

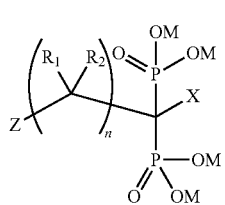

XA1 or salts or hydrates thereof, wherein;

X is hydrogen, hydroxyl group, or a halogen;

M, independently of other M in the compound, are a negative charge, a hydrogen, alkyl group, $-(CH_2)_p-O-CO-R$ or $-(CH_2)_p-O-CO-O-R$, where p is 1 to 6, and R is hydrogen, optionally substituted alkyl or optionally substituted aryl; $-OM$ can also be a salt of form $-O^-A^+$, where $A^+$ is a cation;

n is 1, 2, or 3:

each $R_1$ and $R_2$, independently of each other, are selected from the group consisting of a hydrogen, a halogen, $-N(R')_2$, $-SR'$, $OR'$, an optionally substituted alkyl, an optionally substituted alkenyl, and an optionally substituted aryl group, where each R', independent of any other R' in any listed group, is selected from H, an optionally substituted alkyl group and an optionally substituted aryl group, and one of $R_1$ and one of $R_2$ together may form a 3-10 member carbocyclic or heterocyclic ring containing one to three heteroatoms, particularly N, S, and O;

Z is 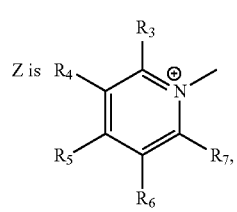 Z1

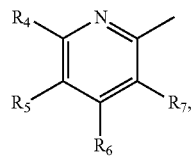 Z2

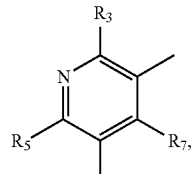 Z3

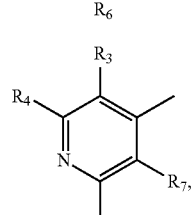 Z4

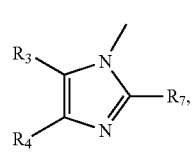 Z5

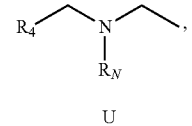 Z6

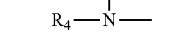 Z7

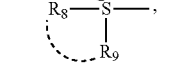 Z8

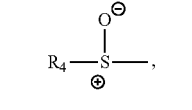 Z9

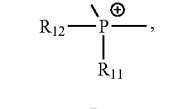 Z10

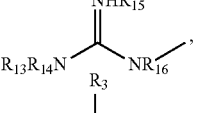 Z11

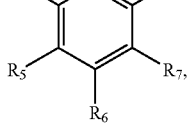 Z12 wherein U is H or OH;

$R_3$-$R_7$ if present, independently of one another, are selected from the group consisting of a hydrogen, a halogen, a $-CN$, —OR''', —COOR''', —OCOOR''', —COR''', —CON(R''')$_2$, —OCON(R''')$_2$, —N(R''')$_2$, —NO$_2$, —SR, —SO$_2$R, —SO$_2$N(R''')$_2$ or —SOR''' group, an optionally substituted alkyl group, an optionally substituted alkenyl group, an optionally substituted alkynyl group and an optionally substituted aryl group, where each R or R''', is independently selected from H, an optionally substituted alkyl group, an optionally substituted aryl group, and an optionally substituted acyl group;

wherein at least one of $R_3$-$R_7$, if present is RL and when Z is Z6, $R_4$, is RL where RL is a group selected from alkyl, alkoxy, alkenyl, alkynyl, alkenoxy or alkynoxy groups having 6 to 20 carbon atoms, each of which are optionally substituted; alkyl ether groups which are alkyl groups having 6-20 carbon atoms in which one or more non-adjacent carbon atoms are replaced with an O; or a 3-$R_M$ or 4-$R_M$ substituted phenyl group, where $R_M$ is selected from alkyl, alkenyl, alkynyl, alkoxy, alkenyoxy, alkynoxy or alkyl ether groups having 3-15 carbon atoms, where the other ring positions of the phenyl ring are optionally substituted with one or more halogens, or one or more optionally substituted alkyl groups having 1-3 carbon atoms;

$R_N$ is an optionally substituted alkyl group having 1-3 carbon atoms;

$R_8$, $R_{10}$ and $R_{13}$, if present, are groups selected from alkyl groups having 6-20 carbon atoms; alkenyl or alkynyl groups having 6 to 20 carbon atoms; alkyl ether groups which are alkyl groups having 6-20 carbon atoms in which one or more non-adjacent carbon atoms are replaced with an O; or 3-$R_M$ or 4-$R_M$ substituted phenyl groups, where $R_M$ is selected from alkyl, alkenyl, alkynyl, alkoxy, alkenyoxy, alkynoxy or alkyl ether groups having 3-15 carbon atoms, where the other ring positions of the phenyl ring are optionally substituted with one or more halogens, or one or more optionally substituted alkyl groups having 1-3 carbon atoms;

$R_9$, $R_{11}$ and $R_{12}$, if present, are groups selected from alkyl, alkenyl or alkynyl groups having 1-6 carbon atoms; alkyl ether groups which are alkyl groups having 1-6 carbon atoms in which one or more non-adjacent carbon atoms are replaced with an O; or optionally substituted phenyl groups;

$R_{14}$, $R_{15}$, $R_{16}$, if present, are independently selected from hydrogen or optionally substituted alkyl having 1-6 carbon atoms or optionally substituted aryl groups; wherein $R_9$ can be linked to the first carbon of $R_8$ to form a 5-8 member carbon ring which may be saturated or carry one or two double bonds;

wherein optional substitution most generally means substitution of one or more carbons of the listed optionally substituted groups with non-hydrogen substituents selected from the groups consisting of one or more halogens, one or more cyano, one or more alkyl, haloalkyl, or hydroxyalkyl groups having 1-3 carbon atoms, one or more alkenyl, haloalkenyl or hydroxyalkenyl groups having 1-4 carbon atoms; one or more alkynyl groups having 1-4 carbon atoms, one or more acyl or haloacyl groups; or one or more groups selected from a —ORs, —COORs, —OCOORs, —CORs, —CON(Rs)$_2$, —OCON(Rs)$_2$, —N(Rs)$_2$, —NO$_2$, —SRs, —SO$_2$Rs, —SO$_2$N(Rs)$_2$ or —SORs group, where Rs is hydrogen, an alkyl group having 1-6 carbon atoms, optionally substituted with one or more halogens, hydroxyl groups, amino groups or alkyl amino groups, or an aryl group and an aryl group optionally substituted with one or more alkyl groups, haloalkyl groups, halogens, hydroxyl groups, amino groups, alkyl amino groups, acyl groups or haloacyl groups.

In specific embodiments: Z is any one of Z1-Z5; Z is Z6; Z is Z7; Z is Z9; Z is Z8 or Z10; Z is Z11 or Z is Z12. In specific embodiments: when Z is Z1, $R_4$ is RL; when Z is Z1, $R_5$ is RL; when Z is Z1, $R_6$ is RL; when Z is Z2, $R_4$ is RL; when Z is Z2, $R_5$ is RL; when Z is Z2, $R_6$ is RL; when Z is Z3, $R_5$ is RL; when Z is Z3, $R_6$ is RL; when Z is Z4, $R_4$ is RL; when Z is Z4, $R_6$ is RL; when Z is Z5, $R_3$ is RL; when Z is Z5, $R_4$ is RL; when Z is Z12, $R_4$ is RL; or when Z is Z12, $R_5$ is RL.

In specific embodiments, RL is a group selected from alkyl, alkenyl or alkynyl groups having 7-20 carbon atoms or alkoxy groups having 7-20 carbon atoms.

In specific embodiments, RL is a group selected from alkyl or alkynyl groups having 7-20 carbon atoms or alkoxy groups having 7-20 carbon atoms. In other embodiments, RL is a group selected from alkyl, or alkynyl groups having 7-14 carbon atoms or 8-12 carbon atoms. In other embodiments, RL is an alkoxy group having 7-14 carbon atoms or 8-12 carbon atoms.

In specific embodiments, RL is a straight-chain alkyl or alkoxy group having from 7 to 20 carbons atoms or 7 to 12 carbon atoms. In specific embodiments, in which Z is Z1-Z5, RL is a straight-chain alkyl or alkoxy group having from 7 to 20 carbons atoms. In specific embodiments, in which Z is Z1-Z5, RL is a straight-chain alkyl or alkoxy group having from 7 to 10 carbons atoms. In specific embodiments, where Z is Z1-Z4, RL is a straight-chain alkyl or alkoxy group having from 7 to 10 carbons atoms. In specific embodiments, where Z is Z1-Z2 or Z4, $R_4$ is RL and RL is a straight-chain alkyl or alkoxy group having from 6 to 10 carbons atoms or 7-10 carbon atoms. In specific embodiments, where Z is Z1, $R_4$ is RL and RL is a straight-chain alkyl or alkoxy group having from 7 to 10 carbon atoms. In specific embodiments, where Z is Z1, $R_4$ is RL and RL is a straight-chain alkoxy group having from 6 to 20 carbon atoms. In specific embodiments, where Z is Z1, $R_4$ is RL and RL is a straight-chain alkoxy group having from 7 to 10 carbon atoms.

In specific embodiments, where Z is Z8 or Z10 and $R_8$ or $R_{10}$, respectively, is an alkyl group having 8-20 carbon atoms. In specific embodiments, where Z is Z8 or Z10, $R_8$ or $R_{10}$, respectively, is an alkyl group having 9-17 carbon atoms. In specific embodiments, where Z is Z8 or Z10, $R_8$ or $R_{10}$, respectively, is a straight-chain alkyl group having 8-20 carbon atoms or a straight-chain alkyl group having 9-17 carbon atoms. In specific embodiments, Z is Z8 and $R_8$ is an alkyl group having 8-20 carbon atoms. In specific embodiments, Z is Z8 and $R_8$ is a straight-chain alkyl group having 8-20 carbon atoms. In specific embodiments, Z is Z8 and $R_8$ is a straight-chain alkyl group having 9-17 carbon atoms.

In specific embodiments, Z is Z1-Z5 and RL is an alkynyl group —C≡C—$R_{AK}$ where $R_{AK}$ is a straight-chain alkyl group having 4-20 carbon atoms or 5-10 carbon atoms. In specific embodiments, Z is Z1-Z4 and RL is an alkynyl group —C≡C—$R_{AK}$ where $R_{AK}$ is a straight-chain alkyl group having 4-20 carbon atoms or 5-10 carbon atoms. In specific embodiments, Z is Z1-Z2 or Z4, $R_4$ is RL and RL is an alkynyl group —C≡C—$R_{AK}$ where $R_{AK}$ is a straight-chain alkyl group having 4-20 carbon atoms or 5-10 carbon atoms. In specific embodiments, Z is Z1, $R_4$ is RL and RL is an alkynyl group —C≡C—$R_{AK}$ where $R_{AK}$ is a straight-chain alkyl group having 4-20 carbon atoms or 5-10 carbon atoms.

In specific embodiments, RL are alkyl ether groups which are alkyl groups having 7-20 carbon atoms or 7-14 carbon atoms n which one or more non-adjacent carbon atoms are replaced with an O.

In specific embodiments, RL is a 3-$R_M$ or 4-$R_M$ substituted phenyl group, where $R_M$ is selected from alkyl, alkenyl, alkynyl, alkoxy, alkenyoxy, alkynoxy or alkyl ether groups having 3-15 carbon atoms or 6-12 carbon atoms, where the other ring positions of the phenyl ring are optionally substituted with one or more halogens, or one or more optionally substituted alkyl groups having 1-3 carbon atoms.

In specific embodiments, one or more alkyl groups herein are optionally substituted with one or more halogens. In other embodiments, aryl groups herein are phenyl groups optionally substituted with one or more halogens, or one or more alkyl groups having 1-3 carbon atoms.

In specific embodiments, $R_{13}$ is a group selected from alkyl, or alkynyl groups having 7-20 carbon atoms; or an alkyl ether groups which are alkyl groups having 7-20 carbon atoms in which one or more non-adjacent carbon atoms are replaced with an O;

In specific embodiments, $R_{13}$ is a group selected from alkyl, or alkynyl groups having 7-20 carbon atoms or 9-17 carbon atoms;

In specific embodiments, when Z is Z12, RL is $R_4$ or $R_5$ and RL is an optionally substituted alkyl, or alkoxy group having 7-20 carbon atoms or an alkynyl group having 6 to 20 carbon atoms. In other embodiments, when Z is Z12, RL is an unsubstituted alkyl or alkoxy group having 7-20 carbon atoms. In additional embodiments, the alkyl group is a straight-chain alkyl group or the alkyl of the alkoxy group is a straight-chain alkyl group. In other specific embodiments, $R_4$ is RL. In other embodiments, the alkyl or alkoxyl group has 7-17 carbon atoms. In other embodiments, the alkyl or alkoxy group has 8-12 carbon atoms. In specific embodiments, Z is Z12, and RL is an alkynyl group —C≡C—$R_{AK}$ where $R_{AK}$ is a straight-chain alkyl group having 4-20 carbon atoms or 5-10 carbon atoms.

In specific embodiments, when Z is Z12, RL is a substituted aryl, preferably phenyl; and more particularly RL is a sulfonamide substituted phenyl or is a naphthyl sulfonamide substituted phenyl.

In a preferred embodiment, when M is a salt the cation $A^+$ is a pharmaceutically acceptable cation.

In each of the above listed specific embodiments, the following additional specific embodiments are included:

$R_3$-$R_7$, if present, which are not RL are selected from the group consisting of a hydrogen, a halogen, an optionally substituted alkyl group, an optionally substituted alkenyl group, an optionally substituted alkynyl group, an optionally substituted alkoxy group, and an optionally substituted aryl group;

$R_3$-$R_7$, if present, which are not RL are hydrogens, halogens or unsubstituted alkyl groups having 1-3 carbon atoms;

$R_3$-$R_7$, if present, which are not RL are hydrogens;

each $R_9$, if present, is an alkyl group having 1-6 carbon atoms;

each $R_9$, if present, is an alkyl group having 1-4 carbon atoms;

each $R_9$, if present, is an alkyl group having 1-3 carbon atoms;

each $R_9$, if present is a methyl group;

$R_{11}$ or $R_{12}$, if present, are the same groups;

$R_{11}$ or $R_{12}$, if present, are different groups;

$R_{11}$ or $R_{12}$, if present, are alkyl groups having 1-6 carbon atoms;

$R_{11}$ or $R_{12}$, if present, are alkyl groups having 1-4 carbon atoms;

$R_{11}$ or $R_{12}$, if present, are alkyl groups having 1-3 carbon atoms;

$R_{11}$ or $R_{12}$, if present, are methyl groups;

$R_{14}$ and $R_{15}$, if present, are hydrogens;

$R_{15}$ and $R_{16}$, if present, are hydrogens;

$R_{15}$ and $R_{16}$, if present, are hydrogens and $R_{14}$ is hydrogen or an alkyl group having 1-3 carbon atoms;

$R_N$ is a methyl group; or $R_4$ is a straight-chain alkyl group having from 6-20 carbon atoms or 7-17 carbon atoms or 8-15 carbon atoms.

In other specific embodiments, high potency bisphosphonates include those of formula XA1 wherein Z is Z1A, Z2A, Z2B, Z3A, Z4A, Z5A, Z12A or Z12B:

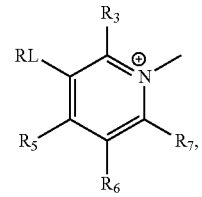

Z1A

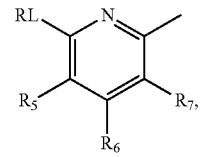

Z2A

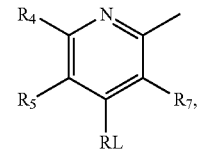

Z2B

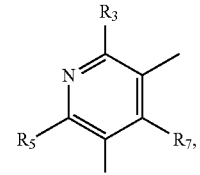

Z3A

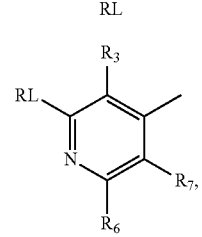

Z4A

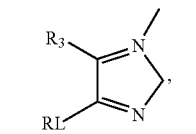

Z5A

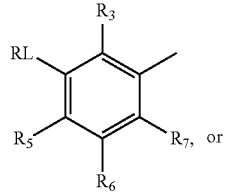

Z12A

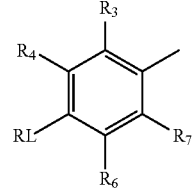

Z12B where variables $R_3$-$R_7$ are not RL, but take all other values as listed above and RL is as defined above including various specific embodiments set forth herein. In specific embodiments of Z1A, Z2A, Z3A, Z4A, or Z5A, $R_3$-$R_7$ are selected from hydrogens, halogens or alkyl groups having 1-3 carbon atoms; or all of $R_3$-$R_7$ are hydrogens. In specific embodiments of Z1A, Z2A, Z3A, Z4A, Z5A, Z12A or Z12B, RL are alkyl or alkoxy groups having 7-20 carbon atoms or 7 to 17 carbon atoms. In specific embodiments of Z1A, Z2A, Z3A, Z4A, or Z5A, RL are straight-chain alkyl or alkoxy groups having 6-20 carbon atoms or 7 to 17 carbon atoms. In other specific embodiments of Z1A, Z2A, Z3A, Z4A, or Z5A, RL are alkynyl groups having from 8-20 carbon atoms or 9 to 17 carbon atoms.

In each of the above listed specific embodiments, the following additional specific embodiments are included:

$R_1$ and $R_2$ are all hydrogens;

n is 1;

n is 2;

X is hydrogen;

X is a hydroxyl group;

X is fluorine;

X is chlorine;

All M are hydrogens;

At least one M is a negative charge and the remaining M are hydrogens;

At least one M is, —$(CH_2)_p$—O—CO—R or —$(CH_2)_p$—CO—R, where p is 1 to 6, and R is hydrogen, optionally substituted alkyl or optionally substituted aryl; or One, or two of —OM are —$O^-A^+$, where $A^+$ is a cation and the remaining M are hydrogens;

Z is one of Z as set forth herein.

In a particular embodiment, the invention provides compounds of formula XA1 wherein Z=Z12 and $R_4$=RL. In a particular embodiment, the invention provides compounds of formula XA1 wherein Z=Z1 and $R_4$=RL.

In an embodiment, the invention provides a compound selected from the group consisting of: 637, 638, 677, 687, 688, 693, 694, 695, 696, 714, 715, 716, 717, 722, 754, 675, 678, and 728; and for each respective said compound, a pharmaceutically acceptable salt or ester thereof. In an embodiment, said compound is also a compound of formula XA1.

In an embodiment, the invention provides a composition comprising a pharmaceutical formulation of a compound of the invention of any formula herein.

In an embodiment, the invention provides a medicament which comprises a therapeutically effective amount of one or more compositions of the invention. In an embodiment, the invention provides a method for making a medicament for treatment of a condition described herein.

In an embodiment, the invention provides a method of inhibiting growth of a cancer cell comprising contacting said cancer cell with an effective amount of a compound of the invention or a pharmaceutical formulation thereof. In an embodiment, the invention provides a method of treating a cancer comprising administering to a patient in need thereof, a therapeutically effective amount of a compound of the invention or a pharmaceutical formulation thereof. In an embodiment, the cancer is a breast cancer. In an embodiment, the breast cancer involves an actual or potential bone metastatic condition. In an embodiment, the cancer is a cancer known in the art.

In an embodiment, the invention provides a method of stimulating a T cell, comprising contacting the T cell with a compound of the invention or a pharmaceutical formulation thereof. In an embodiment, said T cell is a gammadelta T cell. In an embodiment, the invention provides a method of immunotherapeutic treatment comprising administering to a patient in need thereof, a therapeutically effective amount of a compound of the invention or a pharmaceutical formulation thereof.

In an embodiment, the invention provides a method of treating a bone resorption disorder comprising administering to a patient in need thereof, a therapeutically effective amount of a compound of the invention or a pharmaceutical formulation thereof. In an embodiment, the invention provides a method of treating a bone pain condition comprising administering to a patient in need thereof, a therapeutically effective amount of a compound of the invention or a pharmaceutical formulation thereof.

In an embodiment, the invention provides a method of inhibiting growth of an infectious disease agent comprising contacting said infectious disease agent with an effective amount of a compound of the invention or a pharmaceutical formulation thereof. In an embodiment, the invention provides a method of treating an infectious disease comprising administering to a patient in need thereof, a therapeutically effective amount of a compound of the invention or a pharmaceutical formulation thereof. In an embodiment, the infectious disease relates to an agent selected from the group consisting of: a virus, a fungus, a bacterium, and a protozoan parasite. In an embodiment, said virus is a retrovirus. In an embodiment, said retrovirus is human immunodeficiency virus (HIV). In an embodiment, said protozoan parasite is selected from the group consisting of: *Leishmania, Toxoplasma, Cryptosporidium, Plasmodium*, and *Trypanosoma*. In an embodiment, said protozoan parasite is *Leishmania major*. In an embodiment, said bacterium is *Escherichia coli* or *Staphylococcus aureus*.

In an embodiment, the invention provides a method of synthesizing a compound of the invention or a pharmaceutical formulation thereof. In an embodiment, a synthetic scheme is used or adapted from such of U.S. application Ser. No. 11,687,570 filed Mar. 17, 2006; PCT International Application Serial PCT/US07/64239 filed Mar. 17, 2006; U.S. Application Ser. 60/783,491 filed Mar. 17, 2006; U.S. application Ser. No. 11/245,612 filed Oct. 7, 2005 (see also US Patent Application Publication No. 20060079487 published Apr. 13, 2006); U.S. Application Ser. 60/617,108 filed Oct. 8, 2004; PCT International Application No. PCT/US05/036425 filed Oct. 7, 2005 (see also International Publication No. WO/2006/039721 published Apr. 13, 2006); US Patent Application Publication No. 20050113331 published May 26, 2005; and as would be understood in the art.

In an embodiment, the invention provides a method of selectively inhibiting one or more of an FPPS, GGPPS, DDPPS, and a DHDDS enzyme. In an embodiment, the invention provides a method of selectively inhibiting two or more of an FPPS, GGPPS, and a DPPS enzyme, comprising contacting said enzymes or a cell containing said enzymes with an organic compound. In an embodiment, said organic compound is a bisphosphonate compound. In an embodiment, said compound is a compound of formula XA1 or other compound as described herein. In an embodiment, said compound has a pIC50 value of at least 4 in a cancer cell or tumor growth inhibition assay and/or an immunostimulation assay. In an embodiment, said compound has a pIC50 value of at least 5. In an embodiment, said compound has a pIC50 value of at least 6. In an embodiment, said compound has a pIC50 value of at least 7.

In an embodiment, the invention provides a method of selectively inhibiting an FPPS enzyme, a GGPPS enzyme, and a DPPS enzyme comprising contacting said enzymes or a cell containing said enzymes with an organic compound, wherein said compound is capable of selectively inhibiting said FPPS, GGPPS, and DPPS enzymes.

In an embodiment, the invention provides a method of selectively inhibiting a GGPPS enzyme and a DPPS enzyme comprising contacting said enzymes or a cell containing said enzymes with an organic compound, wherein said compound is capable of selectively inhibiting said GGPPS enzyme and said DPPS enzyme. In an embodiment, the compound is of formula XA1, Z=Z1, and $R_4$=RL. In an embodiment, said compound is compound 715.

In an embodiment, the invention provides a method of selectively inhibiting a GGPPS enzyme without substantially inhibiting a DPPS enzyme comprising contacting said enzymes or a cell containing said enzymes with an organic compound, wherein said compound is capable of selectively inhibiting said GGPPS enzyme without substantially inhibiting said DPPS enzyme. In an embodiment, the compound is of formula XA1, Z=Z12, and $R_4$=RL. In an embodiment, said compound is compound 754.

In an embodiment, the invention provides a method of one or more of immunostimulation and inhibition of tumor or cancer cell growth, comprising contacting a mammalian cell with an organic bisphosphonate compound capable of substantially inhibiting a GGPPS enzyme and a DPPS enzyme.

In an embodiment, the invention provides a method of inhibition of cancer cell growth, comprising contacting a mammalian cell with an organic bisphosphonate compound capable of substantially inhibiting a GGPPS enzyme without substantially inhibiting a DPPS enzyme.

In an embodiment of any one of the foregoing methods, said compound has a structure of formula XA1.

In an embodiment, the invention provides a method of screening an organic bisphosphonate test compound for one or more properties, comprising: providing said test compound, measuring a performance attribute of said test compound in at least two enzyme assays selected from the group consisting of: an FPPS enzyme assay; a GGPPS enzyme assay; a DPPS enzyme assay; and measuring an activity level of said test compound in at least two activity assays selected from the group consisting of: a cancer cell or tumor growth inhibition assay; a T cell activation assay; a bone resorption assay; a bone binding assay; analyzing said performance attributes and said activity levels; and selecting said test compound based on said attributes and activity levels; thereby screening said test compound for said one or more properties. In an embodiment, the method further comprises providing a reference compound and comparing a performance attribute of said reference compound with said performance attribute of said test compound.

In an embodiment, the invention provides a method of inhibiting a dehydrodolichyl diphosphate synthase (DH-DDS) enzyme. In an embodiment, the invention provides a method of selectively inhibiting a DHDDS enzyme comprising contacting said enzyme or a cell containing said enzyme with an organic compound or composition of the invention. In an embodiment herein wherein a method is described as inhibiting a target selectively, there can be specific inhibition of one or more other targets.

In an embodiment, the invention provides a method of treating a cancer comprising administering to a patient in need thereof, a therapeutically effective amount of a compound of the invention or a pharmaceutical formulation thereof. In an embodiment, the cancer is breast cancer. In an embodiment, the breast cancer involves an actual or potential bone metastatic condition.

In an embodiment, the invention provides a method of treating a bone resorption disorder comprising administering to a patient in need thereof, a therapeutically effective amount of a compound of the invention or a pharmaceutical formulation thereof.

In an embodiment, the invention provides a method of treating a bone pain condition comprising administering to a patient in need thereof, a therapeutically effective amount of a compound of the invention or a pharmaceutical formulation thereof.

In an embodiment, the invention provides a method of treating an infectious disease comprising administering to a patient in need thereof, a therapeutically effective amount of a compound of the invention or a pharmaceutical formulation thereof. In an embodiment, said infectious disease relates to an agent selected from the group consisting of: a virus, a fungus, a bacterium, and a protozoan parasite. In an embodiment, said virus is a retrovirus. In an embodiment, said retrovirus is human immunodeficiency virus (HIV). In an embodiment, said protozoan parasite is selected from the group consisting of: *Leishmania, Toxoplasma, Cryptosporidium, Plasmodium*, and *Trypanosoma*. In an embodiment, said protozoan parasite is *Leishmania major*. In an embodiment, said bacterium is *Escherichia coli* or *Staphylococcus aureus*.

In an embodiment, the invention provides a method of immunotherapeutic treatment comprising administering to a patient in need thereof, a therapeutically effective amount of a compound of the invention or a pharmaceutical formulation thereof. In an embodiment, the invention provides a method of stimulating a T cell, comprising contacting the T cell with a compound of the invention or a pharmaceutical formulation thereof. In an embodiment, said T cell is a gammadelta T cell.

In an embodiment, the invention provides a method of synthesizing a compound of the invention or a pharmaceutical formulation thereof.

In an embodiment, the invention provides a method of inhibiting growth of an infectious disease agent comprising contacting said infectious disease agent with an effective amount of a compound of the invention or a pharmaceutical formulation thereof.

In an embodiment, the invention provides a method of inhibiting growth of a tumor or cancer cell comprising contacting said tumor or cancer cell with an effective amount of a compound of the invention or a pharmaceutical formulation thereof.

In an embodiment, the invention provides a compound having anti-angiogenic activity. In an embodiment, the invention provides a method of inhibiting angiogenesis comprising administering to a subject in need thereof an effective amount of a compound or composition of the invention.

In an embodiment, the invention provides a composition comprising a compound. In embodiment, said composition comprises a therapeutically effective amount of the compound. In an embodiment, the invention provides a composition comprising a pharmaceutical formulation of a compound. In an embodiment, said pharmaceutical formulation comprises one or more excipients, carriers, and/or other components as would be understood in the art. In an embodiment, an effective amount of a composition of the invention can be a therapeutically effective amount.

In an embodiment, a composition of the invention is used as a medicament. In an embodiment, a composition is used in the preparation or manufacture of a medicament. In an embodiment, the medicament is for treatment of one or more conditions as described herein and as would be understood in the art.

In an embodiment, the invention provides a method for treating a medical condition comprising administering to a subject in need thereof, a therapeutically effective amount of a compound of the invention. In an embodiment, the medical condition is a bone resorption disorder, a cancer, pain, an immune system disorder, and/or an infectious disease.

In an embodiment, a composition of the invention is isolated or purified.

In a screening method embodiment, a purified FPPS, GGPPS, DPPS, or other enzyme can be employed in addition to cellular and animal-based assays.

Without wishing to be bound by any particular theory, there can be discussion herein of beliefs or understandings of underlying principles or mechanisms relating to the invention. It is recognized that regardless of the ultimate correctness of any mechanistic explanation or hypothesis, an embodiment of the invention can nonetheless be operative and useful.

Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^-$, $Br^-$), sulfate, acetates (e.g., acetate, trifluoroacetate), ascorbates, aspartates, benzoates, citrates, and lactate.

Certain molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

BRIEF DESCRIPTION OF THE FIGURES

FIG. 11B, sulfonium bisphosphonate; FIG. 11C, phosphonium bisphosphonate; FIG. 11D, guanidinium bisphosphonate).

DETAILED DESCRIPTION OF THE INVENTION

Figure 1:
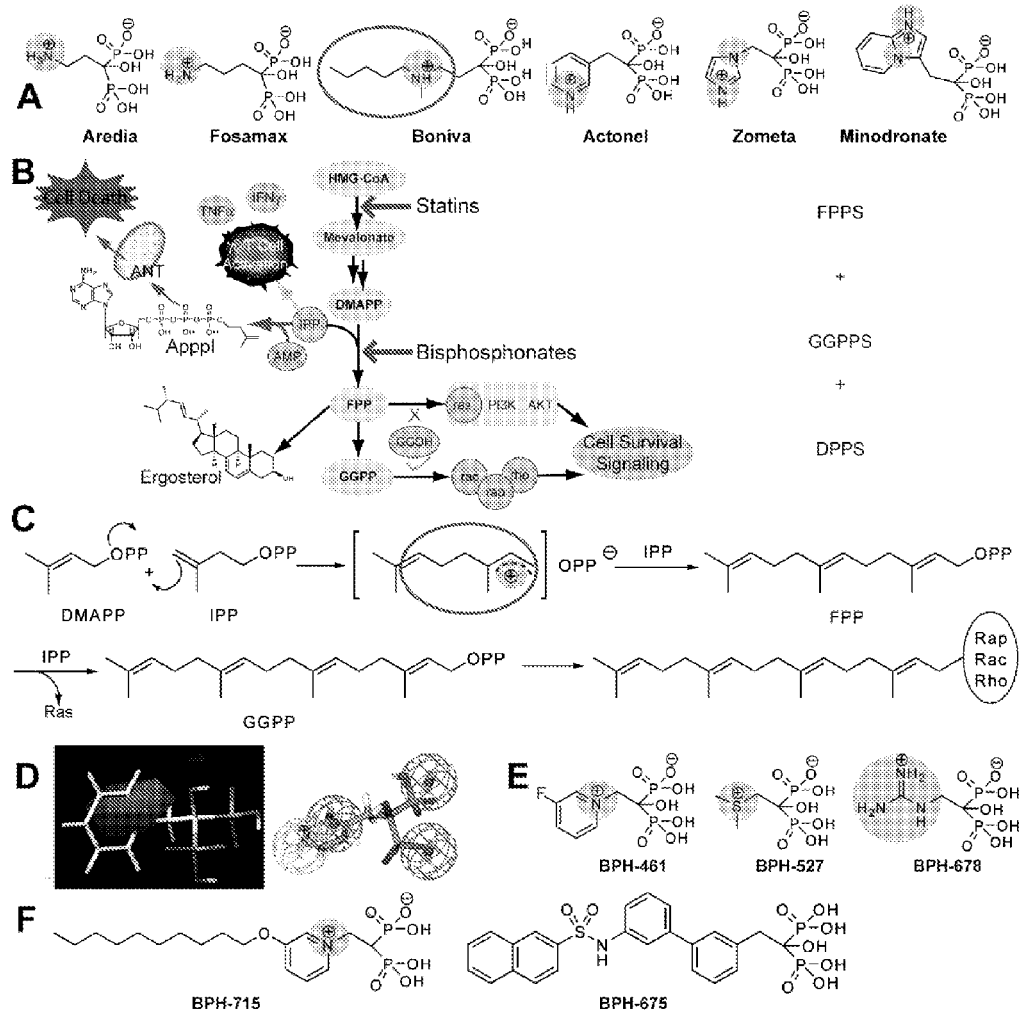
FIG. 1 illustrates aspects of relevant chemistry. A, Structures of common nitrogen-containing bisphosphonates; B, schematic illustration of several pathways involved in bisphosphonate activity in tumor cells, γδ T cells, osteoclasts, and macrophages. C, FPP, GGPP biosynthesis and protein prenylation showing carbocation transition state/reactive intermediates and bisphosphonate analog (enclosed in red circle); D, comparative molecular similarity index electrostatic field (left, blue=positive charge favored)) and pharmacophore (right, green=hydrophobic, red=positive, blue=negative ionizable) for FPPS inhibition; E, cationic bisphosphonates; F, structures of selected GGPPS inhibitors.

In embodiments, the invention relates at least in part to the discovery that certain compounds including bisphosphonates, particularly those having at least one substituent carrying a long hydrocarbon chain, particularly a straight chain alkyl or alkoxy group having 7 or more carbon atoms, exhibit useful or enhanced activity including in the context of inhibition of cell growth and/or inhibition of certain enzymes.

The following abbreviations are applicable. FPPS, farnesyl diphosphate synthase (also known as farnesyl pyrophosphate synthetase, dimethylallyltranstransferase, geranyltransferase, farnesyl diphosphate synthetase, and farnesyl pyrophosphate synthetase); GGPPS, geranylgeranyl diphosphate synthase (also known as geranylgeranyl pyrophosphate synthetase); DPPS, decaprenyl pyrophosphate synthase; UPPS (undecaprenyl pyrophosphate synthetase; also known as undecaprenyl diphosphate synthase); DHDDS or DDPPS, dehydrodolichyl diphosphate synthase; $pIC_{50}/pEC_{50}$, negative log of $IC_{50}$ and $EC_{50}$, respectively, where $IC_{50}$ and $EC_{50}$ are the concentrations that produce half-maximal inhibition or activation, respectively; T. brucei, Trypanosoma brucei; D. discoideum, Dictyostelium discoideum; γδ T cells, gamma delta T cells; ITC, isothermal calorimetry. Compounds/structures are typically designated by a number for convenience.

The following definitions are applicable. The chemical group definitions are intended to relate in particular to compounds having the general formula XA1 but can also apply to other compounds set forth herein.

Alkyl groups include straight-chain, branched and cyclic alkyl groups. Alkyl groups include those having from 1 to 20 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-20 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups optionally include substituted alkyl groups. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two 0, and those with one or two S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

The rings that may be formed from two or more of any R (e.g., R1 and R2) groups herein together can be optionally substituted cycloalkyl groups, optionally substituted cycloalkenyl groups or aromatic groups. The rings may contain 3, 4, 5, 6, 7 or more carbons. The rings may be heteroaromatic in which one, two or three carbons in the aromatic ring are replaced with N, O or S. The rings may be heteroalkyl or heteroalkenyl, in which one or more $CH_2$ groups in the ring are replaced with O, N, NH, or S.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl groups and more specifically where R is methyl, ethyl, propyl, butyl, or phenyl groups all of which groups are optionally substituted;

—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R═H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted;

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

THE EXAMPLES

The invention may be further understood by the following non-limiting examples.

Example 1

Bisphosphonate Compounds Including Structures with High Potency for Anti-Cancer and/or Immunostimulatory Function Bisphosphonates such as Fosamax, Actonel and Zometa are potent inhibitors of the enzyme farnesyl diphosphate synthase (FPPS) and are used to treat osteoporosis and bone cancers. They have direct activity against osteoclasts and tumor cells and also activate gammadelta T cells of the innate immune system to kill tumor cells. Here, we show that bisphosphonates can act as polypharmaceuticals, inhibiting not only FPPS but geranylgeranyl diphosphate and decaprenyl diphosphate synthases as well, in addition to describing the development of novel compounds having activities approximately 100-1000× greater than current bisphosphonates in γδ T cell activation and tumor cell killing.

Bisphosphonates such as Fosamax, Boniva and Zometa are drug molecules used to treat bone resorption diseases such as osteoporosis, Paget's disease and hypercalcemia due to malignancy(1, 2). In addition, they activate γδ T cells (containing the Vγ2Vδ T cell receptor) to kill tumor cells(3-5), plus, they have direct activity against tumor cells (6-9) and many parasitic protozoa(10, 11). While used clinically for two decades, their mode of action has been unclear. In early work, bisphosphonates were thought to act simply by coating bone surfaces, but more recently, the enzyme farnesyl diphosphate synthase (FPPS, EC 2.5.1.10) has been implicated(12). Inhibition of FPPS results in decreased prenylation of small GTPases (such as Ras, Rho, Rap, Rac) which is expected to caused deranged patterns of cell signaling (FIG. 1B) and in some protozoa, inhibition of ergosterol biosynthesis(10). More recently, it has been shown that this inhibition of FPPS results in increased levels of the substrate, isopentenyl diphosphate (IPP)(13, 14). This increase in IPP levels can activate γδ T cells (15). And, in some cells, IPP is converted to the isopentenyl ester of ATP, Apppl, which can inhibit the mitochondrial adenine nucleotide translocase (ANT), a component of the mitochondrial permeability transition pore (FIG. 1B) (16).

Herein we disclose significant answers to the questions: is FPPS inhibition always the major target for bisphosphonate action? And, is it possible to make more active and selective inhibitors, including ones that might have less avidity for bone, of potential use in immunotherapy, cancer, and as anti-infectives? We report that other important targets for bisphosphonate compound action include GGPPS and DPPS. Furthermore, we have made and tested organic bisphosphonate compounds which exhibit high potency and selectivity regarding various targets.

Proteins are prenylated by either farnesyl diphosphate (FPP) or geranylgeranyl diphosphate (GGPP), which are synthesized from IPP and dimethylallyl diphosphate (DMAPP) as shown in FIG. 1C. The reactions are believed to proceed via carbocationic transition state/reactive intermediates(17) such as that circled in red in FIG. 2C, with the bisphosphonate sidechains (of e.g. Boniva, red, FIG. 1A) mimicking the charge center and the bisphosphonate providing a hydrolytically stable analog of diphosphate(17). We proposed that analogous types of transition states could be relevant for both FPPS and GGPPS, as well as decaprenyl diphosphate synthase (DPPS). DPPS is a heterodimeric prenyl-transferase used in coenzyme Q$_{10}$ production(18). In accordance with our proposal, we designed bisphosphonate compounds that could affect multiple targets.

There has been aspirational recognition for drug design approaches to consider the prospect of going beyond the "one drug, one target" convention (19). We put forth the possibility that bisphosphonates could be "polypharmaceuticals" capable of inhibiting multiple targets. The bisphosphonate Boniva can be a potent inhibitor of squalene synthase(20), used in cholesterol biosynthesis, and numerous bisphosphonates are potent, low nM inhibitors of another heterodimeric prenyltransferase, geranyl diphosphate synthase, found in plants(21). The ability to determine the potential significance of other relevant target enzymes and to develop inhibitors, however, involved further exploration.

To test our polypharmaceutical hypothesis, we expressed three enzymes: human FPPS, GGPPS and DPPS, and tested each for their inhibition by a series of bisphosphonates. Each of these three enzymes is inhibited by the bisphosphonate zoledronate (Zometa), with certain indicated IC$_{50}$ (Ki) values shown in Table 1; activity values are also shown for other bisphosphonate compounds. Thus, we demonstrated that all three human enzymes can be potently inhibited by bisphosphonates. This finding is consistent with the possibility that FPPS is not the only target for bisphosphonates. We suggest the potential importance of GGPPS as a primary target for bisphosphonates and note the observation of Goffinet et al. (22) and others that the effects of bisphosphonates on cell growth are only reversed by addition of geranylgeraniol and not farnesol, implicating the involvement of FPPsynthase and GPPsynthase in the context of studying cholesterol biosynthesis. Our data demonstrate that certain small molecules can directly inhibit GGPPS target activity, in addition to other targets, with high potency.

We probed the question of whether GGPPS serves as the major target for bisphosphonate activity, and the accompanying role of small molecule inhibitors, in more depth. We designed a series of novel bisphosphonates that might have improved activity against one or more of these three enzymes in order to provide useful compositions and to provide a database which might help interpret certain cellular (tumor cell killing and γδ T cell activation) results. Our inspection of comparative molecular similarity analysis (CoMSIA)(23) models for FPPS inhibition(24) (FIG. 1E) suggested that enhanced activity might be obtained by moving the positive charge feature closer to the bisphosphonate backbone, as found for example in the novel bisphosphonates shown in FIG. 1F. We note the previous study of the inhibition of a human recombinant geranylgeranyl diphosphate synthase (25). In addition to the structural feature of the positive charge, we postulated the possible importance of having a large hydrophobic tail (see, e.g., FIG. 1F). Furthermore, we considered the prospect that such inhibitors might be particularly potent against the $C_{50}$ prenyltransferase DPPS, as well as having improved cellular uptake. Thus we were inspired to design and synthesize a variety of compounds; a representative specific member of which is compound 715.

Figure 2:
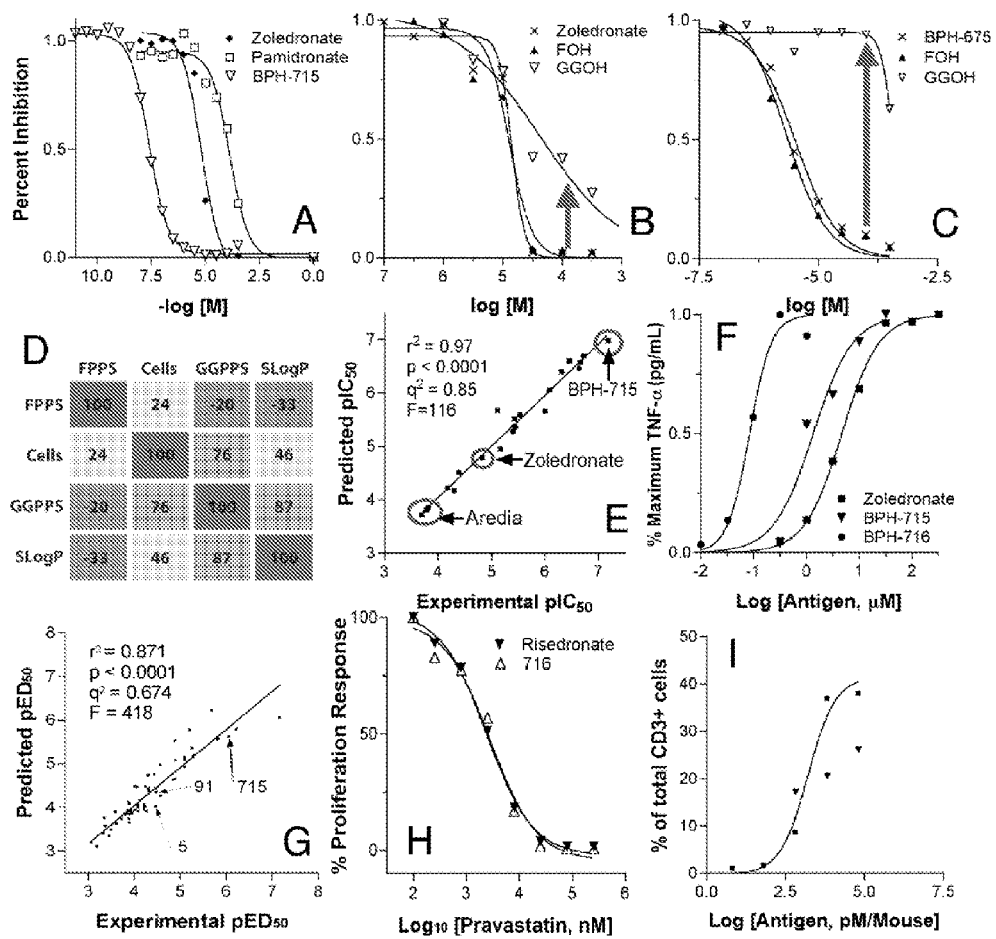
FIGS. 2A-2I illustrates extensive results of assays for activity of compounds including data for tumor cell growth inhibition and γδ T cell activation. A, MCF-7 cell growth inhibition by bisphosphonates; B, FOH, GGOH rescue of zoledronate cell growth inhibition; C, FOH, GGOH rescue of BPH-675 cell growth inhibition; D, correlation matrix for enzyme, cell growth inhibition and SlogP; E, CoMSIA predictions with FPPS and GGPS descriptors; F, gammadelta T cell activation by bisphosphonates; G, HQSAR predictions for γδ T cell activation; H, percent proliferation response; I, percent of total CD3+ cells.

As shown in FIG. 2A, cationic bisphosphonate species such as BPH-715 (FIG. 1F, left) are indeed far more active in MCF-7 tumor cell growth inhibition than are bisphosphonates such as zoledronate and pamidronate, with $IC_{50}$ values of approximately 50 nM, to be compared with values on the order of around 15 µM (zoledronate) or around 300 µM (pamidronate). There is no rescue from growth inhibition by addition of farnesol and only a partial rescue by geranylgeraniol, FIG. 2B, suggesting more than one target. On the other hand, the large hydrophobic bisphosphonate BPH-675 has an $IC_{50}$ of 5 µM, but its growth inhibitory effect is essentially fully rescued by addition of 20 µM geranyl geraniol, FIG. 2C. This strongly suggests that BPH-675 is a selective GGPPS inhibitor, while BPH-715 has multiple targets, including GGPPS. We found no rescue from cell growth inhibition from any bisphosphonate upon incorporation of $CoQ_{10}$ in growth medium, however, this is not unexpected given our mechanistic understanding since $CoQ_{10}$ is present in serum and the main effect of DPPS inhibition would be expected to be on IPP/Apppl elevation, which would not be affected by $CoQ_{10}$ addition.

In order to develop a model of cell growth inhibition based on enzyme data, we next determined the $IC_{50}$ values for FPPS, GGPPS and DPPS inhibition by certain bisphosphonates (certain data shown in Table 1). As shown in the data matrix in FIG. 2D, there is a good correlation between cell growth inhibition and GGPPS inhibition $pIC_{50}$ values, a moderate correlation with SlogP, the Log of the octanol/water partition coefficient based on atom contribution and protonation state (26), a weak correlation with DPPS but no correlation with FPPS inhibition. These results strongly support the idea that GGPPS inhibition is of prime importance and are consistent with the data we generated for GGOH and FOH rescue studies (see FIG. 2B, 2C).

We sought to develop a more quantitative model for cell growth inhibition, by using a partial least squares method to regress the enzyme and SlogP data against the cell $IC_{50}$ results. That is:

$$pIC_{50}(cell)=a \cdot pIC_{50}(FPPS)+b \cdot pIC_{50}(GGPPS)+c \cdot pIC_{50}(DPPS)+d \cdot S \log P+e$$

where $pIC_{50}=-\log_{10}(IC_{50} M)$ and a, b . . . n are regression coefficients.

Using solely enzyme inhibition and SlogP data we find a good overall correlation (R=0.90) using just GGPPS, DPPS and SlogP with GGPPS dominating (SI), with further improvements being obtained when using the CoMSIA fields (FIG. 2E). So, cell growth inhibition by bisphosphonates is dominated by direct inhibition of GGPPS, consistent with the rescue experiments, since Rho, Rap and Rac cell survival pathways are affected. Plus, DPPS inhibition is expected to produce large amounts of IPP (Apppl), since 7 moles of IPP would be consumed per DPP molecule produced.

We next sought to investigate whether or not these novel bisphosphonates have activity in γδ T cell activation. As can be seen in FIG. 2F, long chain bisphosphonates such as BPH-715 have potent activity in γδ T cell activation, with the most active species (BPH-716, containing a $C_{12}$ sidechain) having an $EC_{50}$~2×, more active in this assay than the classic synthetic phosphoantigen Phosphostim® (the bromohydrin of IPP) and ~100× more active than the most potent conventional bisphosphonates, FIG. 2F. These most potent species have little or no activity against FPPS (SI), however, they are ~10× more active against DPPS than is zoledronate (~500 nM versus ~5 µM). In addition, they have far more favorable SlogP properties (3 vs. −4), meaning that they might more readily enter cells. Of course, it might be argued that these species could be directly presented to γδ T cells as with other lipid antigens. However, the results of both pravastatin and mevastatin titration experiments(14), in which isoprenoid flux to FPPS, GGPPS and DPPS is blocked via inhibition of HMGCoA reductase, show identical statin $IC_{50}$ values for a potent long chain bisphosphonate and risedronate (FIGS. 2E,F,G) in γδ T cell activation. So, the novel species act in the same way as do conventional bisphosphonate antigens, via IPP accumulation in the antigen-presenting cells. Our application of the same modeling methods as used for tumor cell growth inhibition resulted in a highly predictive model (FIG. 2I), with FPPS, DPPS, SlogP descriptors together with additional CoMSIA field descriptors, (SI), with an $r^2$ value of 0.98, $q^2$=0.744).

We find no evidence of a role for GGPPS inhibition in γδ T cell activation. For example, the GGPPS inhibitor BPH-675 (which has no effect on FPPS or DPPS) had no effect at all on γδ T cell activation. Likewise, a phenyl analog of BPH-715 (BPH-754) in which there is no side-chain charge, was found to be a good GGPPS inhibitor. Its inhibition of MCF-7 cell growth was rescued by GGOH, but it had no effect on γδ T cell activation since it had essentially no effect on FPPS or DPPS inhibition (since it lacked the carbocation charge feature). While this lack of activity in γδ T cell activation might at first seem surprising, inhibition of GGPPS alone produces only 1 IPP, while DPPS inhibition produces 7, plus, DPP/$CoQ_{10}$ production is very abundant in cells. It is also possible that inhibition of dolichol biosynthesis could be involved in IPP production.

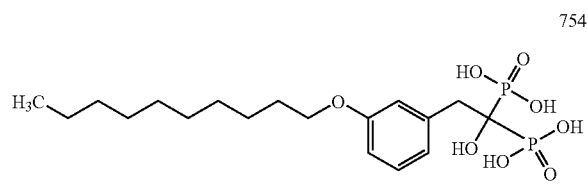

754

A potential drawback to the use of bisphosphonates in treating non-bone resorption diseases is expected to be that they would be rapidly adsorbed onto bone. Surprisingly, however, we find that the highly hydrophobic species BPH-675 and BPH-715 are only very weakly adsorbed onto bone in vivo (SI), resulting in only modest $IC_{50}$ values in bone resorption (e.g. ~800 nM for BPH-715 versus ~70 nM for zoledronate, SI), but weak bone binding is desirable in the context of certain conditions, e.g., immunotherapy, treating infectious diseases, and various cancers.

We note that the compound 754 and certain compounds with related structural features can represent a genus of compounds which potently inhibits GGPPS while not substantially inhibiting DPPS or FPPS. In certain instances it can be advantageous to retain properties such as anti-cancer activity while not having a pro-immunostimulatory effect. There are circumstances where immunostimulation can lead to immune system overreaction such as in a variety of inflammatory disorders. The structural features of interest can include the lack of positive charge for the ring moiety adjoining the bisphosphonate component in addition to an alkoxy tail substituent on the ring. Conversely, compounds which share other structural features (e.g., presence of the positive charge and the tail substituent) can exhibit accompanying functional properties such as inhibition of multiple targets (for example, GGPPS and DPPS in the case of compound 715) and can demonstrate combinations of activities such as anti-cancer and immunostimulation; there are circumstances where such combinations can be advantageous.

Figure 3:
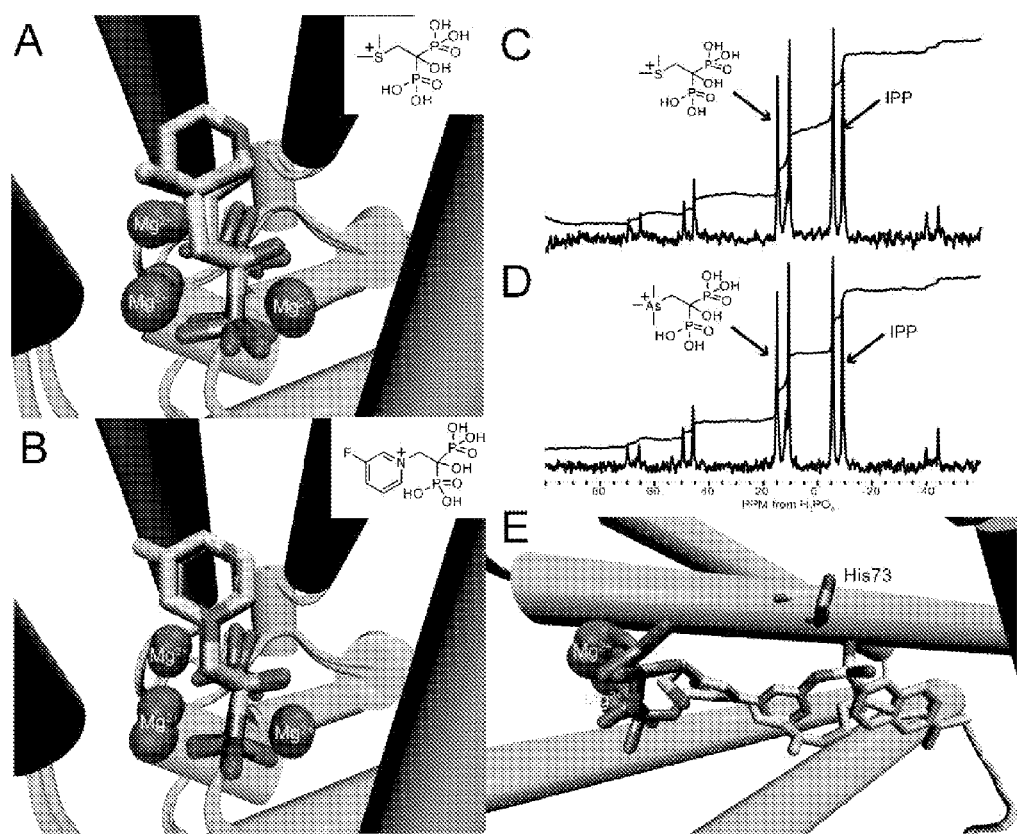
FIGS. 3A-3E illustrates results from X-ray and NMR experiments. A,B: x-ray structures of BPH-527 and BPH-461 bound to human FPPS shown superimposed on risedronate (from PDB File # 1YV5); C,D $^{31}P$ magic-angle sample spinning NMR spectra (600 MHz $^1H$ resonance frequency) of bisphosphonates, IPP bound to *T. brucei* FPPS; E, x-ray structure of BPH-675 bound to GGPPS (from *Saccharomyces cerevisae*) shown superimposed on GGPP bound to human GGPPS (PDB File 2FVI); see also Table 8.
Figure 12:
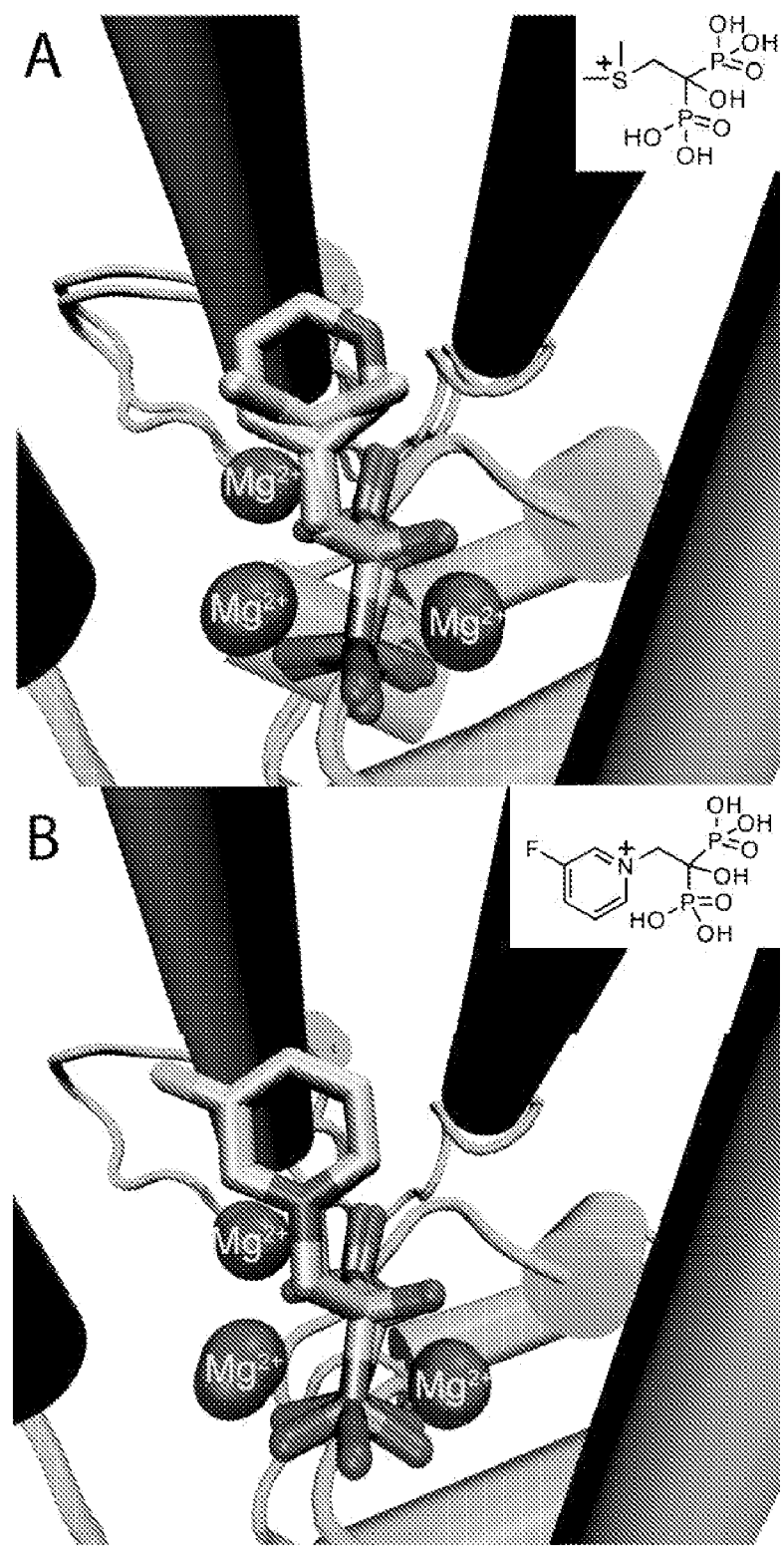
FIGS. 12A and B indicate X-ray structures of exemplary bisphosphonates bound to *Trypanosoma cruzi* FPPS. A, BPH-527 and B, BPH-461. Risedronate is shown superimposed on each.

We next investigated how certain bisphosphonates (e.g., pyridinium and sulfonium analogs) bind to FPPS and GGPPS. We chose to first study the simple fluoropyridinium bisphosphonate (BPH-461, FIG. 1D) previously found to have potent activity in FPPS inhibition and in bone resorption (27), as well as the simplest sulfonium bisphosphonate (BPH-527, FIG. 1D). Data collection and refinement statistics are shown in exemplary Tables, e.g., Tables 4-7, for both the human and *Trypanosoma brucei* FPPS enzymes, the latter being of interest as a target for anti-infective drug development(28). In all cases, the bisphosphonates bound exclusively to the allylic/DMAPP site, even in the absence of IPP. The structures of these two bisphosphonates bound to the human enzyme are shown in FIG. 3A,B, superimposed on the structure of BPH-210, a potent bone resorption drug(29) which also has activity against *E. coli*(30). The *T. brucei* structures are shown in FIG. 12). There is clearly considerable similarity in binding with the conventional bisphosphonates, with strong electrostatic interactions between the phosphonates and 3 $Mg^{2+}$, first identified by Hosfield et al. in the *Escherichia coli* protein(31).

Figure 11:
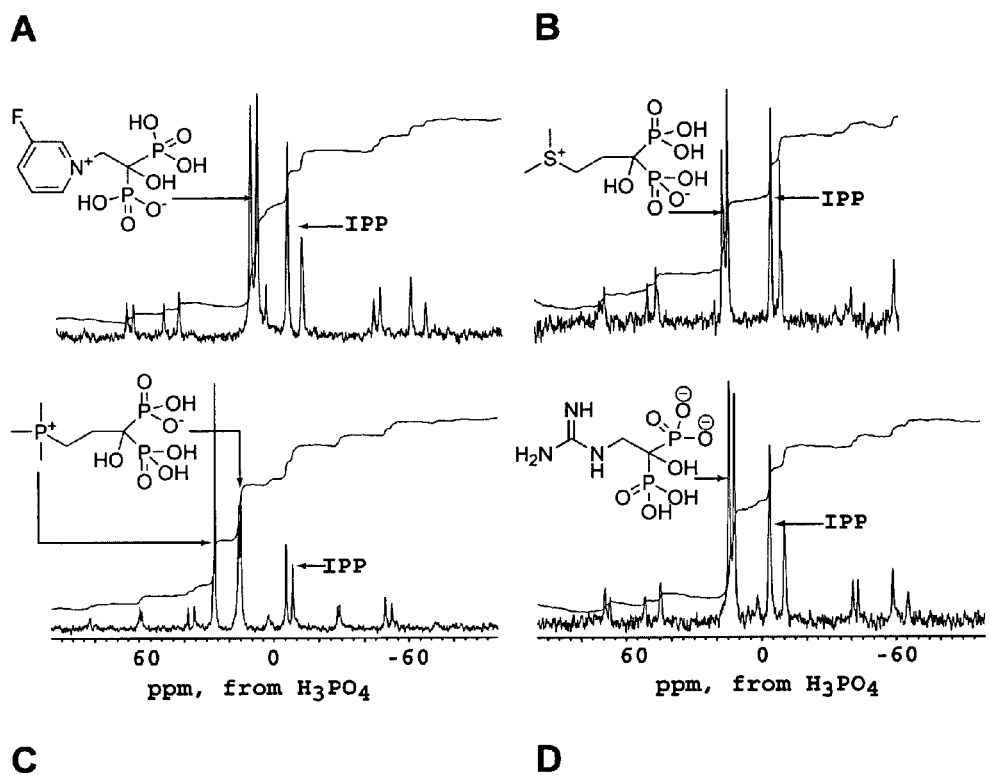
FIGS. 11A-D are exemplary $^{31}P$ NMR spectra of bisphosphonate/IPP/FPPS complexes. The structures of the compounds are shown above the spectra (FIG. 11A, pyridinium bisphosphonate.

In the presence of NBPs (nitrogen-containing bisphosphonate drugs) together with IPP, it has been found that ternary bisphosphonate-IPP-FPPS complexes form (31-34). This has been demonstrated crystallographically as well as by using solid state $^{31}P$ NMR spectroscopy, where individual $^{31}P$ NMR resonances are seen for both sets of bisphosphonate and IPP $^{31}P$ nuclei(35). The pyridinium bisphosphonate BPH-461 forms the same type of complex, containing 3 $Mg^{2+}$ plus IPP, shown in FIG. 3C. The formation of ternary complexes with IPP, $Mg^{2+}$ can also be deduced by using solid-state $^{31}P$ NMR and results for the pyridinium and sulfonium bisphosphonate are shown in FIG. 3C,D (and FIG. 11) and indicate that the pyridinium, sulfonium, phosphonium, arsonium and guanidinium bisphosphonates all form ternary complexes with, on average, a 1:1 (±0.2) bisphosphonate:IPP stoichiometry.

Figure 13:
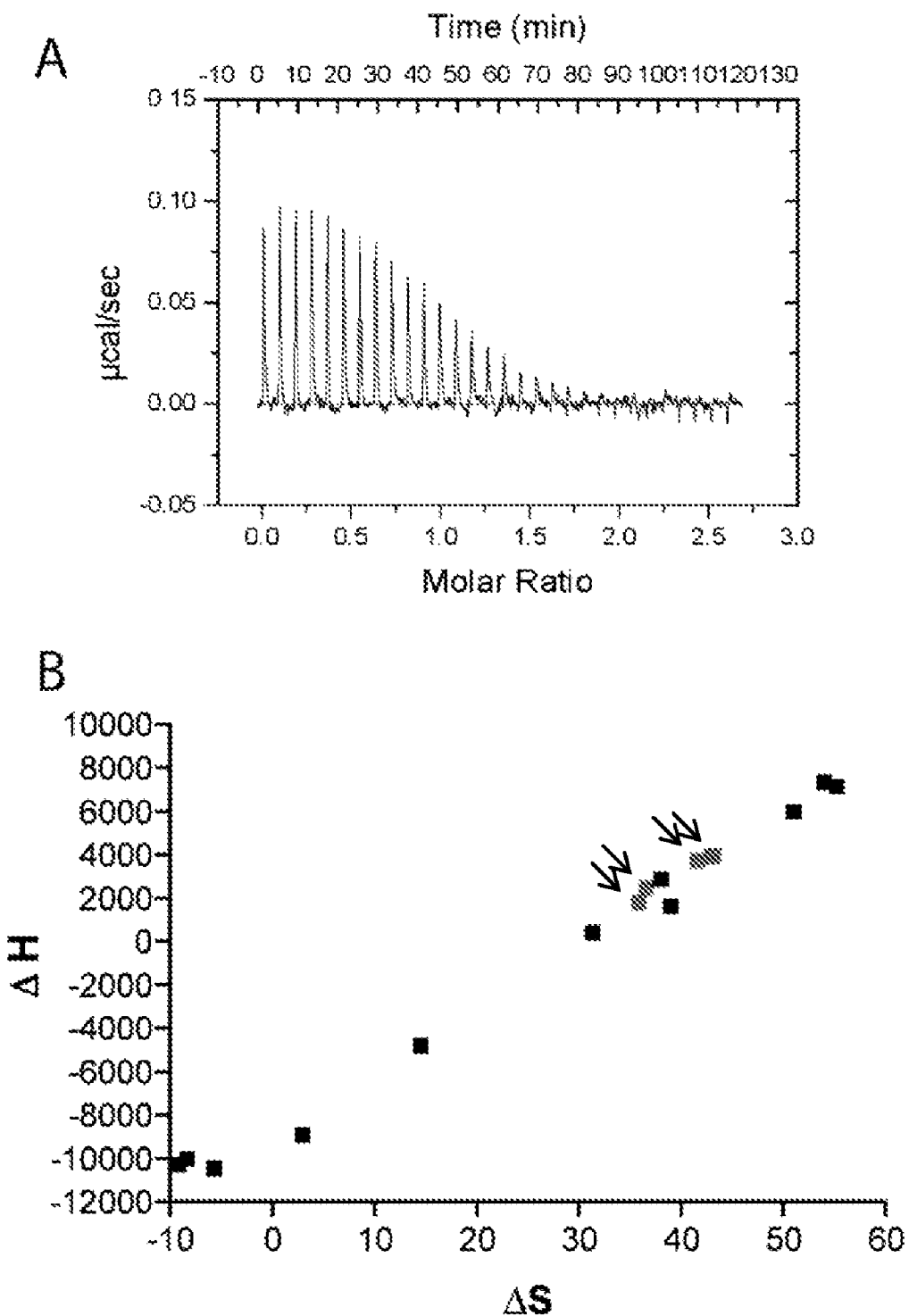
FIGS. 13A and B provide representative ITC results for a sulfonium bisphosphonate (BPH-527) bound to *T. brucei* FPPS and ΔH, ΔS correlation (novel cationic compounds in red with arrows, others from references).
Figure 14:
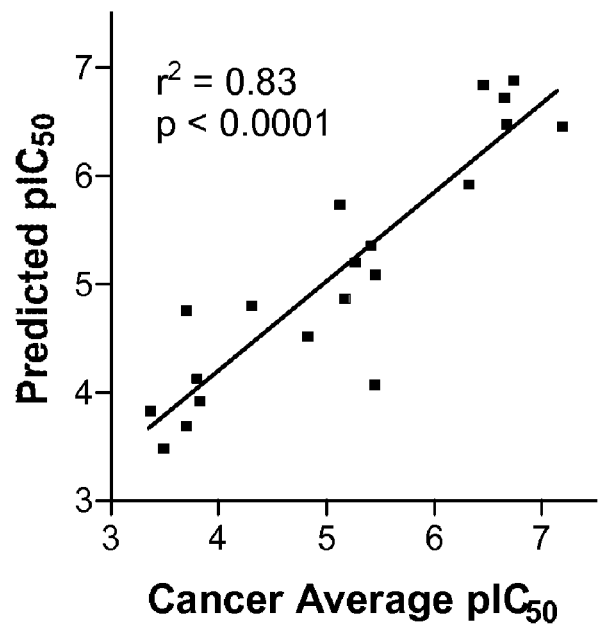
FIG. 14 is a graph of predicted cell growth inhibition based on FPPS, GGPPS enzyme inhibition in addition to SlogP descriptor.
Figure 15:
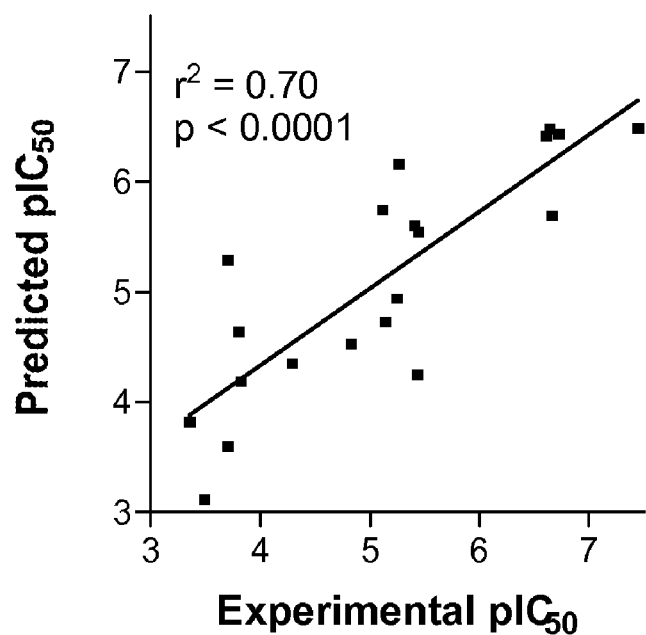
FIG. 15 is a graph of predicted cell growth inhibition based on FPPS and GGPPS enzyme inhibition data.
Figure 16:
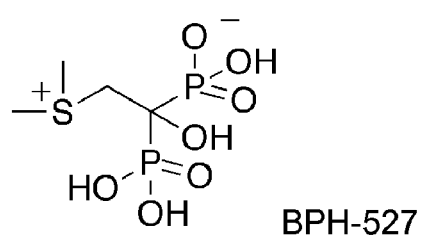
FIG. 16 provides structures of several compounds discussed herein.
Figure 16:
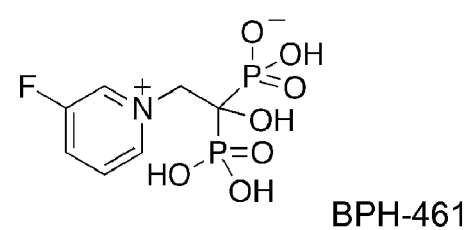
Figure 16:
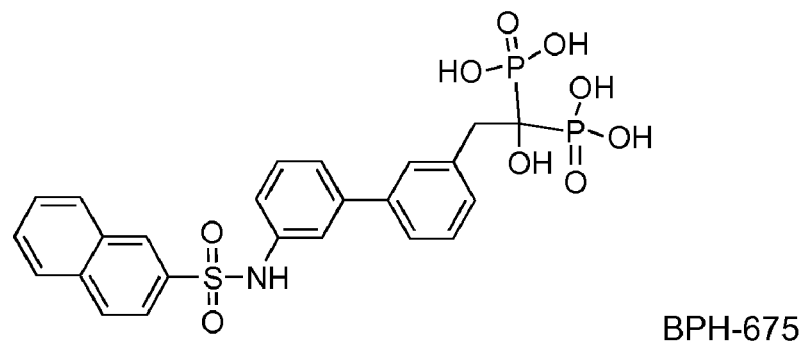

To determine whether cationic bisphosphonate binding to FPPS is entropy or enthalpy driven, we used isothermal titration calorimetry (ITC). ΔH values were small and endothermic (~2-4 kcal) and binding was overwhelmingly entropy driven, with −TΔS values in the range ~−10.5 to −12.6 kcal/mole. See FIG. 13 and Table 9. So, the unconventional bisphosphonates form the same types of complexes as do the more conventional nitrogen containing bisphosphonates, but binding is exclusively entropy driven—as found with conventional bisphosphonates such as alendronate and ibandronate, which have very basic side chains (34, 36).

Finally, we investigated the structure of the GGPPS inhibitor BPH-715 (in the presence and absence of IPP), which was designed to bind to GGPPS in its "inhibitor" site. Data collection and refinement statistics for two structures were obtained. In both structures, BPH-715 binds to the GGPP inhibitor site first identified by Kavanagh et al. (37). In one structure we find the presence of 2 $Mg^{2+}$ and 1 IPP, while in a second structure, the ligand binds alone with a slightly displacement from that seen in the ternary complex structure. The IPP site location is similar to that seen in FPPS (FIG. 3C) with the smaller pyridinium bisphosphonate. The same GGPPS inhibitor site binding site motif is also seen with BPH-675 (PDB 2E95) and may be common with long chain GGPPS inhibitors, such as those described earlier(25), as proposed by Kavanagh et al. (37). Since this is a product (or inhibitor) binding site, we determine that there is no requirement for a positive charge feature, and both cationic and neutral side-chain containing species can bind, but only the cationic species inhibit DPPS (and FPPS).

Figure 4:
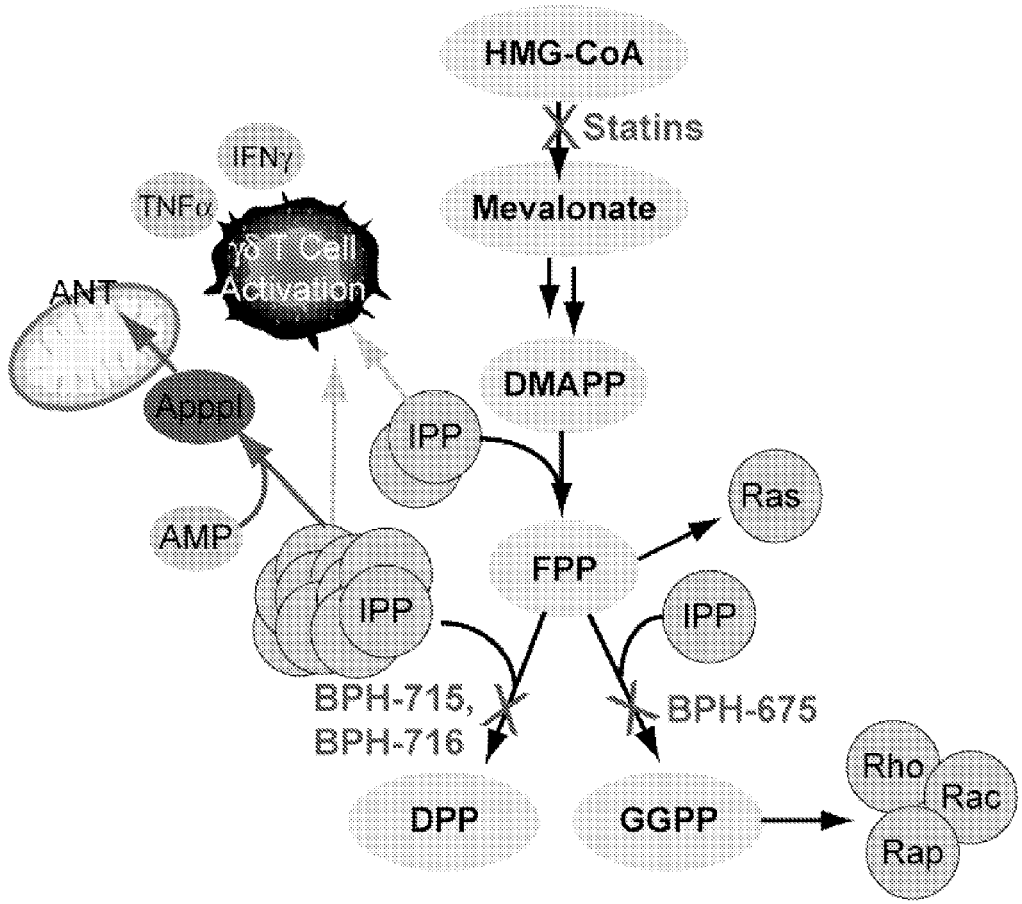
FIG. 4 is a schematic illustration of bisphosphonate targets.
Figure 5:
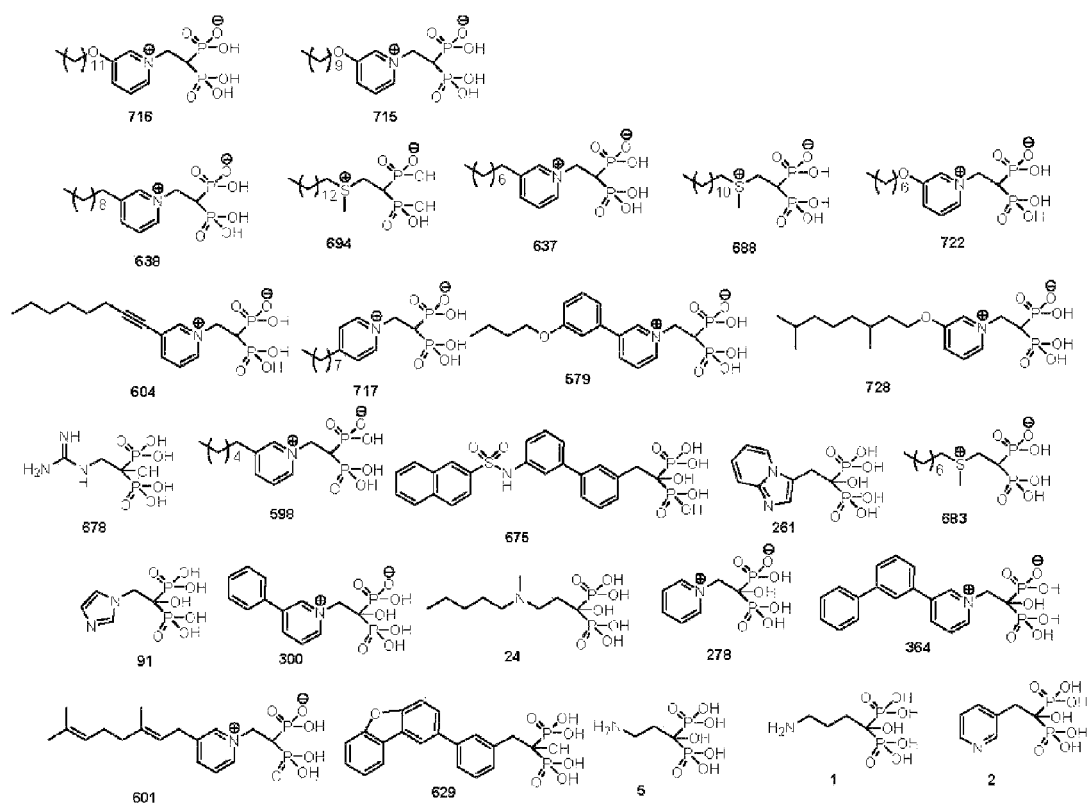
FIG. 5 provides structures of inhibitors investigated in MCF-7 cell growth inhibition, FPPS inhibition and GGPPS inhibition (FIGS. 2D-G).
Figure 6:
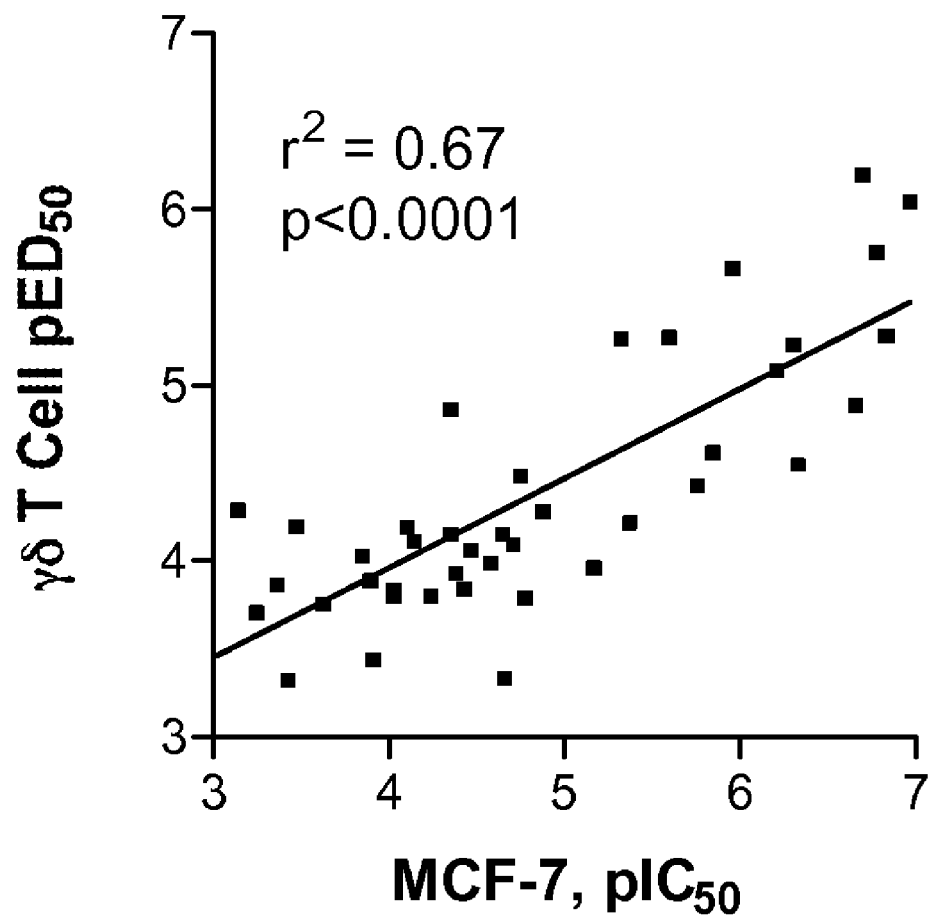
FIG. 6 is a graph of $pIC_{50}$ values for MCF-7 growth inhibition by bisphosphonates plotted versus the $pED_{50}$ values for γδT cell activation. The structures of the compounds investigated are shown in FIG. 5.
Figure 7:
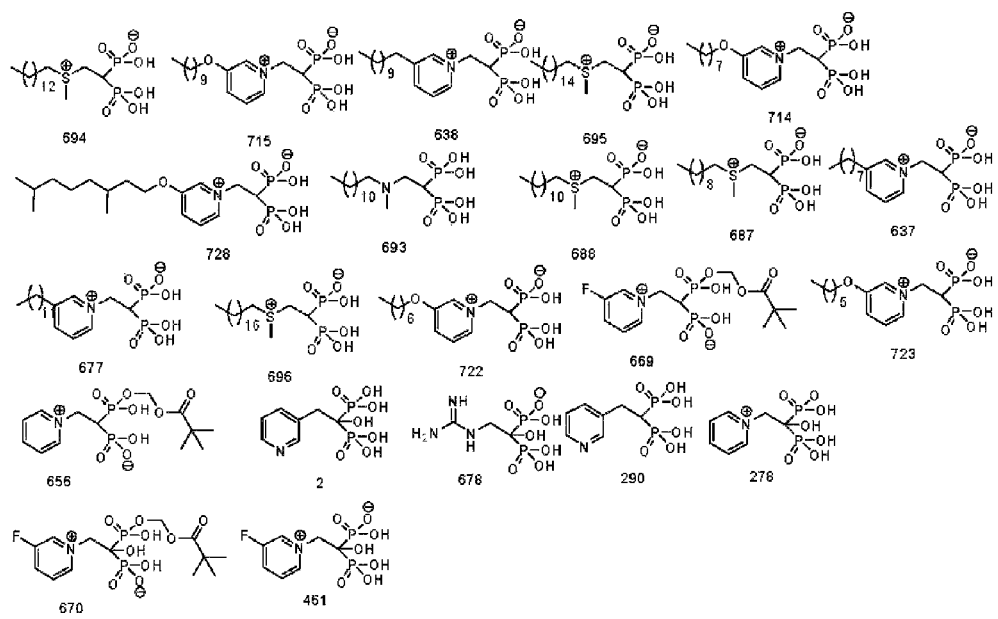
FIG. 7 provides structures of compounds investigated in assays including MCF-7 cell growth inhibition and γδ T cell activation.
Figure 8:
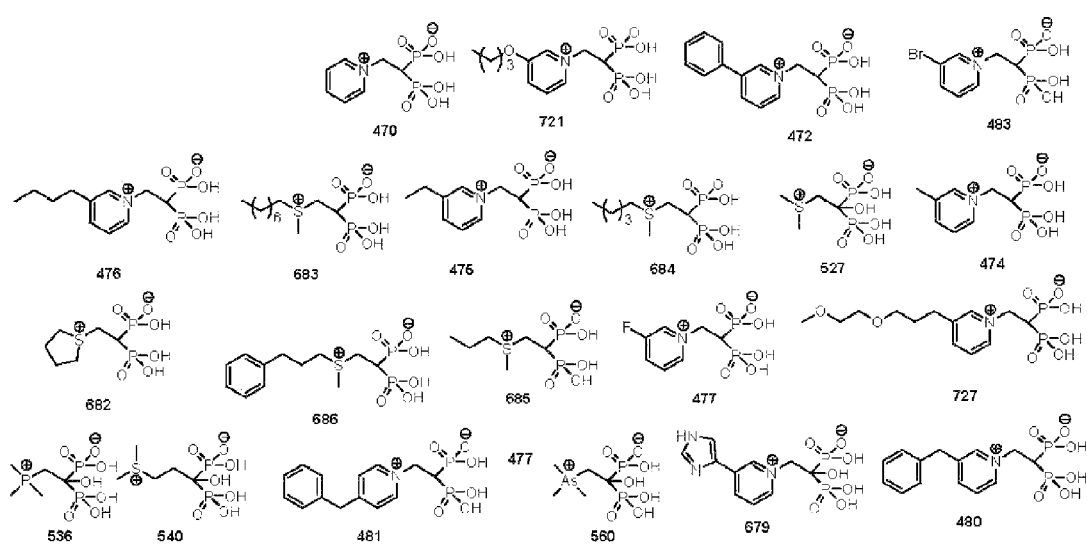
FIG. 8 provides structures of compounds investigated in assays including MCF-7 cell growth inhibition and γδ T cell activation.
Figure 9:
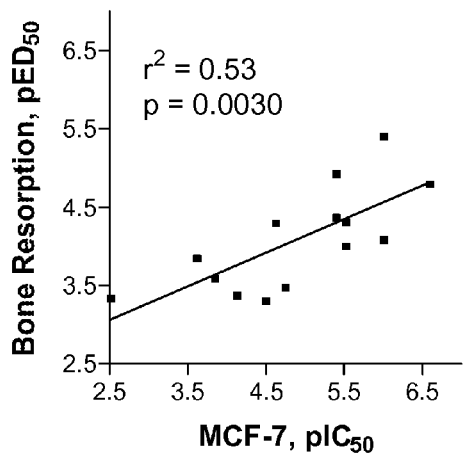
FIG. 9 is a graph of MCF-7 cell growth inhibition $pIC_{50}$ values versus bone resorption ($pED_{50}$ results, from Widler et al.). The structures of the compounds investigated are shown in FIG. 8.

Overall, these results are of great interest since they show that certain bisphosphonate drugs, rather than targeting exclusively FPPS, are polypharmaceuticals, able in many cases to inhibit FPPS, GGPPS as well as DPPS (and potentially, other prenyl transferases, such as dehydrodolichyl diphosphate synthase), suggesting the revised version of FIG. 2B shown in FIG. 4. FIG. 4 illustrates our understanding that tumor cell growth inhibition is inhibited primarily by GGPPS inhibition (as evidenced by computer models, enzyme inhibition and rescue experiments), but GGPPS inhibition plays no role in γδ T cell activation, which is dominated by FPPS and DPPS inhibition (and possibly, dolichol biosynthesis inhibition). $CoQ_{10}$ does not rescue cell growth, since IPP/Apppl accumulation still occurs. Long chain bisphosphonates have no activity against FPPS but are still potent γδ T cell activators due to DPPS inhibition and high hydrophobicity.

In tumor cell growth inhibition, GGPPS is the major target for the most potent species, but in γδ T cell activation, GGPPS inhibition has no effect on T cell activation, which relies on IPP formation. By suitable chemical modification, we have obtained several novel species having activities about 100-1000× greater than existing bisphosphonates in both tumor cell growth inhibition as well as γδ T cell activation, suggesting new routes to the use of bisphosphonates in immuno- and chemotherapy using a polypharmaceutical approach.

Certain compounds in this example are compounds of formula XA1 as described herein.

Variations on compositions including salts and ester forms of compounds. Compounds of this invention and compounds useful in the methods of this invention include those of the above formulas and pharmaceutically-acceptable salts and esters of those compounds. In embodiments, salts include any salts derived from the acids of the formulas herein which acceptable for use in human or veterinary applications. In embodiments, the term esters refers to hydrolyzable esters of compounds including diphosphonate compounds of the formulas herein. In embodiments, salts and esters of the compounds of the formulas herein can include those which have the same therapeutic or pharmaceutical (human or veterinary) general properties as the compounds of the formulas herein. Various combinations of salts are possible, with each phosphonate carrying a 2-, 1- or neutral charge. In principle there are multiple charge states possible, for example 9 charge states, for certain compounds including bisphosphonate compounds of this invention.

REFERENCES FOR EXAMPLE 1

1. R. G. Russell, Ann N Y Acad Sci 1068, 367 (April, 2006).
2. A. J. Roelofs, K. Thompson, S. Gordon, M. J. Rogers, Clin Cancer Res 12, 6222s (Oct. 15, 2006).
3. V. Kunzmann et al., Blood 96, 384 (Jul. 15, 2000).
4. M. Wilhelm et al., Blood 102, 200 (Jul. 1, 2003).
5. J. N. Blattman, P. D. Greenberg, Science 305, 200 (Jul. 9, 2004).
6. S. Yamagishi et al., Am J Pathol 165, 1865 (December, 2004).
7. S. Wakchoure et al., Clin Cancer Res 12, 2862 (May 1, 2006).
8. P. V. Dickson et al., Surgery 140, 227 (August, 2006).
9. D. Santini et al., Nat Clin Pract Oncol 3, 325 (June, 2006).
10. M. B. Martin et al., J Med Chem 44, 909 (Mar. 15, 2001).
11. B. Bouzahzah, L. A. Jelicks, S. A. Morris, L. M. Weiss, H. B. Tanowitz, Parasitol Res 96, 184 (June, 2005).
12. J. R. Green, Acta Oncol 44, 282 (2005).
13. H. J. Gober et al., J Exp Med 197, 163 (Jan. 20, 2003).
14. K. Thompson, M. J. Rogers, J Bone Miner Res 19, 278 (February, 2004).
15. Y. Tanaka et al., Nature 375, 155 (May 11, 1995).
16. H. Monkkonen et al., Br J Pharmacol 147, 437 (February, 2006).
17. M. B. Martin, W. Arnold, H. T. Heath, 3rd, J. A. Urbina, E. Oldfield, Biochem Biophys Res Commun 263, 754 (Oct. 5, 1999).
18. R. Saiki, A. Nagata, T. Kainou, H. Matsuda, M. Kawamukai, Febs J 272, 5606 (November, 2005).
19. A. L. Hopkins, J. S. Mason, J. P. Overington, Curr Opin Struct Biol 16, 127 (February, 2006).
20. D. Amin, S. A. Cornell, M. H. Perrone, G. E. Bilder, Arzneimittelforschung 46, 759 (August, 1996).
21. C. Burke, K. Klettke, R. Croteau, Arch Biochem Biophys 422, 52 (Feb. 1, 2004).
22. M. Goffinet et al., BMC Cancer 6, 60 (2006).
23. G. Klebe, U. Abraham, T. Mietzner, J Med Chem 37, 4130 (Nov. 25, 1994).
24. J. M. Sanders et al., J Med Chem 46, 5171 (Nov. 20, 2003).
25. C. M. Szabo et al., J Med Chem 45, 2185 (May 23, 2002).
26. S. A. Wildman, G. M. Crippen, Journal of Chemical Information and Computer Sciences 39, 868 (September-October, 1999).
27. J. M. Sanders et al., J Med Chem 48, 2957 (Apr. 21, 2005).
28. A. Montalvetti et al., J Biol Chem 278, 17075 (May 9, 2003).
29. L. Widler et al., J Med Chem 45, 3721 (Aug. 15, 2002).
30. A. Leon et al., J Med Chem 49, 7331 (Dec. 14, 2006).
31. D. J. Hosfield et al., J Biol Chem 279, 8526 (Mar. 5, 2004).
32. S. B. Gabelli et al., Proteins 62, 80 (Jan. 1, 2006).
33. J. M. Rondeau et al., ChemMedChem 1, 267 (February, 2006).
34. K. L. Kavanagh et al., Proc Natl Acad Sci USA 103, 7829 (May 16, 2006).
35. J. Mao et al., J Am Chem Soc 128, 14485 (Nov. 15, 2006).
36. F. Yin, R. Cao, A. Goddard, Y. Zhang, E. Oldfield, J Am Chem Soc 128, 3524 (Mar. 22, 2006).
37. K. L. Kavanagh, J. E. Dunford, G. Bunkoczi, R. G. Russell, U. Oppermann, J Biol Chem 281, 22004 (May 11, 2006).

Example 2

Additional Compounds

The invention provides compounds represented by structure XA2:

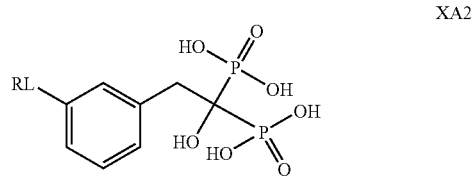

XA2 wherein variable group options can be as described elsewhere herein.

In a preferred embodiment, RL is an alkoxy having 7-12 carbons. In an embodiment, a compound having structural formula XA2 can be used to selectively inhibit GGPPS without substantially inhibiting DPPS. In an embodiment, such a compound is used to inhibit a tumor or cancer cell growth.

Compound 754 was synthesized and tested for activity. It was found to have in IC50 value as follows (micromolar): 0.50 for inhibition of cancer call growth (average); 0.401 for inhibition of human breast cancer cell line MCF7; 0.524 for inhibition of human CNS cancer SF268; 0.672 for inhibition of human lung cancer NCIH460; 0.5918 for inhibition of purified GGPPS.

Example 3

Results of Testing Compounds for Activities

TABLE 1

$pIC_{50}$ values for FPPS, GGPPS, and DPPS enzyme inhibition, cell growth inhibition, and QSAR predicted cell activity.

| | Experimental & Computed Values | | | | | | | Predicted Values | |
|---|---|---|---|---|---|---|---|---|---|
| Compound | FPPS pKi (M) | GGPPS pKi (M) | DPPS_pKi (M) | SlogP | SF-268 $pIC_{50}$ (M) | MCF-7 $pIC_{50}$ (M) | NCI-H460 $pIC_{50}$ (M) | NCI-H460 $pIC_{50}$ (M) | Residual |
| 715 | 7.3 | 8.1 | 8.3 | −1.2 | 7.0 | 6.7 | 7.2 | 6.7 | 0.5 |
| 638 | 7.8 | 8.0 | 6.3 | −1.1 | 6.7 | 6.8 | 6.8 | 6.7 | 0.1 |
| 722 | 8.9 | 7.2 | 8.2 | −2.4 | 6.0 | 5.6 | 6.3 | 5.7 | 0.6 |
| 717 | 7.7 | 7.7 | 7.1 | −1.8 | 6.2 | 6.3 | 6.2 | 6.2 | 0.0 |
| 694 | 7.1 | 7.4 | 6.6 | −0.1 | 5.9 | 4.9 | 6.0 | 5.3 | 0.7 |
| 604 | 8.9 | 7.3 | 7.0 | −2.4 | 5.8 | 5.3 | 6.0 | 5.8 | 0.2 |
| 637 | 8.9 | 7.4 | 6.3 | −2.5 | 5.9 | 6.6 | 5.7 | 6.0 | −0.3 |
| 688 | 8.6 | 7.5 | 6.5 | −0.8 | 5.6 | 5.2 | 5.5 | 6.0 | −0.5 |
| 675 | 5.9 | 7.1 | 6.5 | −0.2 | 5.2 | 5.2 | 5.3 | 4.4 | 1.0 |
| 683 | 8.5 | 7.0 | 7.2 | −2.4 | 4.9 | 4.7 | 4.8 | 5.1 | −0.3 |
| 261 | 8.9 | 5.5 | 6.8 | −4.7 | 4.9 | 4.8 | 4.8 | 4.4 | 0.4 |
| 91 | 8.9 | 5.6 | 7.4 | −5.5 | 4.8 | 4.7 | 4.8 | 4.4 | 0.4 |
| 678 | 7.9 | 5.7 | 7.4 | −9.0 | 4.6 | 4.7 | 4.7 | 4.0 | 0.7 |
| 754 | 5.3 | 7.8 | 6.7 | −0.9 | 4.6 | 4.6 | 4.7 | 5.4 | −0.7 |
| 728 | 6.8 | 7.5 | 6.3 | −1.5 | 4.9 | 4.5 | 4.6 | 5.4 | −0.8 |
| 300 | 8.3 | 6.4 | 6.9 | −3.8 | 4.5 | 4.4 | 4.5 | 4.2 | 0.3 |
| 679 | 8.2 | 5.0 | 6.0 | −5.0 | 4.5 | 4.4 | 4.3 | 4.1 | 0.2 |
| 472 | 8.6 | 6.6 | 7.1 | −3.1 | 4.3 | 4.4 | 4.3 | 4.3 | 0.0 |
| 474 | 8.4 | 5.8 | 6.9 | −4.4 | 4.1 | 4.1 | 4.2 | 4.2 | 0.0 |
| 278 | 8.6 | 5.4 | 7.2 | −5.4 | 4.3 | 4.1 | 4.1 | 4.3 | −0.1 |
| 483 | 8.5 | 5.5 | 6.8 | −3.9 | 4.0 | 4.0 | 4.1 | 4.2 | −0.1 |
| 5 | 7.4 | 5.3 | 6.3 | −7.0 | 3.5 | 3.9 | 4.0 | 3.8 | 0.2 |
| 685 | 8.3 | 5.7 | 6.7 | −4.3 | 3.7 | 3.6 | 3.9 | 4.1 | −0.3 |
| 684 | 8.0 | 6.6 | 7.0 | −3.6 | 3.7 | 3.6 | 3.8 | 4.1 | −0.4 |
| 2 | 8.6 | 5.0 | 7.3 | −5.0 | 3.9 | 3.8 | 3.7 | 4.3 | −0.6 |
| 24 | 8.3 | 5.6 | 7.3 | −5.6 | 3.8 | 3.7 | 3.7 | 4.2 | −0.5 |
| 1 | 7.2 | 4.9 | 6.3 | −6.7 | 3.5 | 3.3 | 3.5 | 3.7 | −0.2 |
| 727 | 8.2 | 5.6 | 6.8 | −3.8 | 3.7 | 3.5 | 3.5 | 4.1 | −0.6 |

In the preceding Table, data for cell growth inhibition of three cancer cell lines is demonstrated by various compounds. Also, compounds are able to inhibit one or more of FPPS, GGPPS, and DPPS enzymes, including compounds that can inhibit multiple enzymes with significant potency. Predicted values are from 10-fold cross-validated models. The mean absolute residuals error is 0.38 which corresponds to a factor of ~2.3× error over a 2500× range in activity. The GFA lack-of-fit error metric is 0.31.

TABLE 2

γδ T cell activation, MCF-7 cell growth inhibition results, presented as −log10(value, M)

| Compound ID | γδ T Cell Avg $pED_{50}$ (M) | MCF-7 Cell $pIC_{50}$ (M) |
|---|---|---|
| BPH-694 | 6.20 | 6.69 |
| BPH-715 | 6.05 | 6.97 |
| BPH-638 | 5.77 | 6.77 |
| BPH-695 | 5.68 | 5.95 |
| BPH-714 | 5.29 | 6.82 |
| BPH-728 | 5.28 | 5.59 |
| BPH-693 | 5.28 | 5.32 |
| BPH-688 | 5.25 | 6.30 |
| BPH-687 | 5.09 | 6.20 |
| BPH-637 | 4.90 | 6.66 |
| BPH-677 | 4.88 | 4.34 |
| BPH-696 | 4.63 | 5.85 |
| BPH-722 | 4.56 | 6.33 |
| BPH-669 | 4.49 | 4.75 |
| BPH-723 | 4.44 | 5.76 |
| BPH-656 | 4.29 | 4.88 |
| BPH-2 | 4.29 | 3.13 |
| BPH-678 | 4.22 | 5.37 |
| BPH-290 | 4.21 | 3.47 |
| BPH-278 | 4.20 | 4.10 |
| BPH-670 | 4.16 | 4.64 |
| BPH-461 | 4.16 | 4.34 |
| BPH-470 | 4.12 | 4.14 |
| BPH-721 | 4.10 | 4.70 |
| BPH-472 | 4.07 | 4.46 |
| BPH-483 | 4.04 | 3.84 |
| BPH-476 | 4.00 | 4.58 |
| BPH-683 | 3.97 | 5.17 |
| BPH-475 | 3.94 | 4.37 |
| BPH-684 | 3.90 | 3.89 |
| BPH-527 | 3.87 | 3.36 |
| BPH-474 | 3.85 | 4.42 |
| BPH-682 | 3.84 | 4.02 |
| BPH-686 | 3.81 | 4.24 |
| BPH-685 | 3.81 | 4.02 |
| BPH-477 | 3.80 | 4.77 |
| BPH-727 | 3.77 | 3.62 |
| BPH-536 | 3.72 | 3.24 |
| BPH-540 | 3.59 | 2.68 |

TABLE 2-continued

γδ T cell activation, MCF-7 cell growth inhibition results, presented as -log10(value, M)

| Compound ID | γδ T Cell Avg pED$_{50}$ (M) | MCF-7 Cell pIC$_{50}$ (M) |
|---|---|---|
| BPH-481 | 3.45 | 3.90 |
| BPH-560 | 3.37 | 2.71 |
| BPH-679 | 3.34 | 4.65 |
| BPH-480 | 3.33 | 3.42 |

TABLE 3

Comparison between MCF-7 cell growth inhibition and bone resorption results

| [a]Compound ID | [b]MCF7 Cell pIC$_{50}$ | [c]Bone Resorption pIC$_{50}$ (M) |
|---|---|---|
| BPH-18 | 5.41 | 6.00 |
| BPH-219 | 4.93 | 5.40 |
| BPH-91 | 4.81 | 6.59 |
| BPH-208 | 4.38 | 5.40 |
| BPH-24 | 4.32 | 5.52 |
| BPH-31 | 4.30 | 4.62 |
| BPH-210 | 4.08 | 6.00 |
| BPH-209 | 4.01 | 5.52 |
| BPH-5 | 3.85 | 3.61 |
| BPH-57 | 3.60 | 3.84 |
| BPH-58 | 3.48 | 4.74 |
| BPH-7 | 3.37 | 4.12 |
| BPH-72 | 3.34 | 2.51 |
| BPH-1 | 3.31 | 4.49 |

Figure 10:
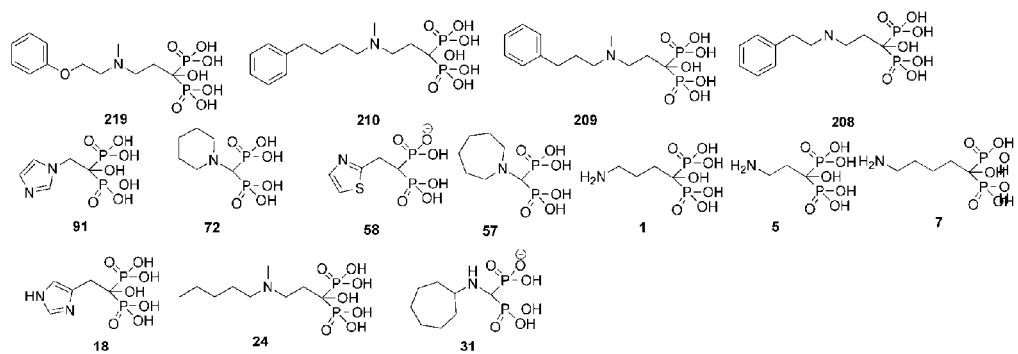
FIG. 10 provides structures of bone resorption drugs tested in MCF-7 cell growth inhibition.

[a]The structures of the molecules investigated are shown in FIG. 10.
[b]The pIC50 values shown are those determined in this work.
[c]The bone resorption results are taken from Widler et al.[19]

TABLE 4

Data collection and refinement statistics for BPH-527[a] bound to human FPPS.

| Data collection | |
|---|---|
| Space group | P4$_1$2$_1$2 |
| Unit cell dimension (Å) | |
| a = b, c | 111.652, 66.841 |
| X-ray source | BNL-X12C[b] |
| Wavelength (Å) | 0.9791 |
| Resolution (Å) | 30-2.70 (2.80-2.70) |
| No. of reflection observed | 135,612 |
| Unique | 12,031 (1,154) |
| Completeness (%) | 99.0 (97.7) |
| R-merge | 0.083 (0.300) |
| I/σI | 8.3 |
| Multiplicity | 11.3 (8.4) |
| Refinement statistics | |
| Resolution range (Å) | 10.0-2.70 |
| R-work/R-free (%) | 22.70/24.38 |
| RMSD | |
| Bond lengths | 0.004 |
| Bond angles | 1.414 |
| No. of atoms | |
| Protein | 2,670 |
| Ligand | 14 |
| PO$_4^{3-}$ | 10 |
| Magnesium ion | 3 |
| Solvent (water) | 71 |
| B average (Å$^2$) of protein | 35.83 |
| B average (Å$^2$) of solvents | 41.37 |
| B average (Å$^2$) of ligands (bisphosphonates, Mg$^{2+}$ and PO$_4^{3-}$) | 30.99 |

[a]BPH-527 is (2-Hydroxy-2,2-bis-phosphono-ethyl)-dimethyl-sulfonium
[b]Brookhaven National Laboratory

TABLE 5

Data collection and refinement statistics for BPH-461[a] bound to human FPPS.

| Data collection | |
|---|---|
| Space group | P4$_1$2$_1$2 |
| Unit cell dimension (Å) | |
| a = b, c | 111.783, 66.525 |
| X-ray source | BNL-X12C[b] |
| Wavelength (Å) | 0.9791 |
| Resolution (Å) | 30-2.40 (2.49-2.40) |
| No. of reflection observed | 204,362 |
| Unique | 16,818 (1,525) |
| Completeness (%) | 98.6 (92.0) |
| R-merge | 0.081 (0.360) |
| I/σI | 10.4 |
| Multiplicity | 12.2 (9.2) |
| Refinement statistics | |
| Resolution range (Å) | 10.0-2.40 |
| R-work/R-free (%) | 23.04/26.95 |
| RMSD | |
| Bond lengths | 0.004 |
| Bond angles | 1.532 |
| No. of atoms | |
| Protein | 2,694 |
| Ligand | 18 |
| PO$_4^{3-\ c}$ | 10 |
| Magnesium ion | 3 |
| Solvent (water) | 94 |
| B average (Å$^2$) of protein | 39.51 |
| B average (Å$^2$) of solvents | 44.51 |
| B average (Å$^2$) of ligands (bisphosphonates, Mg$^{2+}$ and PO$_4^{3-}$) | 37.70 |

[a]BPH-461 is 3-fluoro-1-(2-hydroxy-2,2-bisphosphonoethyl)-pyridinium
[b]Brookhaven National Laboratory

TABLE 6

Data collection and refinement statistics for BPH-527[a] bound to T. brucei FPPS.

| Data collection | |
|---|---|
| Space group | C2 |
| Unit cell dimension (Å) | |
| β(°) | 112.158 |
| a = b, c | 134.613, 118.370, 62.758 |
| X-ray source | BNL-X12C[b] |
| Wavelength (Å) | 1.1 |
| Resolution (Å) | 30-2.00 (2.07-2.00) |
| No. of reflection observed | 461,159 |
| Unique | 61,155 (6,046) |
| Completeness (%) | 99.8 (99.5) |
| R-merge | 0.059 (0.486) |
| I/σI | 12.2 |
| Multiplicity | 7.5 (7.4) |
| Refinement statistics | |
| Resolution range (Å) | 30.0-2.00 |
| R-work/R-free (%) | 20.70/24.12 |

TABLE 6-continued

Data collection and refinement statistics for BPH-527[a] bound to *T. brucei* FPPS.

| | |
|---|---|
| RMSD | |
| Bond lengths | 0.007 |
| Bond angles | 1.183 |
| No. of atoms | |
| Protein | 5,715 |
| Ligand | 28 |
| Magnesium ion | 6 |
| Solvent (water) | 563 |
| B average (Å$^2$) of protein | 28.40 |
| B average (Å$^2$) of solvents | 36.13 |
| B average (Å$^2$) of ligands (bisphosphonates, Mg$^{2+}$) | 22.91 |

[a]BPH-527 is (2-Hydroxy-2,2-bis-phosphono-ethyl)-dimethyl-sulfonium
[b]Brookhaven National Laboratory

TABLE 7

Data collection and refinement statistics for BPH-461[a] bound to *T. brucei* FPPS.

| | |
|---|---|
| Data collection | |
| Space group | C2 |
| Unit cell dimension (Å) | |
| β(°) | 112.364 |
| a = b, c | 135.565, 118.520, 63.186 |
| X-ray source | BNL-X12C[b] |
| Wavelength (Å) | 1.1 |
| Resolution (Å) | 30-2.10 (2.18-2.10) |
| No. of reflection observed | 406,549 |
| Unique | 53,536 (5,267) |
| Completeness (%) | 99.1 (98.3) |
| R-merge | 0.070 (0.483) |
| I/σI | 9.9 |
| Multiplicity | 7.6 (7.6) |
| Refinement statistics | |
| Resolution range (Å) | 30.0-2.10 |
| R-work/R-free (%) | 21.83/25.93 |
| RMSD | |
| Bond lengths | 0.004 |
| Bond angles | 1.532 |
| No. of atoms | |
| Protein | 5,745 |
| Ligand | 36 |
| Magnesium ion | 6 |
| Solvent (water) | 94 |

TABLE 7-continued

Data collection and refinement statistics for BPH-461[a] bound to *T. brucei* FPPS.

| | |
|---|---|
| B average (Å$^2$) of protein | 28.42 |
| B average (Å$^2$) of solvents | 27.60 |
| B average (Å$^2$) of ligands (bisphosphonates, Mg$^{2+}$) | 36.22 |

[a]BPH-461 is 3-fluoro-1-(2-hydroxy-2,2-bisphosphonoethyl)-pyridinium
[b]Brookhaven National Laboratory

TABLE 8

Data collection and refinement statistics for BPH-675[a] bound to *S. cerevisiae* GGPPS.

| | |
|---|---|
| Data collection | |
| Space group | P2$_1$2$_1$2$_1$ |
| Unit cell dimension (Å) | |
| a, b, c | 46.39 116.26 128.70 |
| X-ray source | NSRRC-BL13B1[b] |
| Wavelength (Å) | 1.0 |
| Resolution (Å) | 50-2.20 (2.28-2.20) |
| No. of reflection observed | 246,740 (23,819) |
| Unique | 36,490 (3,555) |
| Completeness (%) | 99.9 (99.9) |
| R-merge | 0.085 (0.424) |
| I/σI | 26.1 (5.5) |
| Multiplicity | 6.8 (6.7) |
| Refinement statistics | |
| Resolution range (Å) | 50-2.2 (2.28-2.2) |
| R-work/R-free (%) | 18.5/24.1 (24.0/29.0) |
| RMSD | |
| Bond lengths | 0.019 |
| Bond angles | 1.7 |
| No. of atoms | |
| Protein | 5,128 |
| Ligand | 47 |
| Magnesium ion | 4 |
| Solvent (water) | 337 |
| B average (Å$^2$) of protein | 40.0 |
| B average (Å$^2$) of solvents | 46.2 |
| B average (Å$^2$) of ligands (bisphosphonates, Mg$^{2+}$) | 61.3 |

[a]BPH-675 is 1-Hydroxy-2-[3'-(Naphthalene-2-sulfonylamino)-biphenyl-3-yl]ethylidene-1,1-bisphosphonic acid
[b]BL13B1 at NSRRC (Hsin-Chu, Taiwan)

TABLE 9

Isothermal calorimetry results

| Cpd ID | *H. sapiens* FPPS IC$_{50}$ μM | *T. brucei* FPPS IC$_{50}$ μM | Δ H (kcal/mol) | Δ delta S | Δ G (kcal/mol) | log (IC$_{50}$) *T. brucei* |
|---|---|---|---|---|---|---|
| BPH-527 | 1.03 | 0.78 | 3.93 | 42.92 | −8.9 | −6.11 |
| BPH-536 | 12.1 | 26.1 | 4.01 | 43.07 | −8.6 | −4.58 |
| BPH-540 | 9 | 11.3 | no signal | | | −4.95 |
| BPH-541 | 38.5 | 544.2 | no signal | | | −3.26 |
| BPH-560 | 1.13 | 275 | 3.78 | 41.52 | −8.5 | −3.56 |
| BPH-571 | 1.82 | 892 | 2.49 | 36.47 | −8.3 | −3.05 |
| BPH-678 | 1.25 | 25.6 | 1.85 | 35.71 | −8.7 | −4.59 |

TABLE 10

2D-QSAR Descriptors and Output

| | |
|---|---|
| QuaSAR-Model(PLS) | /Volumes/hudock/MOE/cancercells/111306/111306.mdb |
| Mon Nov. 13 17:17:44 2006 | |
| Activity Field | pIC50_cancer |
| Weight Field | |
| Condition Limit | 1e+06 |
| Component Limit | 0 |
| Observations | 20 |
| Descriptors | 3 |
| Components Used | 3 |
| Condition Number | 39.156322 |
| ROOT MEAN SQUARE ERROR (RMSE) | 0.49176 |
| CORRELATION COEFFICIENT (R2) | 0.83332 |

ESTIMATED LINEAR MODEL

| | |
|---|---|
| pIC50_cancer = | −6.86627 |
| | +0.37153 * pIC50_hsFPPS |
| | +1.77016 * pIC50_GGPPS |
| | −0.31092 * SlogP |

ESTIMATED NORMALIZED LINEAR MODEL (SD = Standard Deviation)

| | |
|---|---|
| pIC50_cancer/SD(pIC50_cancer) = | −5.70044 |
| | +0.31174 * pIC50_hsFPPS/SD(pIC50_hsFPPS) |
| | +1.39278 * pIC50_GGPPS/SD(pIC50_GGPPS) |
| | −0.65581 * SlogP/SD(SlogP) |

RELATIVE IMPORTANCE OF DESCRIPTORS

| | |
|---|---|
| 0.223827 | pIC50_hsFPPS |
| 1.000000 | pIC50_GGPPS |
| 0.470865 | SlogP |

TABLE 11

CoMSIA Analysis Output
Regression Equation(s)
Use COMFA FIELD RETRIEVE/LIST/GRAPH or EVA RETRIEVE/
LIST/GRAPH CoMFA/EVA coefficients.
MCF_PIC50 = −3.854 + (0.406) * PIC50HSFPPS +
(1.303) * PIC50GGPPS − (0.000) * SLOGP Relative Contributions

| # | | Norm. Coeff. | Fraction |
|---|---|---|---|
| 1 | PIC50HSFPPS | 0.416 | 0.142 |
| 2 | PIC50GGPPS | 1.033 | 0.352 |
| 3 | SLOGP | 0.001 | 0.000183 |
| 4 | COMSIA_ST (1170 vars) | 0.146 | 0.050 |
| 5 | COMSIAHY (1170 vars) | 0.334 | 0.114 |
| 6 | COMSIAEL (1170 vars) | 0.064 | 0.022 |
| 7 | COMSIADO (1170 vars) | 0.487 | 0.166 |
| 8 | COMSIAAC (1170 vars) | 0.451 | 0.154 |

Summary output

| | |
|---|---|
| Standard Error of Estimate | 0.180 |
| R squared | 0.977 |
| F values (n1 = 4, n2 = 17) | 184.083 |
| Prob. of R2 = 0 (n1 = 4, n2 = 17) | 0.000 |

Scrambling Stability Test

| Components | Q2 | csDEP | dq2/dr2yy |
|---|---|---|---|
| 2 | 0.46 | 0.80 | 0.66 |
| 3 | 0.60 | 0.70 | 1.02 |
| 4 | 0.64 | 0.68 | 1.34 |
| 5 | 0.66 | 0.67 | 1.33 |

Materials and Methods.

Cell Growth Inhibition Assays. The human tumor cell lines MCF-7 (breast adenocarcinoma), NCI-H460 (lung large cell) and SF-268 (central nervous system glioblastoma) were obtained from the National Cancer Institute. All lines were cultured in RPMI-1640 medium supplemented with 10% fetal bovine serum and 2 mM L-glutamine at 37° C. in a 5% $CO_2$ atmosphere with 100% humidity. A broth microdilution method was used to determine $IC_{50}$ values for growth inhibition by each bisphosphonate. Cells were inoculated at a density of 5,000 cells/well into 96-well flat bottom culture plates containing 10 μL of the test compound, previously half-log serial diluted (from 0.316 mM to 0.1 μM) for a final volume of 100 μL. NBPs were typically initially dissolved in $H_2O$ (0.01 M) while NNBPs were typically dissolved in DMSO (0.01 M). Plates were then incubated for 4 days at 37° C. in a 5% $CO_2$ atmosphere at 100% humidity after which an MTT ((3-(4,5-dimethylthiazole-2-yl)-2,5-diphenyltetrazolium bromide) cell proliferation assay (ATCC, Manassas, Va.) was used to obtain dose-response curves. The DMSO carrier had no effect on cell proliferation.

GraphPad PRISM® version 4.0 software for windows (GraphPad Software Inc., San Diego, Calif., www.graphpad.com) was used to fit the data to a rectangular hyperbolic function: $I=(I_{max}C)/(IC_{50}+C)$;

$$I = \frac{I_{max}C}{IC_{50} + C}$$

where I is the percent inhibition, $I_{max}$=100% inhibition, C is the concentration of the inhibitor, and $IC_{50}$ is the concentration for 50% growth inhibition. Typical dose-response curves are shown in FIG. 2A, in the text. For the "rescue" experiments, stock solutions of FOH or GGOH were prepared (in ethanol) and the requisite amounts added to the incubation media to produce a fixed 20 μM concentration.

γδ T Cell Assays. Vγ2Vδ2 T cell TNF-α release and proliferation were performed basically as described previously[1]. Briefly, to measure bioactivity for Vγ2Vδ2 T cells, the CD4+ JN.24, CD4+ HF.2, CD8αα+ 12G12, or the CD4−8− HD.108

Vγ2Vδ2 T cell clones were stimulated with phosphoantigens in the presence of CP.EBV (an EBV transformed B cell line) for CD4+ clones or Va-2 (a transformed fibroblast) for CD8αα+ and CD4−8− clones. CP.EBV and Va-2 were fixed with 0.05% glutaraldehyde (EM grade, Sigma, Mo.) for use as APCs. Note that although the relative potencies of the phosphoantigens were similar, the NKG2D+ Vγ2Vδ2 clones, 12G12 and HD.108, exhibited higher antigen sensitivity, likely due to costimulation through their NKG2D receptors by their interaction with the NKG2D ligands, MICA, ULBP2, and ULBP3, that are expressed by the Va-2 cell line. We have previously shown that the NKG2D/MICA interaction significantly increases antigen sensitivity. Concentrations required to achieve 50% of the observed T cell response ($EC_{50}$s) were obtained by using the Prism 4.0 program (Graphpad Software, San Diego, Calif.), using a sigmoidal dose-response function. Curve fitting minima for each experiment (e.g. TNF-α release from JN.24 cells) were determined using the Global Fitting technique, as implemented in Prism 4.0. Curve fitting maxima were optimized for each individual compound without the use of any constraints.

NMR spectroscopy. Spectra were obtained by using the magic-angle sample spinning technique on a 600 MHz ($^1$H resonance frequency) Infinity Plus spectrometer equipped with a 14.1 T, 2 inch bore Oxford magnet and Varian/Chemagnetics 3.2 mm T3 HXY probe. Spectra were referenced to an external standard of 85% orthophosphoric acid. $^1$H transverse magnetization was created by a 3.5 μs pulse (75 kHz field) and cross polarization was used for signal enhancement, followed by TPPM decoupling (80 kHz $^1$H field) during data acquisition. $^1$H-$^{31}$P cross polarization pulse shapes and decoupling were optimized on risedronate (Actonel) prior to data acquisition on the protein samples. Data were acquired using a dwell time of 10 μs (a 100 kHz spectral width), 2048 points, a 2 sec recycle delay and a spinning speed of 13.333 kHz. All spectra were processed by using zero-filling to 4096 points, 50 Hz exponential multiplication, and a polynomial correction for baseline correction prior to peak integration. The number of scans varied between 32 k and 86 k.

Human recombinant GGPPS inhibition. The purification of human recombinant geranylgeranyl diphosphate synthase (hGGPPS) followed the protocol reported previously[2]. GGPPS inhibition by bisphosphonates was determined using the radiometric assay reported previously[2] with slight modification. The assay solution contained 300 ng of hGGPPS, 50 mM potassium phosphate buffer (pH 7.0), 5 mM $MgCl_2$, 2 mM DTT, 1 mg/mL BSA, and 25 μM FPP in a total volume of 50 μL and was preincubated with the bisphosphonates at room temperature for 15 min. Then, the reactions were started by adding 5 μL of a 250 μM solution of [$^{14}$C] IPP and incubated at 37° C. for 20 min. The reaction was terminated by the addition of 75 μL of HCl/MeOH. Following a second 20 min incubation at 37° C. to effectively hydrolyze the allylic pyrophosphates, the reaction mixtures were neutralized by the addition of 75 μL of 6 N NaOH and extracted with 500 μL of hexane. 200 μL of the organic phase was transferred to a scintillation vial for counting. The $IC_{50}$ values were obtained by fitting the data to the dose-response curve in Origin 6.1 (OriginLab Corp., Northampton, Mass., www.OriginLab.com).

Crystallization and X-ray Data Collection for Human FPPS-Bisphosphonate Complexes. Crystals human FPPS complexed with Mg and either BPH-461 or BPH-527 were obtained based on the methods described by K. L. Kavanagh et al.[3], with slight modification. FPPS was incubated with 2.5 mM bisphosphonate, 2.5 mM $MgCl_2$ overnight on ice before setting up the drops. Crystals were grown at room temperate in sitting drops by mixing 2 μL of protein solution and 1 μL of precipitant, which consisted of 40% (v/v) of either polyethylene glycol 2,000 or 4,000 and 0.1 M phosphate/citrate buffer, pH 4.2. Diffraction data were obtained at 100 K using an ADSC Q315 CCD detector at the Brookhaven National Synchrotron Light Source, beamline X29 (λ=1.1 Å). Data collection statistics are reported in the Example 3 section herein.

Crystallization and X-ray Data Collection of *T. brucei* FPPS-Bisphosphonate Complexes. Initial crystallization screening conditions were based on crystallization conditions reported by Mao et al[4]. The effects of protein concentration, precipitant type and concentration, buffer type, buffer pH value and metal-ion concentration were then optimized and protein crystals that gave good diffraction patterns were obtained. Protein at 5.55 mg/mL was mixed with 2.5 mM BPH-461 or BPH-527, 2.5 mM $MgCl_2$ and incubated overnight on ice before setting up the drops. Crystals were grown at room temperature in hanging drops by mixing 1 μL of FPPS-bisphosphonate mixture solution with 1 μL of precipitant consisting of 10% (v/v) MPD in 100 mM ammonium acetate, pH 5.75. Prior to data collection, crystals were mounted in a cryoloop and flash-frozen in liquid nitrogen after the addition of 40% (v/v) MPD as cryoprotectant. Diffraction data were obtained at 100 K using an ADSC Q4 CCD detector at the Brookhaven National Synchrotron Light Source beamline X8C (λ=1.1 Å). Data collection statistics are reported in Tables 6 and 7.

Structure determination of Human FPPS-Bisphosphonate Complexes. For structure determination, the human FPPS structure ($1YV5)_3$ minus the risedronate ligand was used as a search model using the molecular replacement method. Rigid body refinement was applied to the model obtained using AMoRe5. The crystal structure was then further refined by using Shelxl-97[6]. Rebuilding and fitting the ligand was carried out by using the program O[7] in the 2Fo-Fc electron density map. Certain refinement statistics are included in Tables 4 and 5.

Structure determination of *T. brucei* FPPS-Bisphosphonate Complexes. The crystal structures of the *T. brucei* FPPS bisphosphonate complexes were determined by using the molecular replacement method using the program AMoRe[5]. The previously solved *T. brucei* FPPS structure (2EWG)[8] minus the minodronate ligand was used as a starting model. The structure has been further refined using CNS[9]. After iterative rounds of refinement using CNS and rebuilding using Coot, the structures had the final refinement statistics shown in Tables 6 and 7.

2D QSAR: Molecular Descriptors. Structures of inhibitors were imported into the Molecular Operating Environment (MOE) 2006.08[10]. In order to compute certain molecular descriptors, a three-dimensional structure was required. The three-dimensional models were built by minimizing all molecules using a 0.05 kcal/mol gradient and MMFF94[11] force field. In addition to computed 2D molecular descriptors, GGPPS and FPPS enzyme $pIC_{50}$ values were also used. The AutoQuaSAR module[12], an expert system for QSAR in MOE, was used. This iteratively builds a series of models by evaluating the importance of each of the descriptors available, removing less important ones in a step-wise fashion in order to produce a trajectory of $r^2$ and $q^2$ (leave-one-out cross-validated $r^2$) as a function of the number of descriptors. The models having the fewest components and the highest $r^2$ and $q^2$, were then selected for inspection. The final model computer output is shown in Table 10.

3D-QSAR: CoMSIA Descriptors and Analysis. Conformers of all compounds were generated in MOE 2006.08[10] using the conformation import utility. In order to avoid potential bias in the alignment, the pharmacophore perception algorithm (in MOE) was used to generate alignments of the molecules, based on overlap of perceived features, specifically: hydrophobic, aromatic, cation, donor and acceptor. The ranked list of putative pharmacophores then served as the basis for initial alignment[13]. Alignment of molecules in the top pharmacophore (containing a cationic feature) was selected and refined sequentially using the flexible alignment module in MOE with TAFF (Tripos) and MMFF94 force fields. Aligned molecules and charges were imported into Sybyl 7.3[14] along with corresponding FPPS, GGPPS and MCF-7 activity data. CoMSIA[15] descriptors were calculated for the aligned molecules with additional descriptors added, including FPPS $pIC_{50}$, GPPS $pIC_{50}$ and SLogP. PLS was used to assign contributions of each of the components, which resulted in $q^2=0.806$ (3 components). The computer output is show in Table 11.

A scrambling stability test, as implemented in Sybyl 7.3[14], was then performed on the data to ensure that the model was not obtained due to chance and, additionally, to verify the optimum number of components. The scrambling method applies small, random perturbations to the dataset while monitoring the predictivity of the resulting models. The predictivity of unstable models typically falls off disproportionately rapidly from even small perturbations, while robust models exhibit more predictive stability[16]. The output results, confirming stability at three components, are shown in Table 11.

Hologram HQSAR (HQSAR). Hologram QSAR, unlike CoMSIA, does not require a common three-dimensional structural alignment, but rather is a fragment-based, alignment independent method that serves as a performance baseline that is difficult to outperform by comparable methods[17]. The HQSAR method, as implemented in Sybyl 7.3[14], uses an extended molecular fingerprint (molecular hologram) to correlate structural features and biological activity. Structures of the 64 molecules were imported into Sybyl 7.3 and three dimensional coordinates generated for ease of structure inspection and verification using up to 10,000 steps at 0.01 kcal/mol gradient using the BFGS[18] energy minimization method. Structures were then automatically fragmented into pre-defined fragment sizes. A molecular hologram (fingerprint) was then generated for each molecule using these fragments, retaining information about the fragment, possible overlap and constituent sub-fragments, implicitly encoding three-dimensional structure information. The hologram was then used for partial least squares (PLS) analysis to produce cross-validated models, obtaining a final model having $q^2=0.674$ and $r^2=0.871$ and optimal fragment size of 83 bits.

REFERENCES CITED IN THIS SECTION

1. Song, Y.; Zhang, Y.; Wang, H.; Raker, A. M.; Sanders, J. M.; Broderick, E.; Clark, A.; Morita, C. T.; Oldfield, E., Synthesis of Chiral Phosphoantigens and Their Activity in γδ T Cell Stimulation. Bioorg Med Chem Lett 2004, 14, (17), 4471-7.
2. Szabo, C. M.; Matsumura, Y.; Fukura, S.; Martin, M. B.; Sanders, J. M.; Sengupta, S.; Cieslak, J. A.; Loftus, T. C.; Lea, C. R.; Lee, H. J.; Koohang, A.; Coates, R. M.; Sagami, H.; Oldfield, E., Inhibition of Geranylgeranyl Diphosphate Synthase by Bisphosphonates and Diphosphates: A Potential Route to New Bone Antiresorption and Antiparasitic Agents. J Med Chem 2002, 45, (11), 2185-96.
3. Kavanagh, K. L.; Guo, K.; Dunford, J. E.; Wu, X.; Knapp, S.; Ebetino, F. H.; Rogers, M. J.; Russell, R. G.; Oppermann, U., The molecular mechanism of nitrogen-containing bisphosphonates as antiosteoporosis drugs. Proc Natl Acad Sci USA 2006, 103, (20), 7829-34.
4. Mao, J.; Gao, Y. G.; Odeh, S.; Robinson, H.; Montalvetti, A.; Docampo, R.; Oldfield, E., Crystallization and Preliminary X-ray Diffraction Study of the Farnesyl Diphosphate Synthase from *Trypanosoma brucei*. Acta Crystallogr D Biol Crystallogr 2004, 60, (Pt 10), 1863-6.
5. Navaza, J., AMoRe: an automated package for molecular replacement. Acta Crystallog. sect. A 1994, 50, 157-163.
6. Sheldrick, G.; Schneider, T., SHELXL: High Resolution Refinement. Methods in Enzymology 1997, 277, 319-343.
7. Jones, T. A.; Zou, J. Y.; Cowan, S. W.; Kjeldgaard, M., Improved methods for building protein models in electron density maps and the location of errors in these models. Acta Crystallographica Section A 1991, 47, 110-119.
8. Mao, J.; Mukherjee, S.; Zhang, Y.; Cao, R.; Sanders, J. M.; Song, Y.; Zhang, Y.; Meints, G. A.; Gao, Y. G.; Mukkamala, D.; Hudock, M. P.; Oldfield, E., Solid-state NMR, crystallographic, and computational investigation of bisphosphonates and farnesyl diphosphate synthase-bisphosphonate complexes. J Am Chem Soc 2006, 128, (45), 14485-97.
9. Brunger, A. T.; Adams, P. D.; Clore, G. M.; DeLano, W. L.; Gros, P.; Grosse-Kunstleve, R. W.; Jiang, J. S.; Kuszewski, J.; Nilges, M.; Pannu, N. S.; Read, R. J.; Rice, L. M.; Simonson, T.; Warren, G. L., Crystallography & NMR system: A new software suite for macromolecular structure determination. Acta Crystallogr D Biol Crystallogr 1998, 54, (Pt 5), 905-21.
10. MOE, 2006.08; Chemical Computing Group, Inc.: Montreal, Quebec, 2006.
11. Halgren, T. A.; Nachbar, R. B., MMF94: The Merck molecular force field. Bridging the gap—From small organics to proteins. Abstracts of Papers of the American Chemical Society 1996, 211, 70-COMP.
12. Goto, J. AutoQuaSAR 2006.08, Ryoka Systems, Inc.: Tokyo, Japan, 2006.
13. Zhu, L. L.; Hou, T. J.; Chen, L. R.; Xu, X. J., 3D QSAR analyses of novel tyrosine kinase inhibitors based on pharmacophore alignment. J Chem Inf Comput Sci 2001, 41, (4), 1032-40.
14. Sybyl 7.3, Tripos, Inc.: St. Louis, Mo.
15. Klebe, G.; Abraham, U.; Mietzner, T., Molecular similarity indices in a comparative analysis (CoMSIA) of drug molecules to correlate and predict their biological activity. J Med Chem 1994, 37, (24), 4130-46.
16. Tripos Bookshelf 7.3, Tripos, Inc.: St. Louis, Mo.
17. Gedeck, P.; Rohde, B.; Bartels, C., QSAR—how good is it in practice? Comparison of descriptor sets on an unbiased cross section of corporate data sets. J Chem Inf Model 2006, 46, (5), 1924-36.
18. Press, W. H., Numerical recipies in C: the art of scientific computing. Cambridge University Press: New York, 1988; p 324.
19. Widler, L.; Jaeggi, K. A.; Glatt, M.; Muller, K.; Bachmann, R.; Bisping, M.; Born, A. R.; Cortesi, R.; Guiglia, G.; Jeker, H.; Klein, R.; Ramseier, U.; Schmid, J.; Schreiber, G.; Seltenmeyer, Y.; Green, J. R., Highly Potent Feminal Bisphosphonates. From Pamidronate disodium (Aredia) to Zoledronic Acid (Zometa). J Med Chem 2002, 45, (17), 3721-38.

Example 4

Anti-Cancer Activity Including Such Against Tumors In Vivo

Tumor cell invasiveness and in vivo results. We investigated whether lipophilic bisphosphonates can have pronounced effects on tumor cell invasiveness. When MDA-MB-231 cells, an invasive human breast cancer adenocarcinoma cell line, were cultured with bisphosphonates in a Matrigel invasion assay, the lipophilic bisphosphonate, BPH-716, was about 1000-fold more inhibitory than was zoledronate (BPH-716, $IC_{50}$ about 30 nM; versus zoledronate, $IC_{50}$ about 40 μM). To determine whether such compounds had activity in vivo, we used SK-ES-1 sarcoma cells in a mouse xenograft system (Kubo 2007). While zoledronate caused a significant (p<0.01) reduction in tumor cell growth versus control, the effect of a lipophilic bisphosphonate (BPH-715) was even more pronounced (p=0.032 versus zoledronate), and there was no weight loss or other adverse effect observed. Activity in this mouse model can be attributed to direct activity on tumor cell growth and invasiveness, since murine gammadelta T cells lack the Vγ2Vδ2 T cell receptor required for activation by IPP. These results demonstrate that more lipophilic bisphosphonates have potent, direct activity against tumor cell proliferation/invasiveness, both in vitro and in vivo. They can also have enhanced potency in human T cell activation, believed due to IPP accumulation.

In vivo tumor cell model. Experiments were carried out basically as described in Kubo 2006 et al.[47] Xenografts of human SK-ES-1 cells were initiated by subcutaneous injections of $1.5 \times 10^7$ cells into the right flank of four, 6-week old athymic nude mice (CLEA, Tokyo, Japan). The mice received daily intraperitoneal injections of 5 μg of zoledronate, BPH-715 or physiological saline. The smallest and largest diameters of tumors, and the body weights, were measured weekly. Tumor volumes were calculated using the following formula: volume $(mm^3)$=(smallest diameter)$^2$×(largest diameter)/2. Statistical significance was determined by one-way ANOVA and Fisher's PLSD method, using Statcel (OMS Ltd., Saitama, Japan); p<0.05 was considered to be significant.

REFERENCES

Kubo, T., Shimose, S., Matsuo, T., Sakai, A. & Ochi, M. Efficacy of a nitrogen-containing bisphosphonate, minodronate, in conjunction with a p38 mitogen activated protein kinase inhibitor or doxorubicin against malignant bone tumor cells. Cancer Chemother. Pharmacol. (2007).

Kubo, T. et al. Inhibitory effects of a new bisphosphonate, minodronate, on proliferation and invasion of a variety of malignant bone tumor cells. J. Orthop. Res. 24, 1138-44 (2006).

Example 5

Structural Formulas of Compounds

In addition to structural formulas for compounds provided elsewhere in the specification and drawings, certain structural formulas are provided below.

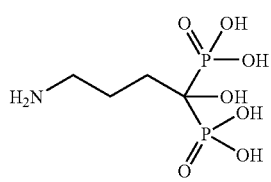

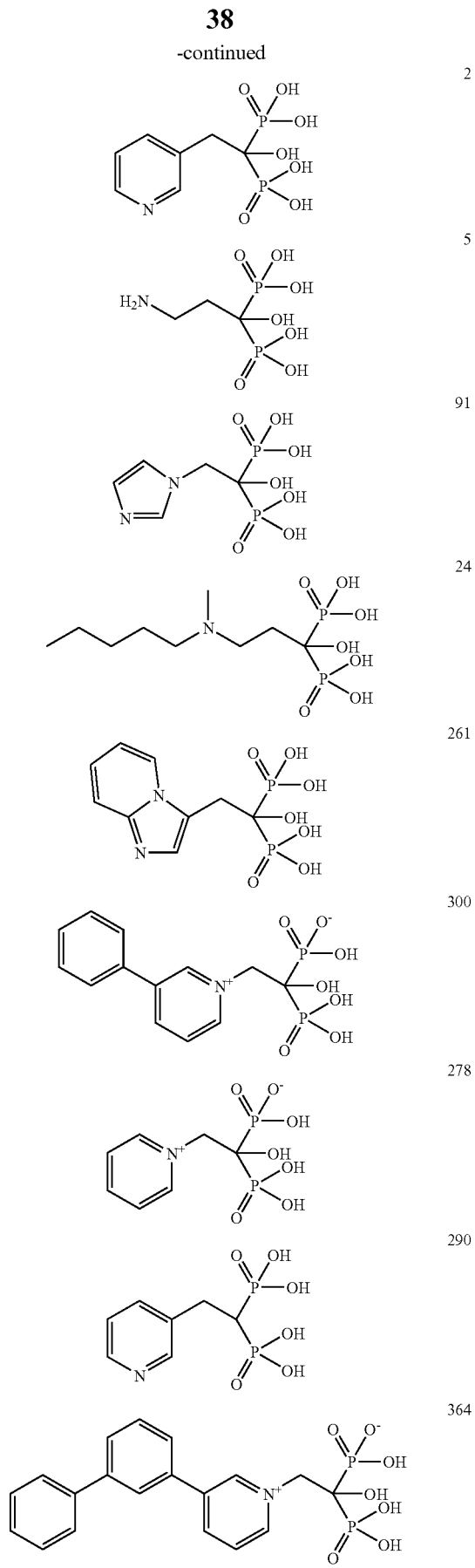

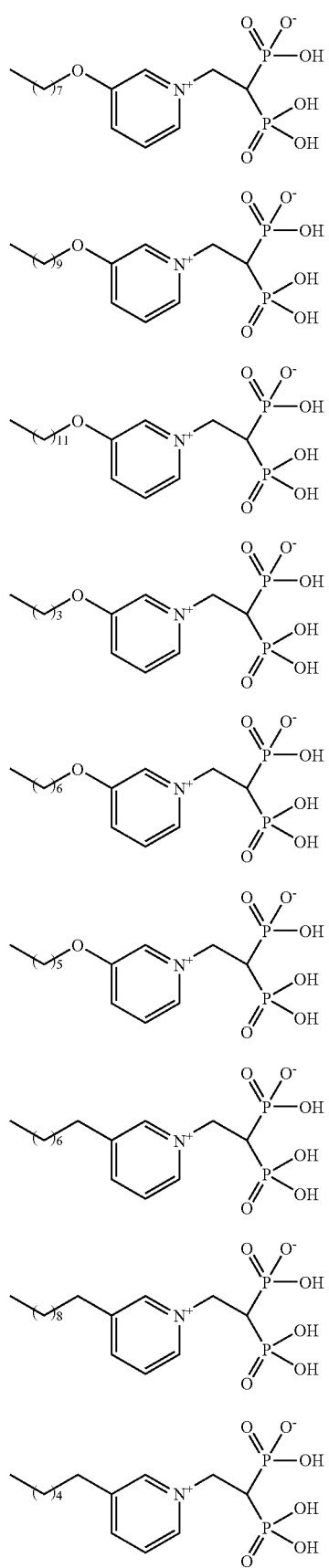
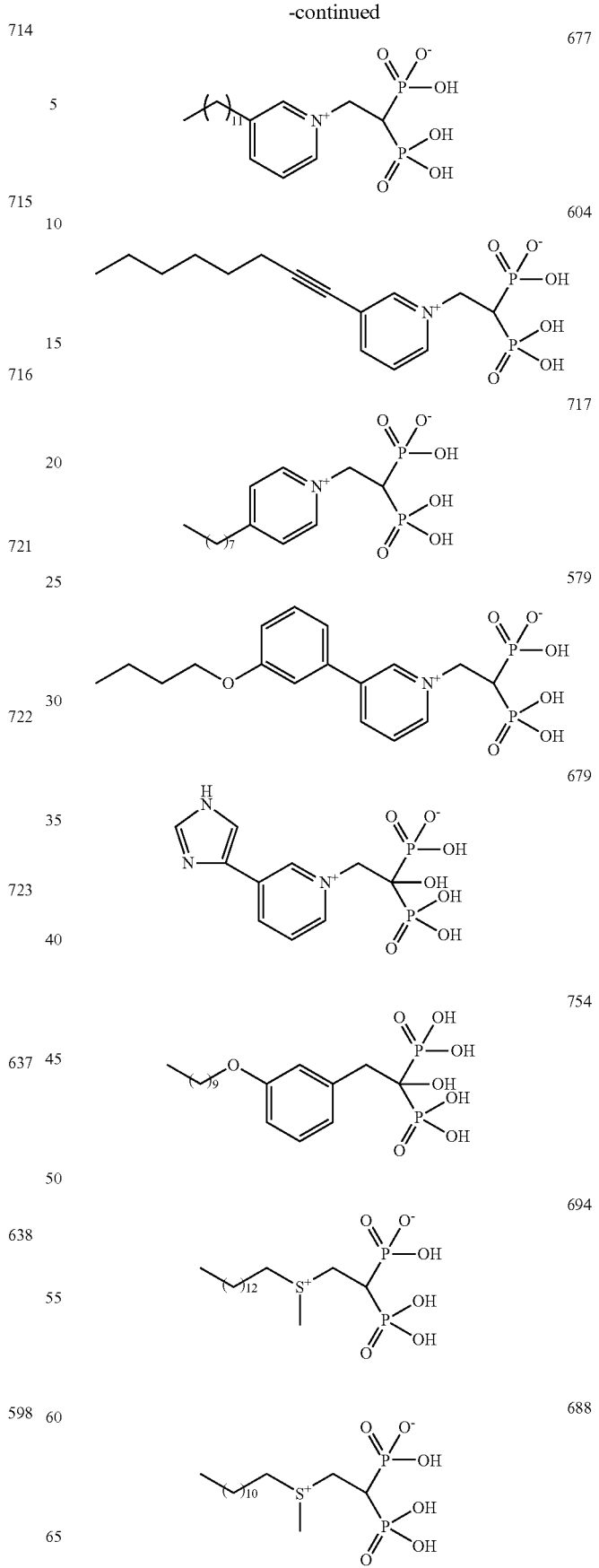

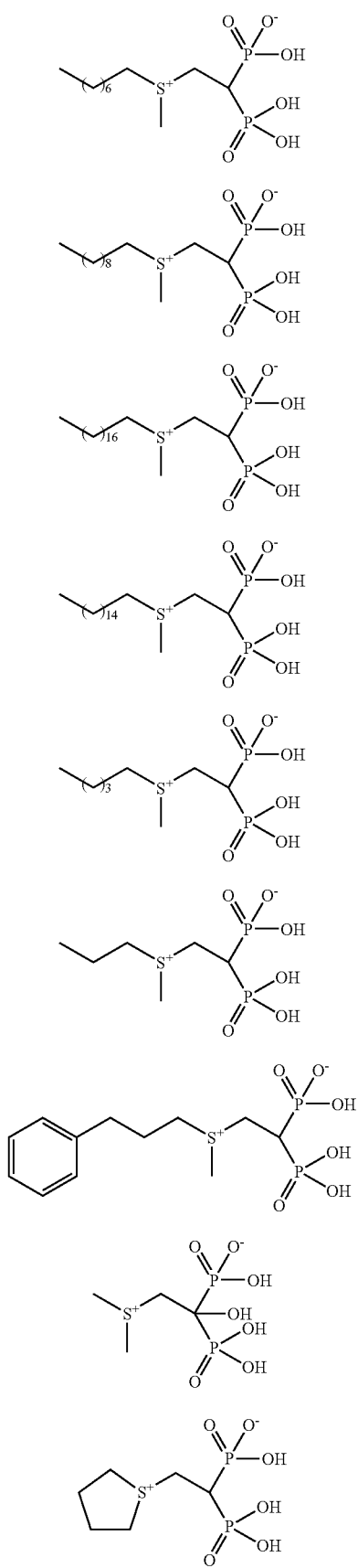
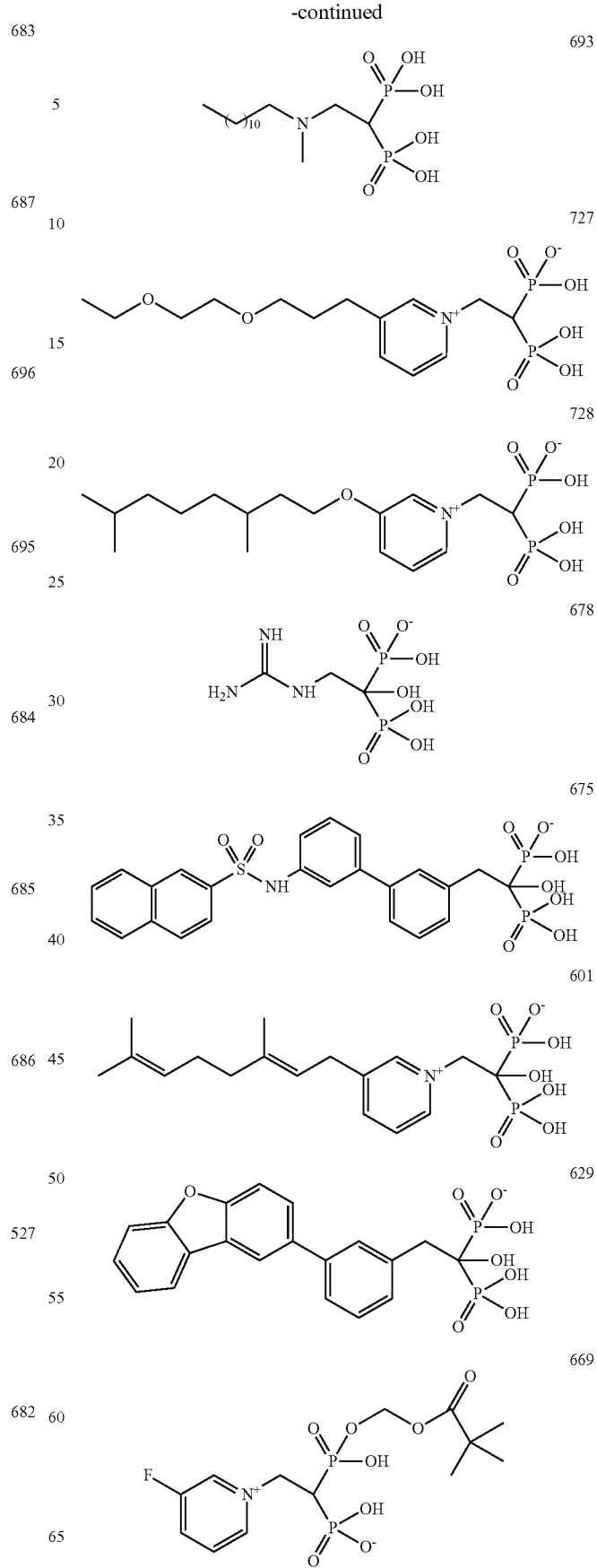

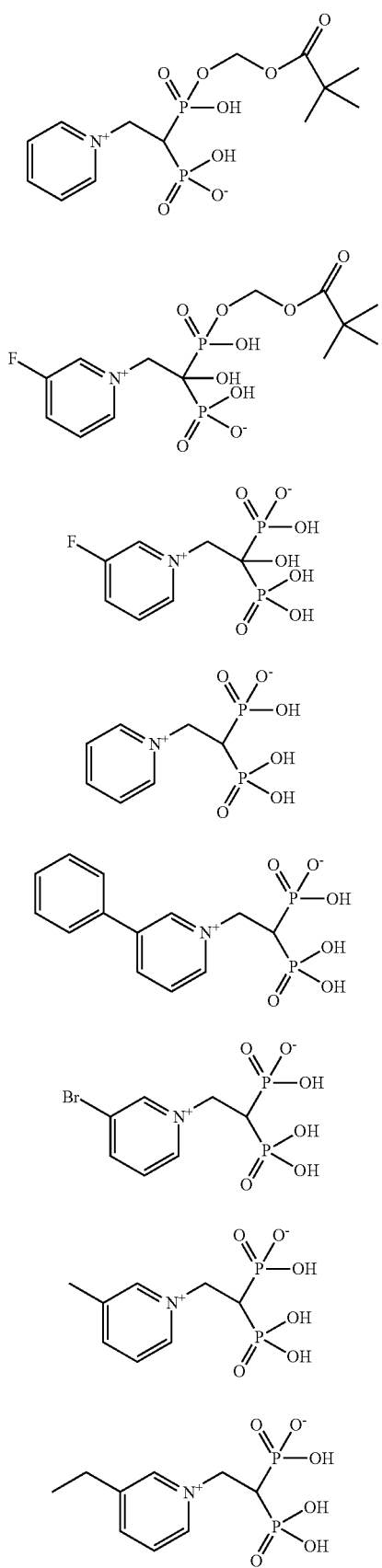
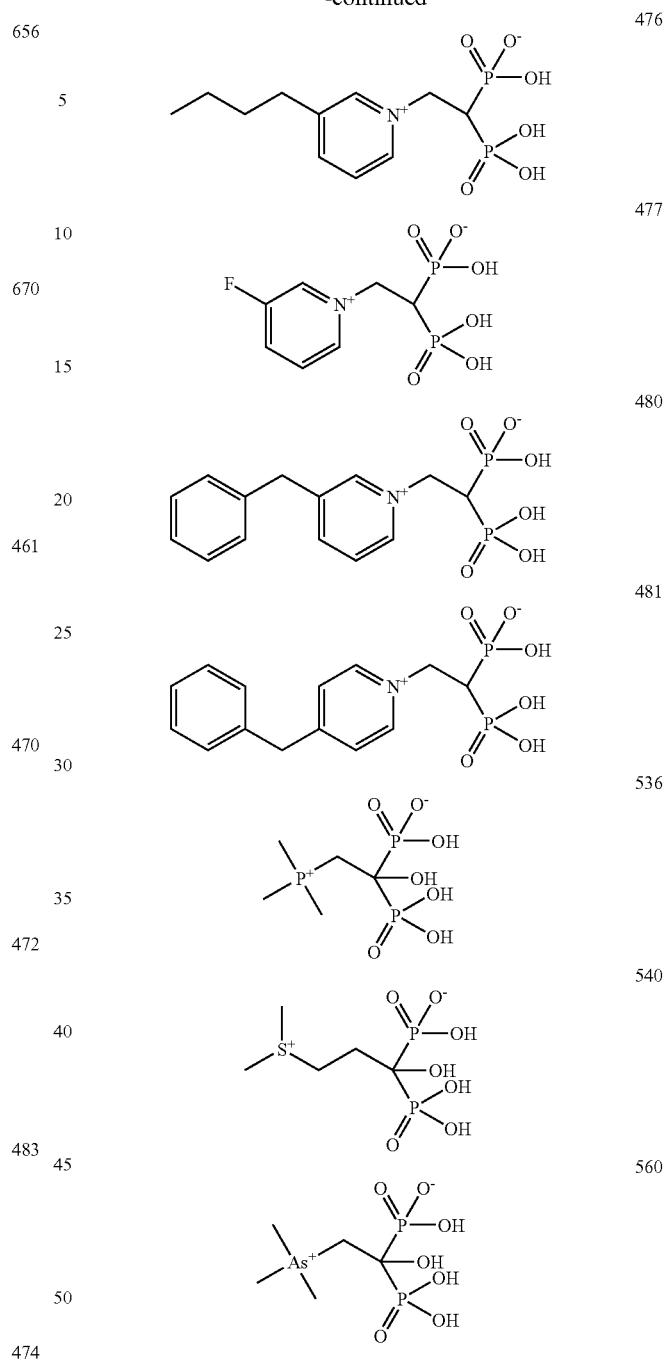
Certain data in FIG. 2D is further represented in Table 12 below.
TABLE 12
Matrix with several enzyme targets.
|  | FPPS | GGPPS | DPPS | Cells | SlogP |
|---|---|---|---|---|---|
| FPPS | 100 | −33 | 27 | −7 | −34 |
| GGPPS | −33 | 100 | 12 | 81 | 85 |
| DPPS | 27 | 12 | 100 | 23 | −6 |
| Cells | −7 | 81 | 23 | 100 | 63 |
| SlogP | −34 | 85 | −6 | 63 | 100 |

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a temperature range, a time range, a composition or concentration range, or other value range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. As used herein, "comprising" is thus synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms equivalent to "comprising", "consisting essentially of" and "consisting of" may be replaced with either of the other two terms to signify the respective meaning which can indicate a difference in scope. The invention illustratively described herein suitably may be practiced in the absence of any element or elements, limitation or limitations which is not specifically disclosed herein.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. For example, one of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents of methods, devices, device elements, materials, procedures and techniques described herein are intended to be encompassed by this invention. This invention is not to be limited by the specific embodiments disclosed, including any shown in the drawings or exemplified in the specification, which are given by way of example or illustration and not of limitation. It should be understood that although the present invention has been specifically disclosed by in some cases preferred embodiments and optional features, modification and variation of the innovative concepts herein disclosed may be resorted to by those skilled in the art, and that such modifications and variations are considered to be within the scope of this invention as further defined by the appended claims.

REFERENCES

U.S. application Ser. No. 11/687,570 filed Mar. 17, 2006; PCT International Application Serial PCT/US07/64239 filed Mar. 17, 2006; U.S. Application Ser. 60/783,491 filed Mar. 17, 2006; U.S. application Ser. No. 11/245,612 filed Oct. 7, 2005 (see also US Patent Application Publication No. 20060079487 published Apr. 13, 2006); U.S. Application Ser. 60/617,108 filed Oct. 8, 2004; PCT International Application No. PCT/US05/036425 filed Oct. 7, 2005 (see also International Publication No. WO/2006/039721 published Apr. 13, 2006); US Patent Application Publication No. 20050113331 published May 26, 2005; each of the foregoing in particular is incorporated by reference in entirety to the extent not inconsistent herewith.

Hudock M P et al., Acta Cryst. (2006). E62, o843-o845.
Cao R et al., Acta Cryst. (2006). E62, o1003-o1005
Zhang Y et al., Acta Cryst. (2006). E62, o1006-o1008
Cao R et al., Acta Cryst. (2006). E62, o1055-o1057
Zhang Y et al., J Med. Chem. 2006 Sep. 21; 49(19):5804-14.
(1) Sambrook, P. N.; Geusens, P.; Ribot, C.; Solimano, J. A.; Ferrer-Barriendos, J.; Gaines, K.; Verbruggen, N.; Melton, M. E. Alendronate produces greater effects than raloxifene on bone density and bone turnover in postmenopausal women with low bone density: results of EFFECT (EFficacy of FOSAMAX versus EVISTA Comparison Trial) International. J. Intern. Med. 2004, 255, 503-511.
(2) Vasireddy, S.; Talwakar, A.; Miller, H.; Mehan, R.; Swinson, D. R. Patterns of pain in Paget's disease of bone and their outcomes on treatment with pamidronate. Clin. Rheumatol. 2003, 22, 376-380.
(3) Dawson, N. A. Therapeutic benefit of bisphosphonates in the management of prostate cancer-related bone disease. Expert. Opin. Pharmacother. 2003, 4, 705-716.
(4) Rosen, L. S.; Gordon, D. H.; Dugan, W. Jr.; Major, P.; Eisenberg, P. D.; Provencher, L.; Kaminski, M.; Simeone, J.; Seaman, J.; Chen, B. L.; Coleman, R. E. Zoledronic acid is superior to pamidronate for the treatment of bone metastases in breast carcinoma patients with at least one osteolytic lesion. Cancer 2004, 100, 36-43.
(5) Cromartie, T. H.; Fisher, K. J.; Grossman, J. N. The discovery of a novel site of action for herbicidal bisphosphonates. Pesticide Biochem. Phys. 1999, 63, 114-126.
(6) Cromartie, T. H.; Fisher, K. J. Method of controlling plants by inhibition of farnesyl pyrophosphate synthase. U.S. Pat. No. 5,756,423, May 26, 1998.
(7) van Beek, E.; Pieterman, E.; Cohen, L.; Löwik, C.; Papapoulos, S, Nitrogen-containing bisphosphonates inhibit isopentenyl pyrophosphate isomerase/farnesyl pyrophosphate synthase activity with relative potencies corresponding to their antiresorptive potencies in vitro and in vivo. Biochem. Biophys. Res. Commun. 1999, 255, 491-494.
(8) van Beek, E.; Pieterman, E.; Cohen, L.; Löwik, C.; Papapoulos, S. Farnesyl pyrophosphate synthase is the molecular target of nitrogen-containing bisphosphonates. Biochem. Biophys. Res. Commun. 1999, 264, 108-111.
(9) Keller, R. K.; Fliesler, S. J. Mechanism of aminobisphosphonate action: characterization of alendronate inhibition of the isoprenoid pathway. Biochem. Biophys. Res. Commun. 1999, 266, 560-563.
(10) Bergstrom, J. D.; Bostedor, R. G.; Masarachia, P. J.; Reszka, A. A.; Rodan, G. Mechanism of aminobisphosphonate action: characterization of alendronate inhibition of the isoprenoid pathway. Arch. Biochem. Biophys. 2000, 373, 231-241.
(11) Grove, J. E.; Brown, R. J.; Watts, D. J. The intracellular target for the antiresorptive aminobisphosphonate drugs in *Dictyostelium discoideum* is the enzyme farnesyl diphosphate synthase. J. Bone Miner. Res. 2000, 15, 971-981.
(12) Dunford, J. E.; Thompson, K.; Coxon, F. P.; Luckman, S. P.; Hahan, F. M.; Poulter, C. D.; Ebetino, F. H.; Rogers, M. J. Structure-activity relationships for inhibition of farnesyl diphosphate synthase in vitro and inhibition of bone resorption in vivo by nitrogen-containing bisphosphonates. J. Pharmacol. Exp. Ther. 2001, 296, 235-242.
(13) Luckman, S. P.; Hughes, D. E.; Coxon, F. P.; Graham, R.; Russell, G.; Rogers, M. J. Nitrogen-containing bisphosphonates inhibit the mevalonate pathway and prevent post-translational prenylation of GTP-binding proteins, including Ras. J. Bone Miner. Res. 1998, 13, 581-589.
(14) Fisher, J. E.; Rogers, M. J.; Halasy, J. M.; Luckman, S. P.; Hughes, D. E.; Masarachia, P. J.; Wesolowski, G.; Russell, R. G.; Rodan, G. A.; Reszka, A. A. Alendronate mechanism of action: geranylgeraniol, an intermediate in the mevalonate pathway, prevents inhibition of osteoclast formation, bone resorption, and kinase activation in vitro. Proc. Natl. Acad. Sci. USA 1999, 96, 133-138.
(15) van Beek, E.; Löwik, C.; van der Pluijm, G.; Papapoulos, S. The role of geranylgeranylation in bone resorption and its suppression by bisphosphonates in fetal bone explants in vitro: A clue to the mechanism of action of nitrogen-containing bisphosphonates. J. Bone Miner. Res. 1999, 14, 722-729.
(16) Montalvetti, A.; Bailey, B. N.; Martin, M. B.; Severin, G. W.; Oldfield, E.; Docampo, R. Bisphosphonates are potent inhibitors of *Trypanosoma cruzi* farnesyl pyrophosphate synthase. J. Biol. Chem. 2001, 276, 33930-33937.
(17) Sanders, J. M.; Gómez, A. O.; Mao, J.; Meints, G. A.; van Brussel, E. M.; Burzynska, A.; Kafarski, P.; González-Pacanowska, D.; Oldfield, E. 3-D QSAR investigations of the inhibition of *Leishmania major* farnesyl pyrophosphate synthase by bisphosphonates. J. Med. Chem. 2003, 46, 5171-5183.
(18) Martin, M. B.; Grimley, J. S.; Lewis, J. C.; Heath, H. T. III; Bailey, B. N.; Kendrick, H.; Yardley, V.; Caldera, A.; Lira, R.; Urbina, J. A.; Moreno, S, N.; Docampo, R.; Croft, S. L.; Oldfield, E. Bisphosphonates inhibit the growth of *Trypanosoma brucei, Trypanosoma cruzi, Leishmania donovani, Toxoplasma gondii*, and *Plasmodium falciparum*: A potential route to chemotherapy. J. Med. Chem. 2001, 44, 909-916.
(19) Martin, M. B.; Sanders, J. M.; Kendrick, H.; de Luca-Fradley, K.; Lewis, J. C.; Grimley, J. S.; van Brussel, E. M.; Olsen, J. R.; Meints, G. A.; Burzynska, A.; Kafarski, P.; Croft, S. L.; Oldfield, E. Activity of bisphosphonates against *Trypanosoma brucei rhodesiense*. J. Med. Chem. 2002, 45, 2904-2914.
(20) Moreno, B.; Bailey, B. N.; Luo, S.; Martin, M. B.; Kuhlenschmidt, M.; Moreno, S, N.; Docampo, R.; Oldfield, E. 31P NMR of apicomplexans and the effects of risedronate on *Cryptosporidium parvum* growth. Biochem. Biophys. Res. Commun. 2001, 284, 632-637.
(21) Ghosh, S.; Chan, J. M.; Lea, C. R.; Meints, G. A.; Lewis, J. C.; Tovian, Z. S.; Flessner, R. M.; Loftus, T. C.; Bruchhaus, I.; Kendrick, H.; Croft, S. L.; Kemp, R. G.; Kobayashi, E. Effects of bisphosphonates on the growth of *Entamoeba histolytica* and *Plasmodium* species in vitro and in vivo. J. Med. Chem. 2004, 47, 175-187.
(22) Yardley, V.; Khan, A. A.; Martin, M. B.; Slifer, T. R.; Araujo, F. G.; Moreno, S, N.; Docampo, R.; Croft, S. L.; Oldfield, E. In vivo activities of farnesyl pyrophosphate synthase inhibitors against *Leishmania donovani* and *Toxoplasma gondii*. Antimicrob. Agents Chemother. 2002, 46, 929-931.
(23) Rodriguez, N.; Bailey, B. N.; Martin, M. B.; Oldfield, E.; Urbina, J. A.; Docampo, R. Radical cure of experimental cutaneous leishmaniasis by the bisphosphonate pamidronate. J. Infect. Dis. 2002, 186, 138-140.
(24) Garzoni, L. R.; Caldera, A.; Meirelles, M. N. L.; de Castro, S. L.; Meints, G.; Docampo, R.; Oldfield, E.; Urbina, J. A. Selective in vitro effects of the farnesyl pyrophosphate synthase inhibitor risedronate on *Trypanosoma cruzi*. Intl. J. Antimicrobial Agents 2004, 23, 273-285.
(25) Garzoni, L. R.; Waghabi, M. C.; Baptista, M. M.; de Castro, S. L.; Meirelles, M. N. L.; Britto, C.; Docampo, R.; Oldfield, E.; Urbina, J. A. Antiparasitic activity of risedronate in a murine model of acute Chagas' disease. Intl. J. Antimicrobial Agents 2004, 23, 286-290.

(26) Wang, L.; Kamath, A.; Das, H.; Li, L.; Bukowski, J. F. Antibacterial effect of human Vgamma2Vdelta2 T cells in vivo. J. Clin. Invest. 2001, 108, 1349-1357.

(27) Kunzmann, V.; Bauer, E.; Feurle, J.; Weissinger, F.; Tony, H. P.; Wilhelm,

M. Stimulation of γδ T cells by aminobisphosphonates and induction of antiplasma cell activity in multiple myeloma. Blood 2000, 96, 384-392.

(28) Kato, Y.; Tanaka, Y.; Miyagawa, F.; Yamashita, S.; Minato, N. Targeting of tumor cells for human gammadelta T cells by nonpeptide antigens. J. Immunol. 2001, 167, 5092-5098.

(29) Thompson, K.; Rogers, M. J. Statins prevent bisphosphonate-induced gammadelta-T-cell proliferation and activation in vitro. J. Bone Miner. Res. 2004, 19, 278-288.

(30) Sanders, J. M.; Ghosh, S.; Chan, J. M. W.; Meints, G.; Wang, H.; Raker, A. M.; Song, Y.; Colantino, A.; Burzynska, A.; Kafarski, P.; Morita, C. T.; Oldfield, E. Quantitative structure-activity relationships for gammadelta T cell activation by bisphosphonates. J. Med. Chem. 2004, 47, 375-384.

(31) Wilhelm, M.; Kunzmann, V.; Eckstein, S.; Reimer, P.; Weissinger, F.; Ruediger, T.; Tony, H. P. gammadelta T cells for immune therapy of patients with lymphoid malignancies. Blood 2003, 102, 200-206.

(32) Miyaura, N; Yanagi, T; Suzuki, A. The palladium-catalyzed cross-coupling reaction of phenylboronic acid with haloarenes in the presence of bases. Synth. Commun. 1981, 11, 513-519.

(33) Krapcho, A. P.; Ellis, M. Synthesis of regioisomeric difluoro- and 8-chloro-9-fluorobenz[g]isoquinoline-5,10-diones and SNAr displacements studies by diamines: bis (aminoalkyl)aminobenz[g]isoquinoline-5,10-diones. J. Fluorine Chem. 1998, 90, 139-147.

(34) Zhang, L.; Liang, F.; Sun, L.; Hu, Y.; Hu, H. A novel and practical synthesis of 3-unsubstituted indolizines. Synthesis 2000, 1733-1737.

(35) Harel, Z.; Kovalevski-Liron, E.; Lidor-Hadas, R.; Lifshitz-Liron, R. Use of certain diluents for making bisphosphonic acids. World Patent WO03097655, Nov. 27, 2003.

(36) Rogers, M. J.; Watts, D. J.; Russell, R. G.; Ji, X.; Xiong, X.; Blackburn, G. M.; Bayless, A. V.; Ebetino, F. H. Inhibitory effects of bisphosphonates on growth of amoebae of the cellular slime mold *Dictyostelium discoideum*. J. Bone Miner. Res. 1994, 9, 1029-1039.

(37) van Beek, E. R.; Cohen, L. H.; Leroy, I. M.; Ebetino, F. H.; Löwik, C. W.; Papapoulos, S. E. Differentiating the mechanisms of antiresorptive action of nitrogen containing bisphosphonates. Bone 2003, 33, 805-11.

U.S. Pat. Nos. 5,583,122 by Benedict et al., issued Dec. 10, 1996; 6,562,974 by Cazer et al., issued May 13, 2003; 6,544,967 by Daifotis et al., issued Apr. 8, 2003; 6,410,520 by Cazer et al., issued Jun. 25, 2002; 6,372,728 by Ungell, issued Apr. 16, 2002; 6,638,920 by Thompson, issued Oct. 28, 2003; 4,777,163 by Bosies et al., issued Oct. 11, 1988; 4,939,130 by Jaeggi et al., issued Jul. 3, 1990; 4,859,472 by Demmer et al., issued Aug. 22, 1989; U.S. Pat. No. 5,227,506 by Saari et al., issued Jul. 13, 1993; U.S. Pat. No. 6,753,324 by Jomaa, issued Jun. 22, 2004. U.S. Pat. No. 5,294,608

Alfer'ev, I. S.; Mikhalin, N. V., Reactions of vinylidenediphosphonic acid with nucleophiles. 5. Addition of heterocyclic amines and trimethylamine to vinylidenediphosphonic acid; August 1994, Russian Chemical Bulletin 44(8):1528-1530 (translated from Izvestiya Akademii Nauk, Seriya Khimicheskaya 1995, 8, 1590-1592).

Alfer'ev I S et al., Izvestiay Akademii Nauk SSSR, Seriya Khimicheskaya, No. 12, pp. 2802-2806, December 1983 [Bull. Acad. Sci. USSR, Div. Chem. Sci., 1983, 32:2515 (Engl. Transl.)].

Alfer'ev I S et al., Izv. Akad. Nauk SSSR, Ser. Khim., 1984: 1122 [Bull. Acad. Sci. USSR, Div. Chem. Sci., 1984, 33:1031 (Engl. Transl.)].

International Publication No. WO03075741 by Wilder et al., published 18 Sep. 2003; International Publication No. WO2004024165 by Baulch-Brown et al., published 25 Mar. 2004; German Patent Publication DE19859668 by Hassan, published 30 Dec. 1999; International Publication No. WO2004050096 by Romagne et al., published 17 Jun. 2004.

Widler L, et al., Highly potent geminal bisphosphonates. From pamidronate disodium (Aredia) to zoledronic acid (Zometa), J Med. Chem. 2002 Aug. 15; 45(17):3721-38.

Green J R, Chemical and biological prerequisites for novel bisphosphonate molecules: results of comparative preclinical studies, Semin Oncol. 2001 April; 28(2 Suppl 6):4-10.

U.S. Pat. No. 4,711,880 by Stahl et al., issued Dec. 8, 1987 (Aredia/pamidronate); U.S. Pat. No. 4,621,077, U.S. Pat. No. 5,462,932, U.S. Pat. No. 5,994,329, U.S. Pat. No. 6,015,801, U.S. Pat. No. 6,225,294 (Fosamax/alendronate); U.S. Pat. No. 5,583,122, U.S. Pat. No. 6,096,342; U.S. Pat. No. 6,165,513 (Actonel/risedronate).

Wilhelm M et al., 2003, Gammadelta T cells for immune therapy of patients with lymphoid malignancies, Blood 102: 200-206.

Jagdev S P, Coleman R E, Shipman C M, Rostami H A, Croucher P I (2001); The bisphosphonate, zoledronic acid, induces apoptosis of breast cancer cells: evidence for synergy with paclitaxel. Br J Cancer 84:1126-1134.

U.S. Pat. No. 4,927,814 by Gall et al., issued May 22, 1990; U.S. Pat. No. 6,294,196 by Gabel et al., issued Sep. 25, 2001; U.S. Pat. No. 6,143,326 by Mockel, et al. issued Nov. 7, 2000 (ibandronate/Boniva®); U.S. Pat. No. 6,544,967 by Daifotis, et al. Apr. 8, 2003.

Heidenreich et al., 2004. Ibandronate in metastatic bone pain, Semin. Oncol. 31(5 Suppl 10):67-72.

Gordon D H, 2005. Efficacy and safety of intravenous bisphosphonates for patients with breast cancer metastatic to bone: a review of randomized, double-blind, phase III trials, Clin Breast Cancer. 6(2):125-31.

De Cock et al., 2005. Cost-effectiveness of oral ibandronate versus IV zoledronic acid or IV pamidronate for bone metastases in patients receiving oral hormonal therapy for breast cancer in the United Kingdom. Clin. Ther. 27(8): 1295-310.

Sanders et al., Pyridinium-1-yl Bisphosphonates Are Potent Inhibitors of Farnesyl Diphosphate Synthase and Bone Resorption, J. Med. Chem. 2005, 48, 2957-296.

Kotsikorou Evangelia et al., Bisphosphonate Inhibition of the Exopolyphosphatase Activity of the *Trypanosoma brucei* Soluble Vacuolar Pyrophosphatase, J. Med. Chem. 2005, 48, 6128-6139.

Inoue S et al., 2003 Synthesis, 13:1971-1976. New synthesis of gem-Bis(phosphono)ethylenes and their Applications.

Soloducho J et al., 1997. Patent PL93-298436, Preparation of novel derivatives of (aminomethylene)bis(phosphonic acid) as herbicides.

Lecouvey M et al., 2001, Tet. Lett. 42:8475-8478, A mild and efficient one-pot synthesis of 1-hydroxymethylene-1,1-bisphosphonic acids. Preparation of new tripod ligands.

Kieczykowski G R et al., 1995, J. Org. Chem. 60:8310-8312, Preparation of (4-amino-1-hydroxybutylidene)bisphosphonic and sodium salt, MK-217 (alendronate sodium). An improved procedure for the preparation of 1-hydroxy-1,1-bisphosphonic acids.

Liang P-H, 2002, Eur. J. Biochem. 269, 3339-3354 (2002), Review Article, Structure, mechanism and function of prenyltransferases.

Goldstein J L, Brown M S: Regulation of the mevalonate pathway. Nature 343:425, 1990.

Swanson K M, Hohl R J, Curr Cancer Drug Targets. 2006 February; 6(1):15-37. Anti-cancer therapy: targeting the mevalonate pathway.

Wiemer A J, Tong H, Swanson K M, Hohl R J; Biochem Biophys Res Commun. 2007 Feb. 23; 353(4):921-5. Digeranyl bisphosphonate inhibits geranylgeranyl pyrophosphate synthase.

The invention claimed is:

1. A compound of formula XA1:

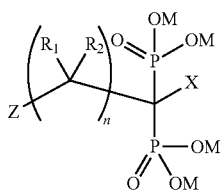

or salts or hydrates thereof, wherein;

X is hydrogen, hydroxyl group, or a halogen;

each M is independently selected from the group consisting of a negative charge, a hydrogen, an alkyl group, and a —$(CH_2)_p$—O—CO—R or —$(CH_2)_p$—O—CO—O—R group, where p is 1 to 6, and R is selected from the group consisting of hydrogen, optionally substituted alkyl and optionally substituted aryl; or —OM is a salt of form —$O^-A^+$, where $A^+$ is a cation;

n is 1, 2, or 3;

each $R_1$ and $R_2$, independently, is selected from the group consisting of a hydrogen, a halogen, —$N(R)_2$, —SR', OR', an optionally substituted alkyl, an optionally substituted alkenyl, and an optionally substituted aryl group, where each R' is independently selected from the group consisting of H, an optionally substituted alkyl group and an optionally substituted aryl group, and one of $R_1$ and one of $R_2$ together optionally form a 3-10 member carbocyclic or heterocyclic ring containing one to three heteroatoms, particularly N, S, and O;

Z is

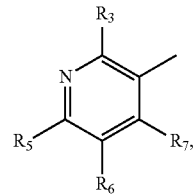

Z1

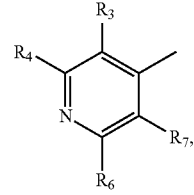

Z2

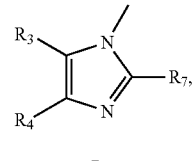

Z3

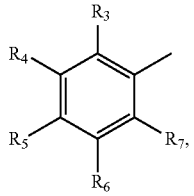

Z4

Z5

Z12 wherein $R_3$-$R_7$ are independently selected from the group consisting of a hydrogen, a halogen, —CN, —OR''', —COOR''', —OCOOR''', —COR''', —CON(R''')_2, —OCON(R''')_2, —N(R''')_2, —NO_2, —SR, —SO_2R, —SO_2N(R''')_2, —SOR''' group, an optionally substituted alkyl group, an optionally substituted alkenyl group, an optionally substituted alkynyl group and an optionally substituted aryl group, where each R or R''' is independently selected from H, an optionally substituted alkyl group, an optionally substituted aryl group, and an optionally substituted acyl group;

wherein at least one of $R_3$-$R_7$ is RL, where RL is selected from the group consisting of alkyl, alkoxy, alkenyl, alkynyl, alkenoxy and alkynoxy groups having 6 to 20 carbon atoms, each of which are optionally substituted; alkyl ether groups which are alkyl groups having 6-20 carbon atoms in which one or more non-adjacent carbon atoms are replaced with an O; and a 3-$R_M$ or 4-$R_M$ substituted phenyl group, where $R_M$ is selected from the group consisting of alkyl, alkenyl, alkynyl, alkoxy, alkenyoxy, alkynoxy and alkyl ether groups having 3-15 carbon atoms; and wherein the other ring positions of the phenyl ring are optionally substituted with one or more halogens, or one or more optionally substituted alkyl groups having 1-3 carbon atoms.

2. The compound of claim 1 wherein Z is any one of Z1-Z5.
3. The compound of claim 1 wherein Z is Z1 and $R_4$ is RL.
4. The compound of claim 1 wherein Z is Z1 and $R_5$ is RL.
5. The compound of claim 1 wherein Z is Z1 and $R_6$ is RL.
6. The compound of claim 1 wherein Z is Z2 and $R_4$ is RL.
7. The compound of claim 1 wherein Z is Z2 and $R_5$ is RL.
8. The compound of claim 1 wherein Z is Z2 and $R_6$ is RL.
9. The compound of claim 1 wherein Z is Z3 and $R_3$ is RL.
10. The compound of claim 1 wherein Z is Z3 and $R_5$ is RL.
11. The compound of claim 1 wherein Z is Z3 and $R_6$ is RL.

12. The compound of claim 1 wherein Z is Z5, and $R_3$ is RL.

13. The compound of claim 1 wherein Z is Z5 and $R_4$ is RL.

14. The compound of claim 1 wherein RL is selected from the group consisting of alkyl, alkenyl, alkynyl and alkoxy groups having 7-20 carbon atoms.

15. The compound of claim 1 wherein RL is selected from the group consisting of alkyl, alkynyl and alkoxy groups having 7-20 carbon atoms.

16. The compound of claim 1 wherein RL is a group selected from alkyl, or alkynyl groups having 7-14 carbon atoms or 8-12 carbon atoms.

17. The compound of claim 1 wherein RL is an alkoxy group having 7-14 carbon atoms or 8-12 carbon atoms.

18. The compound of claim 1 wherein RL is a straight-chain alkyl or alkoxy group having 7-10 carbons atoms.

19. The compound of claim 1 wherein RL is a straight-chain alkyl group having 8-20 carbon atoms.

20. The compound of claim 1 wherein Z is Z1-Z5 and RL is an alkynyl group —C≡C—$R_{AK}$ where $R_{AK}$ is a straight-chain alkyl group having 4-20 carbon atoms or 5-10 carbon atoms.

21. The compound of claim 1 wherein RL is an alkyl ether group which is an alkyl group having 7-20 carbon atoms or 7-14 carbon atoms in which one or more non-adjacent carbon atoms are replaced with an O.

22. The compound of claim 1 wherein RL is a 3-$R_M$ or 4-$R_M$ substituted phenyl group, where $R_M$ is selected from the group consisting of alkyl, alkenyl, alkynyl, alkoxy, alkenyoxy, alkynoxy and alkyl ether groups having 3-15 carbon atoms or 6-12 carbon atoms, where the other ring positions of the phenyl ring are optionally substituted with one or more halogens, or one or more optionally substituted alkyl groups having 1-3 carbon atoms.

23. The compound of claim 1 wherein $R_3$-$R_7$, which are not RL, are selected from the group consisting of a hydrogen, a halogen, an optionally substituted alkyl group, an optionally substituted alkenyl group, an optionally substituted alkynyl group, an optionally substituted alkoxy group, and an optionally substituted aryl group.

24. The compound of claim 1 wherein $R_3$-$R_7$ which are not RL, are selected from hydrogens, halogens or unsubstituted alkyl groups having 1-3 carbon atoms.

25. The compound of claim 1 wherein $R_3$-$R_7$, which are not RL, are all hydrogens.

26. The compound of claim 1 wherein $R_4$ is a straight-chain alkyl group having 6-20 carbon atoms or 7-17 carbon atoms or 8-15 carbon atoms.

27. A pharmaceutical composition comprising a therapeutically effective amount of the compound of claim 1 and a pharmaceutically acceptable carrier or excipient.

28. A compound selected from the group consisting of:

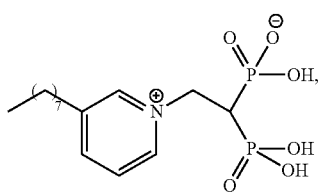

-continued

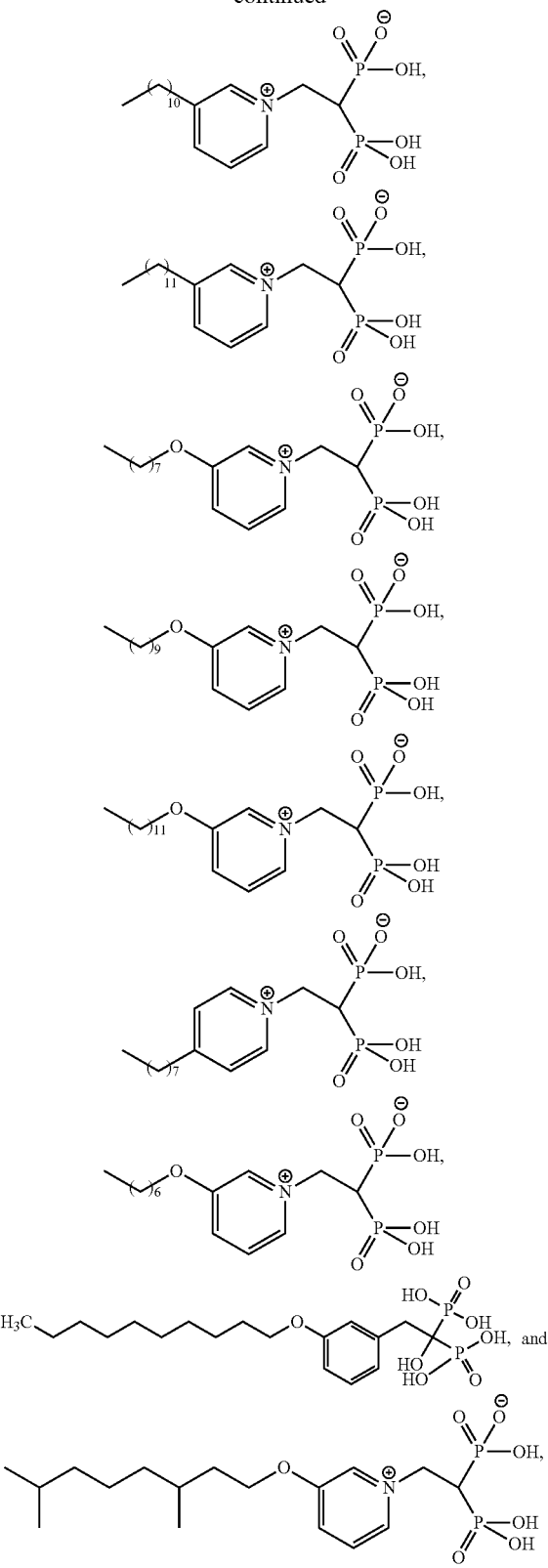

and for each respective said compound, a pharmaceutically acceptable salt or ester thereof.

29. The compound of claim 1 wherein X is hydroxyl or halogen.

30. The compound of claim 1 wherein X is hydroxyl.

31. The compound of claim 1 wherein X is hydrogen.

32. The compound of claim 1 wherein Z is Z1 and RL is a straight chain alkoxy having 7 to 20 carbon atoms.

33. A compound having the structural formula

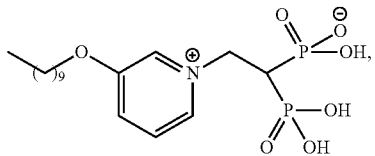

or a salt, ester, or pharmaceutical formulation thereof.

34. A compound having a structural formula selected from:

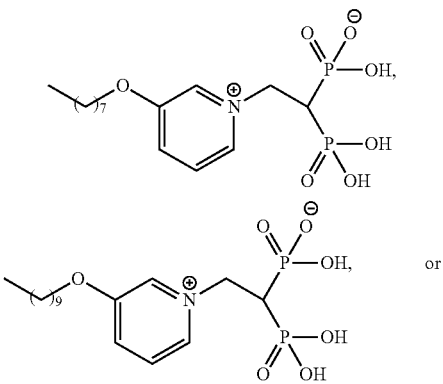

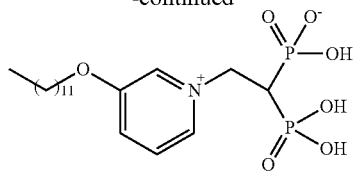

or a salt, ester, or pharmaceutical formulation thereof.

35. A compound of claim 1 wherein Z is Z1, $R_4$ is RL and RL is a straight-chain alkyl or a straight-chain alkoxy group having 7 to 20 carbons atoms or a pharmaceutical formulation thereof.

36. The compound of claim 35 wherein X is hydrogen or hydroxyl.

37. The compound of claim 35 wherein $R_3$ and $R_5$-$R_7$ are selected from hydrogens, halogens or unsubstituted alkyl groups having 1-3 carbon atoms.

38. The compound of claim 35 wherein $R_3$ and $R_5$-$R_7$ are hydrogens.

39. A compound of claim 35 wherein Z is Z1, $R_4$ is RL and RL is a straight-chain alkoxy group having 7 to 20 carbons atoms or a pharmaceutical formulation thereof.

40. The compound of claim 39 wherein X is hydrogen or hydroxyl.

41. A compound of claim 1 wherein Z is Z1, $R_4$ is RL and RL is an alkoxy group having 7 to 20 carbons atoms or a pharmaceutical formulation thereof.

42. The compound of claim 39 wherein X is hydrogen or hydroxyl.

43. A compound of claim 1 wherein Z is Z1, $R_4$ is RL and RL is an alkoxy group having 8-12 carbons atoms or a pharmaceutical formulation thereof.

44. The compound of claim 43 wherein X is hydrogen or hydroxyl.

* * * * *